(12) United States Patent
Beatty et al.

(10) Patent No.: US 12,226,425 B2
(45) Date of Patent: Feb. 18, 2025

(54) INHIBITORS OF ARG1 AND/OR ARG2

(71) Applicant: Arcus Biosciences, Inc., Hayward, CA (US)

(72) Inventors: Joel Beatty, San Mateo, CA (US); Eric Thomas Newcomb, Menlo Park, CA (US); Jay Patrick Powers, Pacifica, CA (US); Brandon Reid Rosen, San Mateo, CA (US); Yongli Su, Foster City, CA (US); Anh Thu Tran, Union City, CA (US); Corinne Nicole Foley, San Carlos, CA (US); Rebecca Louise Grange, Union City, CA (US); Tezcan Guney, Hayward, CA (US); Steven Donald Jacob, Oakland, CA (US); Jaroslaw Kalisiak, Mountain View, CA (US); Manmohan Reddy Leleti, Dublin, CA (US); Erick Allen Lindsey, Fremont, CA (US); Debashis Mandal, Fremont, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 925 days.

(21) Appl. No.: 17/294,353

(22) PCT Filed: Nov. 15, 2019

(86) PCT No.: PCT/US2019/061657
§ 371 (c)(1),
(2) Date: May 14, 2021

(87) PCT Pub. No.: WO2020/102646
PCT Pub. Date: May 22, 2020

(65) Prior Publication Data
US 2022/0016143 A1 Jan. 20, 2022

Related U.S. Application Data

(60) Provisional application No. 62/768,284, filed on Nov. 16, 2018.

(51) Int. Cl.
| | | |
|---|---|---|
| *A61K 31/69* | (2006.01) | |
| *A61K 31/282* | (2006.01) | |
| *A61K 31/704* | (2006.01) | |
| *A61K 33/243* | (2019.01) | |
| *A61K 39/395* | (2006.01) | |
| *C07F 5/02* | (2006.01) | |

(52) U.S. Cl.
CPC ............ *A61K 31/69* (2013.01); *A61K 31/282* (2013.01); *A61K 31/704* (2013.01); *A61K 33/243* (2019.01); *A61K 39/3955* (2013.01); *C07F 5/025* (2013.01)

(58) Field of Classification Search
CPC .... A61K 31/69; A61K 33/243; A61K 31/282; A61K 31/704; A61K 39/3955; C07F 5/025
See application file for complete search history.

(56) References Cited

U.S. PATENT DOCUMENTS

| | | |
|---|---|---|
| 2011/0077381 A1 | 3/2011 | Osterkamp et al. |
| 2012/0083469 A1 | 4/2012 | Van Zandt et al. |
| 2015/0191492 A1 | 7/2015 | Van Zandt et al. |
| 2017/0121352 A1 | 5/2017 | Sjogren et al. |
| 2017/0319536 A1 | 11/2017 | Blaszczyk et al. |
| 2018/0009830 A1 | 1/2018 | Blaszczyk et al. |

FOREIGN PATENT DOCUMENTS

| | | |
|---|---|---|
| WO | WO-9919295 | 4/1999 |
| WO | WO-2009154737 | 12/2009 |
| WO | WO-2010075863 | 7/2010 |
| WO | WO-2010085797 | 7/2010 |
| WO | WO-2011133653 | 10/2011 |
| WO | WO-2012058065 | 5/2012 |
| WO | WO-2012091757 | 7/2012 |
| WO | WO-2013059437 | 4/2013 |
| WO | WO-2013158262 | 10/2013 |
| WO | WO-2014007831 | 1/2014 |
| WO | WO-2014201161 | 12/2014 |
| WO | WO-2015160664 | 10/2015 |
| WO | WO-2016037298 | 3/2016 |
| WO | WO-2016100555 | 6/2016 |
| WO | WO-2016108707 | 7/2016 |
| WO | WO-2016210106 | 12/2016 |
| WO | WO-2017075363 | 5/2017 |

(Continued)

OTHER PUBLICATIONS

Schafer et al. Drug Discovery Today 2008, 13 (21/22), 913-916 (Year: 2008).*
Horig et al. Journal of Translational Medicine 2004, 2(44) (Year: 2004).*
Sosnowska et al. Oncoimmunology 2021, 10(1) (Year: 2021).*
Munder. British Journal of Pharmacology (2009), 158,638-651 (Year: 2009).*
Abdelkawy et al., Pharmacokinetics and Pharmacodynamics of Promising Arginase Inhibitors, Eur J Drug Metab Pharmacokinet, published Oct. 12, 2016, 16 pages, doi 10.1007/s13318-016-0381-y.

(Continued)

*Primary Examiner* — Daniel R Carcanague
*Assistant Examiner* — Jerica Katlynn Wilson
(74) *Attorney, Agent, or Firm* — DLA Piper LLP; Melissa Harwood

(57) ABSTRACT

Compounds that are inhibitors of at least one of ARG1 and ARG2, and compositions containing the compounds and methods for synthesizing the compounds, are described herein. The use of such compounds and compositions for the treatment of a diverse array of diseases, disorders, and conditions, including cancer- and immune-related disorders that are mediated, at least in part, by ARG1 and ARG2 are also described herein.

11 Claims, No Drawings

(56) References Cited

FOREIGN PATENT DOCUMENTS

| WO | 2017191130 A2 | 11/2017 |
|---|---|---|
| WO | 2018089490 A1 | 5/2018 |
| WO | 2018022668 A3 | 4/2019 |
| WO | WO-2019173188 | 9/2019 |
| WO | WO-2019245890 | 12/2019 |

OTHER PUBLICATIONS

Cama et al., Design of amino acid sulfonamides as transition-state analogue inhibitors of arginase, J Am Chem Soc. 2003, vol. 125, pp. 13052-13057.

Di Costanzo et al., Crystal structure of human arginase I complexed with thiosemicarbazide reveals an unusual thiocarbonyl μ-sulfide ligand in the binuclear manganese cluster, J. Am. Chem. Soc. 2007, vol. 129, pp. 6388-6389.

Guo et al., Synthesis and in vitro antibacterial activity of fluoroquinolone derivatives containing 3-(N'-alkoxycarbamimidoyl)-4-(alkoxyimino) pyrrolidines, European Journal of Medicinal Chemistry 2010, vol. 45, pp. 5498-5506.

Ilies et al., 2-Aminoimidazole Amino Acids as Inhibitors of the Binuclear Manganese Metalloenzyme Human Arginase I, J. Med. Chem. 2010, vol. 53, pp. 4266-4276.

Ilies et al., Binding of α,α-Disubstituted Amino Acids to Arginase Suggests New Avenues for Inhibitor Design, Journal of Medicinal Chemistry 2011, vol. 54, pp. 5432-5443.

International Search Report and Written Opinion for International Application No. PCT/US2019/020507 dated Jul. 29, 2019. 11 pages.

Lisi et al., Antiretrovirals inhibit arginase in human microglia, Journal of Neurochemistry 2016, vol. 136, pp. 363-372.

Mitcheltree et al., Discovery and Optimization of Rationally Designed Bicyclic Inhibitors of Human Arginase to Enhance Cancer Immunotherapy, ACS Medicinal Chemistry Letters 2020, vol. 11, pp. 582-588.

Mitcheltree et al., Supporting Information for Discovery and Optimization of Rationally Designed Bicyclic Inhibitors of Human Arginase to Enhance Cancer Immunotherapy, ACS Medicinal Chemistry Letters 2020, 171 pages.

Pethe et al., Interaction of anions with rat liver arginase: specific inhibitory effects of fluoride, Journal of Inorganic Biochemistry 2002, vol. 88, pp. 397-402.

Pham et al., Cinnamide Derivatives as Mammalian Arginase Inhibitors: Synthesis, Biological Evaluation and Molecular Docking, International Journal of Molecular Sciences 2016, vol. 17, 1656, 17 pages.

PubChem CID 67513622, XIEAQQGNISCWOO-DKIAZLNASA-N, Create Date: Nov. 30, 2012, p. 2, structure—retrieved from the internet Aug. 20, 2021, 8 pages.

Pudlo et al., Arginase Inhibitors: A Rational Approach Over One Century, Medicinal Research Reviews 2016, 00, No. 0, pp. 1-39.

Van Zandt et al., Discovery of (R)-2-Amino-6-borono-2-(2-(piperidin-1-yl)ethyl)hexanoic Acid and Congeners As Highly Potent Inhibitors of Human Arginases I and II for Treatment of Myocardial Reperfusion Injury, Journal of Medicinal Chemistry 2013, vol. 56, pp. 2568-2580.

Zakharian et al., (S)-2-Amino-6-nitrohexanoic Acid Binds to Human Arginase I through Multiple Nitro-Metal Coordination Interactions in the Binuclear Manganese Cluster, J Am Chem Soc. 2008, vol. 130, pp. 17254-17255.

Zhang et al., Benzoxaborole Antimalarial Agents. Part 5. Lead Optimization of Novel Amide Pyrazinyloxy Benzoxaboroles and Identification of a Preclinical Candidate, Journal of Medicinal Chemistry 2017, vol. 60, pp. 5889-5908.

International Search Report and Written Opinion for International Application No. PCT/US2019/061657 dated Jan. 17, 2020. 7 pages.

* cited by examiner

INHIBITORS OF ARG1 AND/OR ARG2

CROSS-REFERENCES TO RELATED APPLICATIONS

This application is a U.S. National Stage Application under 35 U.S.C. § 371 of International Application No. PCT/US2019/061657, filed Nov. 15, 2019, which is an application claiming benefit under 35 U.S.C. § 119(e) of U.S. Provisional Application No. 62/768,284, filed Nov. 16, 2018, which are herein incorporated by reference in their entireties.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Arginase plays a fundamental role in the hepatic urea cycle, metabolizing L-arginine to L-ornithine and urea. In addition, arginase has been shown to be either responsible for or to participate in inflammation-triggered immune dysfunction, tumor immune escape, immunosuppression and immunopathology of infectious disease [Bronte V, Zanovello P (2005b). Regulation of immune responses by L-arginine metabolism. *Nat Rev Immunol* 5: 641-654].

In humans, two arginase isoenzymes exist, arginase I (ARG-1) and arginase II (ARG-2). They catalyse the same biochemical reaction but differ in cellular expression, regulation and subcellular localization [Jenkinson et al. (1996). Comparative properties of arginases. *Comp Biochem Physiol B Biochem Mol Biol* 114: 107-132]. ARG-1 depletes arginine from the tumor microenvironment, leading to impaired T cell function such as stopped proliferation and secretion of cytokines. [Rodriguez et al (2002). Regulation of T cell receptor CD3zeta chain expression by L-arginine. J Biol Chem 277: 21123-21129; Munder, Arginase in the Immune System, British Journal of Pharmacology (2009) 158 638-651]. High levels of arginase have been found in patients with various cancers, including gastric, colon, breast and lung cancers [Suer et al (1999). Arginase and ornithine, as markers in human non-small cell lung carcinoma. Cancer Biochem Biophys 17:125-31; Singh et al (2000). Arginase activity in human breast cancer cell lines: N(omega)-hydroxy-L-arginine selectively inhibits cell proliferation and induces apoptosis in MDA-MB-468 cells. Cancer Res 60:3305-12].

As such, there is a need in the art for arginase inhibitors. The present invention addresses this need and provides related advantages as well.

BRIEF SUMMARY OF THE INVENTION

The present invention relates to compounds that inhibit arginase, and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by arginase. Such diseases, disorders and conditions are described in detail elsewhere herein. Unless otherwise indicated, when uses of the compounds of the present invention are described herein, it is to be understood that such compounds may be in the form of a composition (e.g., a pharmaceutical composition).

As discussed hereafter, although the compounds of the present invention are believed to effect their activity by inhibition of arginase, a precise understanding of the compounds' underlying mechanism of action is not required to practice the invention.

Arginase is an enzyme existing in mammals in two isoforms: ARG-1 is found in the cytosol and primarily expressed in the liver while ARG-2 is found in the mitochondria and expressed in the kidney, small intestine, brain, monocytes and macrophages. Arginase catalyzes the conversion of the amino acid L-arginine to ornithine and urea, which is an important precursor to downstream metabolic pathways allowing for tissue regeneration, cell proliferation and anti-inflammatory responses. L-arginine can also be metabolized by nitric oxide synthase (NOS), resulting in nitric oxide, a highly reactive compound important in the cytotoxic mechanism of macrophages. ARG-1 is believed to be preferentially expressed in myeloid-derived suppressor cells (MDSC) infiltrating tumors, resulting in a depletion of arginine from the tumor microenvironment. This depletion further results in a loss of expression of the TCR zeta chain, the principal signal-transduction element of the TCR, causing impaired proliferation and decreased cytokine production. As such, certain embodiments of the present invention provide compounds and methods of treating cancer by increasing arginine levels in a tumor microenvironment, thereby allowing activation of the body's cytotoxic T cells. See, Timosenko, Modulation of cancer-specific immune responses by amino acid degrading enzymes. Immunotherapy (2017) 9(1), 83-97.

In one particular aspect, the present invention provides compounds having Formula (I):

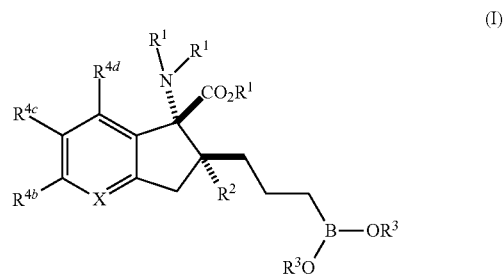

or a pharmaceutically acceptable salt, hydrate, or solvate thereof, wherein,

X is N or $CR^{4a}$;

each $R^1$ is independently H or $C_{1-8}$ alkyl;

$R^2$ is H or $CH_3$;

each $R^3$ is independently H or $C_{1-8}$ alkyl; or two $R^3$ groups are joined together to form a 5 or 6-membered ring which is unsubstituted or substituted with from 1 to 4 $R^a$;

each $R^{4a}$, $R^{4b}$, $R^{4c}$ and $R^{4d}$ is independently selected from the group consisting of H, halogen, CN, $C_{1-8}$ alkyl, $C_{1-8}$ alkoxy, $C_{1-8}$ hydroxyalkyl, $C_{1-8}$ haloalkyl, $C_{1-8}$ haloalkoxy, —$X^1$—Y, —$X^1$—$SO^2R^{5a}$ and —$X^1$—$NR^{5b}R^{5c}$;

each $R^{5a}$, $R^{5b}$ and $R^{5c}$ is independently selected from the group consisting of H, $C_{1-8}$ alkyl, $C_{1-8}$ haloalkyl, $C_{1-8}$ alkylC(O)—, $C_{3-7}$ cycloalkyl, 3- to 7-membered heterocycloalkyl, aryl, heteroaryl and an amino acid, or $R^{5b}$ and $R^{5c}$ are joined together to form a 4- to 6-membered ring; and wherein each of the 4- to 6-membered ring, $C_{3-7}$ cycloalkyl or 3- to 7-membered heterocycloalkyl, aryl and heteroaryl, are unsubstituted or substituted with from 1 to 4 $R^b$;

each $X^1$ is a bond, —O—, $C_{1-6}$ alkylene or —O—$C_{1-6}$ alkylene, wherein the alkylene portions are unsubstituted or substituted with 1 to 4 $R^c$ and 0 or 1 oxo;

each $R^a$, $R^b$ and $R^c$ is independently halogen, CN, OH, $NH_2$, $CO_2H$, $C_{1-4}$ alkyl, $C_{1-4}$ haloalkyl, $C_{3-6}$ cycloalkyl and phenyl, or two RC are combined to form a $C_{3-6}$ cycloalkyl which is unsubstituted or substituted with 1 to 3 $R^d$;

each Y is independently phenyl, a 5- or 6-membered heteroaryl, 3- to 7-membered heterocycloalkyl, or $C_{3-6}$ cycloalkyl, each of which is unsubstituted or substituted with from 1 to 3 $R^d$; and each $R^d$ is independently halogen, $C_{1-4}$ alkyl, amino, amino $C_{1-4}$ alkyl, $C_{1-4}$ haloalkyl, OH, and $C_{1-4}$ hydroxyalkyl.

In some embodiments, the present invention contemplates methods for treating or preventing cancer in a subject (e.g., a human) comprising administering to the subject a therapeutically effective amount of at least one arginase inhibitor described herein. In some embodiments, the present invention includes methods of treating or preventing a cancer in a subject by administering to the subject at least one of the compounds described herein in an amount effective to reverse, stop or slow the progression of arginase-mediated immunosuppression. In some embodiments, the arginase-mediated immunosuppression is mediated by a myeloid-derived suppressor cell (MDSC).

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell lung carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer or Kaposi's sarcoma. Cancers that are candidates for treatment with the compounds and compositions of the present invention are discussed further hereafter.

The present invention contemplates methods of treating a subject receiving a bone marrow transplant or peripheral blood stem cell transplant by administering a therapeutically effective amount of an arginase inhibitor.

In certain embodiments, the present invention contemplates methods for treating or preventing an infective disorder (e.g., a viral infection) in a subject (e.g., a human) comprising administering to the subject a therapeutically effective amount of at least one arginase inhibitor (e.g., a novel inhibitor of the instant invention). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, the present invention contemplates methods for treating or preventing an immune-related disease, disorder or condition in a subject (e.g., a human), comprising administering to the subject a therapeutically effective amount of at least one arginase inhibitor described herein. Examples of immune-related diseases, disorders and conditions are described hereafter.

Other diseases, disorders and conditions that can be treated or prevented, in whole or in part, by modulation of arginase activity are candidate indications for the arginase inhibitor compounds of the present invention.

The present invention further contemplates the use of arginase inhibitors described herein in combination with one or more additional agents. The one or more additional agents may function through distinct mechanisms of action. In some embodiments, such agents comprise radiation (e.g., localized radiation therapy or total body radiation therapy) and/or other treatment modalities of a non-pharmacological nature. When combination therapy is utilized, the compound(s) described herein and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In particular embodiments, the present invention contemplates the use of arginase inhibitors described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM doamins); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one arginase inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin, carboplatin and oxaliplatin; bioreductive alkylators such as mitomycin, procarbazine, dacarbazine and altretamine); anthracycline-based therapies (e.g., doxorubicin, daunorubicin, epirubicin and idarubicin); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the arginase inhibitors in combination with other agents known in the art (e.g., arsenic trioxide) and other chemotherapeutic agents developed in the future.

In some embodiments drawn to methods of treating cancer, the administration of a therapeutically effective amount of an arginase inhibitor described herein in combination with at least one chemotherapeutic agent results in a cancer survival rate greater than the cancer survival rate observed by administering either alone. In further embodiments drawn to methods of treating cancer, the administration of a therapeutically effective amount of an arginase inhibitor described herein in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a therapeutically effective amount of at least one arginase inhibitor described herein and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an arginase inhibitor in conjunction with at least one chemotherapeutic agent and/or radiation therapy, wherein the resulting rejection of tumor cells is greater than that obtained by administering either the arginase inhibitor, the chemotherapeutic agent or the radiation therapy alone.

In further embodiments, the present invention provides methods for treating cancer in a subject, comprising administering to the subject a therapeutically effective amount of at least one arginase inhibitor and at least one immunomodulator other than an arginase inhibitor. In particular embodiments, the at least one immunomodulator is selected from the group consisting of CD4OL, B7, B7RP1, anti-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-a/-13, M-CSF, IL-3, GM-CSF, IL-13, anti-IL-10, indoleamine 2,3-dioxygenase 1 (IDO1) inhibitors and adenosine 2 receptor antaogonists. Other candidate immunomodulator agents are set forth elsewhere herein.

The present invention contemplates embodiments comprising methods for treating or preventing an infective disorder (e.g., a viral infection) in a subject (e.g., a human) comprising administering to the subject a therapeutically effective amount of at least one arginase inhibitor described herein and a therapeutically effective amount of an anti-infective agent(s)

In some embodiments of the present invention, the additional therapeutic agent is a cytokine, including, for example granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Ban virus (EBV), varicella zoster virus, coxsackie virus, and human immunodeficiency virus (HIV). The use of the compounds described herein to treat (either alone or as a component of combination therapy) infection is discussed further hereafter.

In additional embodiments, treatment of an infective disorder is effected through the co-administration of a vaccine in combination with administration of a therapeutically effective amount of an arginase inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In some embodiments, the present invention contemplates methods of using the compounds described herein in combination with one or more antimicrobial agents.

In certain embodiments drawn to treatment of an infection by administering an arginase inhibitor and at least one additional therapeutic agent, a symptom of infection observed after administering both the arginase inhibitor and the additional therapeutic agent is improved over the same symptom of infection observed after administering either alone. In some embodiments, the symptom of infection observed can be reduction in viral load, increase in $CD4^+$ T cell count, decrease in opportunistic infections, increased survival time, eradication of chronic infection, or a combination thereof.

BRIEF DESCRIPTION OF THE DRAWINGS

NOT APPLICABLE

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Provided herein, for example, are compounds and compositions for inhibition of the arginase, and pharmaceutical compositions comprising the same. Also provided herein are, for example, methods of treating or preventing a disease, disorder or condition, or a symptom thereof, mediated by inhibition of arginase.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups, often referred to as $X^1$ groups in the present application, can be substituted or unsubstituted. When a group comprising $X^1$ is optionally substituted, it is understood that the optional substitutions may be on the alkylene portion of the moiety.

As used herein, a wavy line, "∼", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O) NH—" is meant to include a linkage in either orientation: —C(O)NH— or —NHC(O)—, and similarly, "—O—$CH_2CH_2$—" is meant to include both —O—$CH_2CH_2$— and —$CH_2CH_2$—O—.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The above terms (e.g., "alkyl," and "aryl"), in some embodiments, will be optionally substituted. Selected substituents for each type of radical are provided below.

Optional substituents for the alkyl radicals (including those groups often referred to as alkylene, alkenyl, and alkynyl) can be a variety of groups selected from: halogen, —OR', —NR'R", —SR', —SiR'R"R''', —OC(O)R', —C(O) R', —$CO_2$R', —CONR'R", —OC(O)NR'R", —NR"C(O)R', —NR'—C(O)NR"R''', —NR"C(O)$_2$R', —NH—C ($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —CN (cyano), —$NO_2$, aryl, aryloxy, oxo, cycloalkyl and heterocycloalkyl in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for aryl groups are varied and are generally selected from: -halogen, —OR', —OC(O) R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R''', —NH—C ($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-6 carbon atoms.

Two of the substituents on adjacent atoms of the aryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CR$^f$R$^g$)$_r$—B—, wherein A and B are independently —CH$_2$—, —O—, —NH—, —S—, —S(O)—, —S(O)$_2$—, —S(O)$_2$NR'— or a single bond, r is an integer of from 1 to 3, and R$^f$ and R$^g$ are each independently H of halogen. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S.M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are described in more detail elsewhere herein.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of arginase, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of arginase or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an arginase inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an arginase inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of arginase, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Arginase and Inhibition Thereof

As set forth above, a precise understanding of the compounds' underlying mechanism of action by which the compounds of the present invention effect their activity is not required to practice the invention, the compounds (or a subset thereof) are believed to inhibit arginase Although the compounds of the invention are generally referred to herein as arginase inhibitors, it is to be understood that the term "arginase inhibitors" encompasses compounds that act individually through inhibition of arginase, but also act through additional mechanisms.

Identification of Arginase Inhibitors Possessing Desirable Characteristics

The present invention is drawn, in part, to the identification of inhibitors of the arginase with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may the "best-of-class" of current inhibitors) are indicative of the potential viability of such candidates.

Compounds of the Invention

Provided herein are compounds having Formula (I)

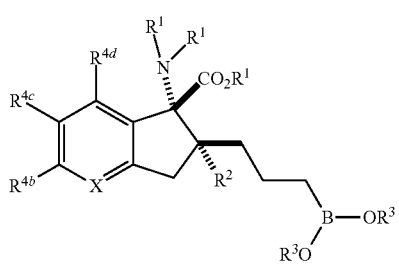

or a pharmaceutically acceptable salt, hydrate, or solvate thereof, wherein,

X is N or $CR^{4a}$;

each $R^1$ is independently H or $C_{1-8}$ alkyl;

$R^2$ is H or $CH_3$;

each $R^3$ is independently H or $C_{1-8}$ alkyl; or two $R^3$ groups are joined together to form a 5 or 6-membered ring which is unsubstituted or substituted with from 1 to 4 $R^a$;

each $R^{4a}$, $R^{4b}$, $R^{4c}$ and $R^{4d}$ is independently selected from the group consisting of H, halogen, CN, $C_{1-8}$ alkyl, $C_{1-8}$ alkoxy, $C_{1-8}$ hydroxyalkyl, $C_{1-8}$ haloalkyl, $C_{1-8}$ haloalkoxy, $-X^1-Y$, $-X^1-SO^2R^{5a}$ and $-X^1-NR^{5b}R^{5c}$;

each $R^{5a}$, $R^{5b}$ and $R^{5c}$ is independently selected from the group consisting of H, $C_{1-8}$ alkyl, $C_{1-8}$ haloalkyl, $C_{1-8}$ alkylC(O)—, $C_{3-7}$ cycloalkyl, 3- to 7-membered heterocycloalkyl, aryl, heteroaryl and an amino acid, or $R^{5b}$ and $R^{5c}$ are joined together to form a 4- to 6-membered ring; and wherein each of the 4- to 6-membered ring, $C_{3-7}$ cycloalkyl or 3- to 7-membered heterocycloalkyl, aryl and heteroaryl, are unsubstituted or substituted with from 1 to 4 $R^b$;

each $X^1$ is a bond, —O—, $C_{1-6}$ alkylene or —O—$C_{1-6}$ alkylene, wherein the alkylene portions are unsubstituted or substituted with 1 to 4 $R^c$ and 0 or 1 oxo;

each $R^a$, $R^b$ and $R^c$ is independently halogen, CN, OH, $NH_2$, $CO_2H$, $C_{1-4}$ alkyl, $C_{1-4}$ haloalkyl, $C_{3-6}$ cycloalkyl and phenyl, or two RC are combined to form a $C_{3-6}$ cycloalkyl which is unsubstituted or substituted with 1 to 3 $R^d$;

each Y is independently phenyl, a 5- or 6-membered heteroaryl, 3- to 7-membered heterocycloalkyl, or $C_{3-6}$ cycloalkyl, each of which is unsubstituted or substituted with from 1 to 3 $R^d$; and each $R^d$ is independently halogen, $C_{1-4}$ alkyl, amino, amino$C_{1-4}$ alkyl, $C_{1-4}$ haloalkyl, OH, and $C_{1-4}$ hydroxyalkyl.

In some embodiments the compounds of Formula (I), or a pharmaceutically acceptable salt, hydrate, or solvate thereof, are those compounds wherein:

X is N or $CR^{4a}$;

each $R^1$ is independently H or $C_{1-8}$ alkyl;

$R^2$ is H or $CH_3$;

each $R^3$ is independently H or $C_{1-8}$ alkyl; or two $R^3$ groups are joined together to form a 5 or 6-membered ring which is unsubstituted or substituted with from 1 to 4 $R^a$;

each $R^{4a}$, $R^{4b}$, $R^{4c}$ and $R^{4d}$ is independently selected from the group consisting of H, halogen, CN, $C_{1-8}$ alkyl, $C_{1-8}$ alkoxy, $C_{1-8}$ hydroxyalkyl, $C_{1-8}$ haloalkyl, $-X^1-Y$, $-X^1-SO^2R^{5a}$ and $-X^1-NR^{5b}R^{5c}$;

each $R^{5a}$, $R^{5b}$ and $R^{5c}$ is independently selected from the group consisting of H, $C_{1-8}$ alkyl, $C_{1-8}$ haloalkyl, $C_{1-8}$ alkylC(O)—, $C_{3-7}$ cycloalkyl, 3- to 7-membered heterocycloalkyl, aryl, heteroaryl and an amino acid, or $R^{5b}$ and $R^{5c}$ are joined together to form a 4- to 6-membered ring; and wherein each of the 4- to 6-membered ring, $C_{3-7}$ cycloalkyl or 3- to 7-membered heterocycloalkyl, aryl and heteroaryl, are unsubstituted or substituted with from 1 to 4 $R^b$;

each $X^1$ is a bond or $C_{1-6}$ alkylene which is unsubstituted or substituted with 1 to 4 $R^c$;

each $R^a$, $R^b$ and $R^c$ is independently halogen, CN, OH, $NH_2$, $C_{1-4}$ alkyl, $C_{1-4}$ haloalkyl, $C_{3-6}$ cycloalkyl and phenyl, or two $R^c$ are combined to form a $C_{3-6}$ cycloalkyl;

each Y is independently phenyl or a 5- or 6-membered heteroaryl, each of which is unsubstituted or substituted with from 1 to 3 $R^d$; and each $R^d$ is independently halogen, $C_{1-4}$ alkyl, amino, amino$C_{1-4}$ alkyl, $C_{1-4}$ haloalkyl, OH, and $C_{1-4}$ hydroxyalkyl.

In some embodiments of Formula (I), X is $CR^{4a}$. In other embodiments of Formula (I), X is N.

In some selected embodiments of Formula (I), and any of the embodiments discussed above, each $R^{4a}$, $R^{4b}$, $R^{4c}$ and $R^{4d}$ is independently selected from the group consisting of H, F, Cl, CN, $C_{1-4}$ alkyl, $C_{1-4}$ alkoxy, $C_{1-4}$ hydroxyalkyl, $C_{1-4}$ haloalkyl, $-X^1-Y$, $-X^1-SO^2R^{5a}$ and $-X^1-NR^{5b}R^{5c}$. In further embodiments, each $R^{4a}$, $R^{4b}$, $R^{4c}$ and $R^{4d}$ is independently selected from the group consisting of H, F, Cl, CN, $C_{1-4}$ alkyl, $C_{1-4}$ alkoxy, $C_{1-4}$ hydroxyalkyl, $C_{1-4}$ haloalkyl, and $-X^1-NR^{5b}R^{5c}$. In still further embodiments, each $R^{4a}$, $R^{4b}$, $R^{4c}$ and $R^{4d}$ independently selected from the group consisting of H, F, Cl, CN, $C_{1-4}$ alkyl, $C_{1-4}$ alkoxy, $C_{1-4}$ hydroxyalkyl, $C_{1-4}$ haloalkyl, and $-X^1-NR^{5b}R^{5c}$, and at least one of $R^{4a}$, $R^{4b}$, and $R^{4c}$ is $-X^1-NR^{5b}R^{5c}$. In yet further embodiments, $R^{4c}$ is $-X^1-NR^{5b}R^{5c}$.

In some selected embodiments of Formula (I), and any of the embodiments discussed above, each of $R^{5a}$, $R^{5b}$ and $R^{5c}$ is independently selected from the group consisting of H, $C_{1-4}$ alkyl, $C_{1-4}$ haloalkyl, $C_{1-4}$ alkylC(O)—, $C_{3-6}$ cycloalkyl, 3- to 6-membered heterocycloalkyl, phenyl, pyridyl, and an amino acid, or $R^{5b}$ and $R^{5c}$ are joined together to form a 4- to 6-membered ring; and wherein each of the 4- to 6-membered ring, $C_{3-6}$ cycloalkyl or 3- to 6-membered heterocycloalkyl, phenyl and pyridyl, are unsubstituted or substituted with from 1 to 4 $R^b$.

In some selected embodiments of Formula (I), and any of the embodiments discussed above, $X^1$ is a bond. In other selected embodiments of Formula (I), and any of the embodiments discussed above, $X^1$ is a methylene or ethylene group which is unsubstituted or substituted with 1 or 2 $R^c$. In still other selected embodiments of Formula (I), $X^1$ is methylene, ethylene,

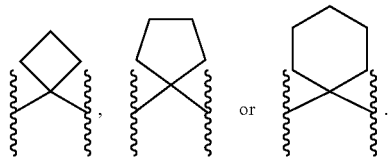

In some selected embodiments of Formula (I), and any of the embodiments discussed above, —$NR^{5b}R^{5c}$ is selected from the group consisting of —$NH_2$, —$NHCH_3$, —$N(CH_3)_2$, —$NHCH_2CF_3$, —$NHCH(CH_3)_2$, —$NHC(O)CH_3$,

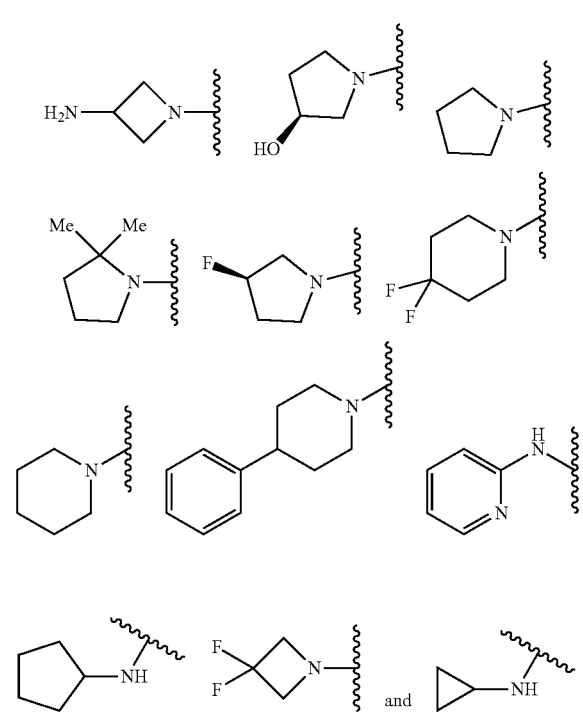

In some selected embodiments of Formula (I), and any of the embodiments discussed above, Y, when present, is selected from the group consisting of phenyl, pyridyl, pyrimidinyl, pyrazolyl, imidazolyl, 1,2,3-triazolyl, and 1,2,4-triazolyl, each of which is unsubstituted or substituted with from 1 to 3 $R^d$.

In one selected group of embodiments, compounds of Formula (I) are provided having the formula:

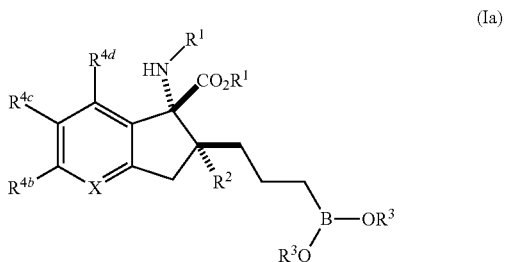
(Ia)

wherein each $R^1$, $R^2$, each $R^3$, $R^{4b}$, $R^{4c}$, $R^{4d}$ and X have the meanings provided with reference to Formula (I), or any of the embodiments provided above.

In another selected group of embodiments, compounds of Formula (I) are provided having the formula:

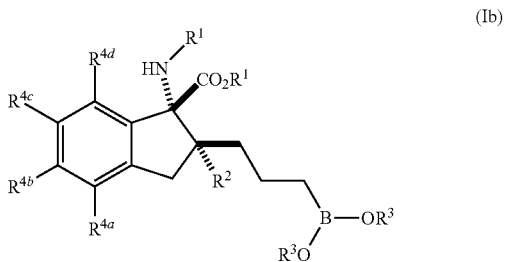
(Ib)

wherein each $R^1$, $R^2$, each $R^3$, $R^{4a}$, $R^{4b}$, $R^{4c}$, and $R^{4d}$ have the meanings provided with reference to Formula (I), or any of the embodiments provided above.

In another selected group of embodiments, compounds of Formula (I) are provided having the formula:

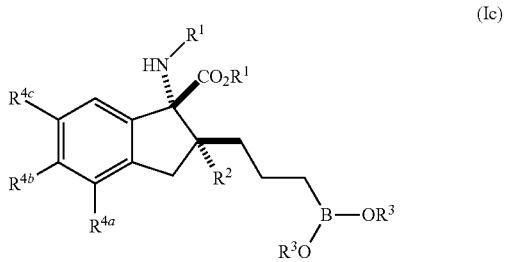
(Ic)

wherein each $R^1$, $R^2$, each $R^3$, $R^{4a}$, $R^{4b}$, and $R^{4c}$, have the meanings provided with reference to Formula (I), or any of the embodiments provided above.

In another selected group of embodiments, compounds of Formula (I) are provided having the formula:

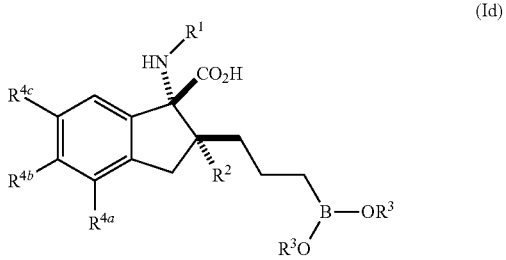
(Id)

wherein $R^1$, $R^2$, each $R^3$, $R^{4a}$, $R^{4b}$ and $R^{4c}$ have the meanings provided with reference to Formula (I), or any of the embodiments provided above.

In still other selected embodiments, compound of Formula (I) are provided having the formula:

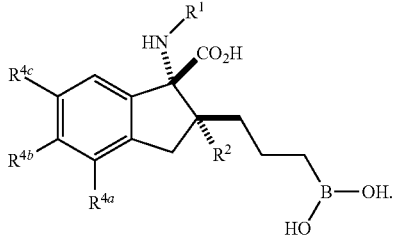
(Ie)

wherein $R^1$, $R^2$, $R^{4a}$, $R^{4b}$, and $R^{4c}$ have the meanings provided with reference to Formula (I), or any of the embodiments provided above.

In some selected embodiments, compounds of Formula (I) are provided having the formula:

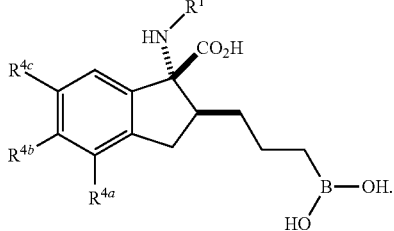
(If)

wherein $R^1$, $R^{4a}$, $R^{4b}$, and $R^{4c}$ have the meanings provided with reference to Formula (I), or any of the embodiments provided above.

In still other selected embodiments, compounds of Formula (I) are provided having the formula:

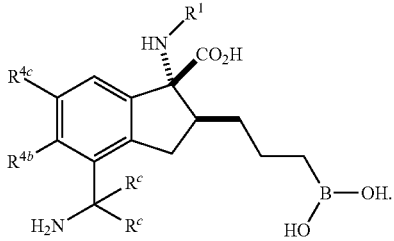
(Ig)

wherein $R^1$, each $R^c$, $R^{4b}$, and $R^{4c}$, have the meanings provided with reference to Formula (I), or any of the embodiments provided above.

In still other selected embodiments, compounds of Formula (I) are provided having the formula:

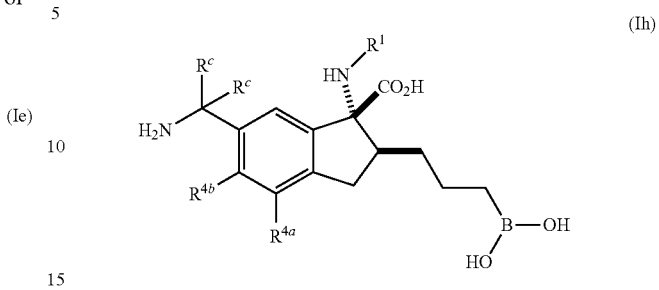
(Ih)

wherein $R^1$, each $R^c$, $R^{4a}$, and $R^{4b}$, have the meanings provided with reference to Formula (I), or any of the embodiments provided above.

In some selected embodiments, the compound of Formula (I) has the formula:

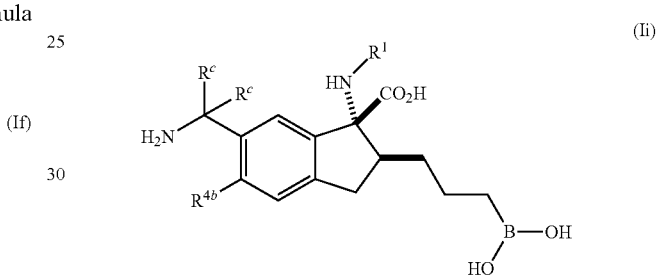
(Ii)

wherein $R^1$, each $R^c$, and $R^{4b}$ have the meanings provided with reference to Formula (I), or any of the embodiments provided above.

In further selected embodiments of formula (Ii), $R^{4b}$ is selected from the group consisting of H, $CH_3$, CN, $CF_3$, F and Cl.

In some selected embodiments, the compound of Formula (I) has the formula:

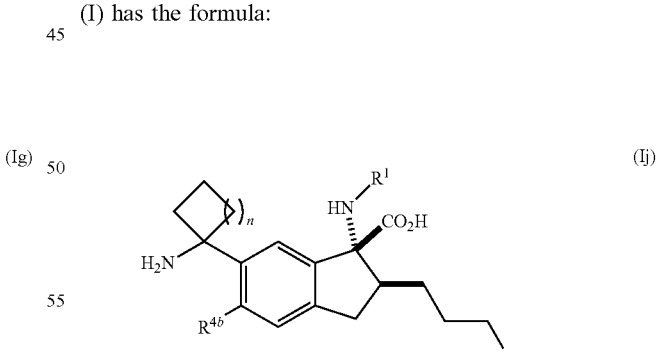
(Ij)

wherein the subscript n is 1, 2, or 3, and $R^1$ and $R^{4b}$ have the meanings provided with reference to Formula (I), or any of the embodiments provided above.

In some selected embodiments, the compound of Formula (I) has the formula:

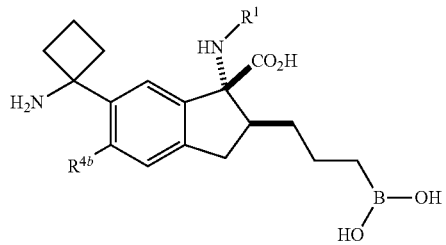

(Ik)

wherein $R^1$ and $R^{4b}$ have the meanings provided with reference to Formula (I), or any of the embodiments provided above.

In some selected embodiments, the compound of Formula (I) has a formula selected from the group consisting of:

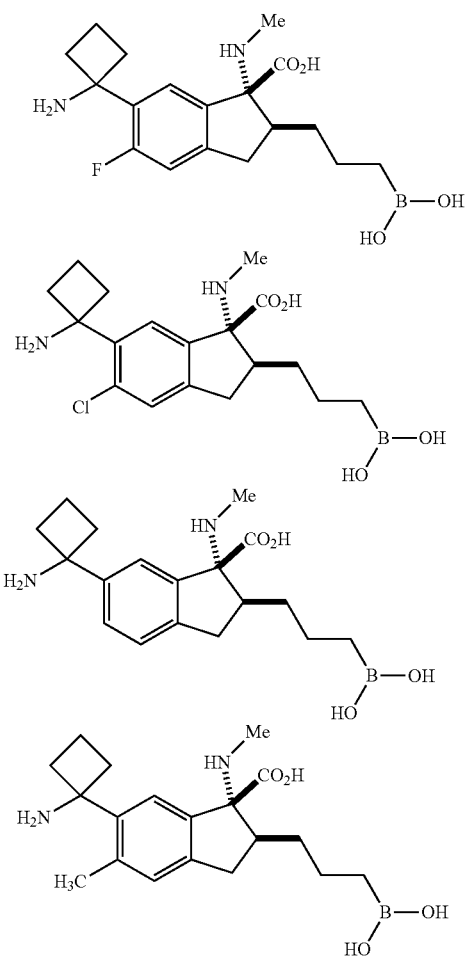

In some selected embodiments, any one compound of Table 1 is provided.

In some selected embodiments, deuterated forms of the compounds of Formula (I) are provided. Deuterium may be independently substituted for hydrogen at any position where hydrogen may be present.

Methods of Synthesis

In general, the compounds provided herein can be prepared by conventional methods as described in the Examples below.

Prodrugs and Other Means of Drug Delivery and/or Half-Life Extension

In some aspects of the present invention, compounds described herein are administered in prodrug form.

In order to effect extension of therapeutic activity, drug molecules may be engineered to utilize carriers for delivery. Such carriers are either used in a non-covalent fashion, with the drug moiety physicochemically formulated into a solvent-carrier mixture, or by permanent covalent attachment of a carrier reagent to one of the drug moiety's functional groups (see generally WO 20150202317).

Several non-covalent approaches are favored. By way of example, but not limitation, in certain embodiments depot formulations comprising non-covalent drug encapsulation into polymeric carriers are employed. In such formulations, the drug molecule is combined with carrier material and processed such that the drug molecule becomes distributed inside the bulk carrier. Examples include microparticle polymer-drug aggregates (e.g., Degradex® Microspheres (Phosphorex, Inc.)), which are administered as an injectable suspension; polymer-drug molecule aggregates formulated as gels (e.g., Lupron Depot® (AbbVie Inc.)), which are administered as a single bolus injection; and liposomal formulations (e.g., DepoCyt® (Pacira Pharmaceuticals)), where the carrier may be a polymeric or non-polymeric entity capable of solubilizing the drug. In these formulations, release of the drug molecule may occur when the carrier swells or physically deteriorates. In other instances, chemical degradation allows diffusion of the drug into the biological environment; such chemical degradation processes may be autohydrolytic or enzyme-catalyzed. Among other limitations, non-covalent drug encapsulation requires prevention of uncontrolled release of the drug, and dependence of the release mechanism of the drug upon biodegradation may cause interpatient variability.

In particular embodiments, drug molecules, including both small molecules and large molecules, are conjugated to a carrier through permanent covalent bonds. Certain small molecule therapeutics that exhibit low solubility in aqueous fluids may be solubilized by conjugation to hydrophilic polymers, examples of which are described elsewhere herein. Regarding large molecule proteins, half-life extension may be achieved by, for example, permanent covalent modification with a palmitoyl moiety, and by permanent covalent modification with another protein that itself has an extended half-life (e.g., Albuferon®). In general, drug molecules show decreased biological activity when a carrier is covalently conjugated to the drug.

In certain instances, limitations associated with either drug molecules comprising non-covalent polymer mixtures or permanent covalent attachment may be successfully addressed by employing a prodrug approach for chemical conjugation of the drug to the polymer carrier. In this context, therapeutic agents that are inactive or less active than the drug moiety itself are predictably transformed into active molecular entities. The reduced biological activity of the prodrug as compared to the released drug is advantageous if a slow or controlled release of the drug is desired. In such instances, release of the drug occurs over time, thereby reducing the necessity of repeated and frequent administration of the drug. A prodrug approach may also be advantageous when the drug moiety itself is not absorbed, or has less than optimal absorption, in the gastrointestinal tract;

in these instances, the prodrug facilitates absorption of the drug moiety and is then cleaved off at some later time (e.g., via first-pass metabolism). The biologically active drug molecule is typically linked to the polymeric carrier moiety by a temporary bond formed between the carrier moiety and a hydroxy, amino or carboxy group of the drug molecule.

The approaches described above are associated with several limitations. Prodrug activation may occur by enzymatic or non-enzymatic cleavage of the temporary bond between the carrier and the drug molecule, or a sequential combination of both (e.g., an enzymatic step followed by a non-enzymatic modification). In an enzyme-free in vitro environment (e.g., an aqueous buffer solution), a temporary bond such as an ester or amide may undergo hydrolysis, but the corresponding rate of hydrolysis may be such that it is outside the therapeutically useful range. In contrast, in an in vivo environment, esterases or amidases are typically present, and the esterases and amidases may cause significant catalytic acceleration of the kinetics of hydrolysis from two-fold up to several orders of magnitude (see, e.g., Greenwald et al., (1999) J Med Chem 42(18):3857-67).

As described herein, prodrugs may be classified as i) bioprecursors and ii) carrier-linked prodrugs. Bioprecursors do not contain a carrier group and are activated by the metabolic creation of a functional group. In contrast, in carrier-linked prodrugs the active substance is conjugated to a carrier moiety via a temporary linkage at a functional group of the bioactive entity. Preferred functional groups are hydroxyl or amino groups. Both the attachment chemistry and hydrolysis conditions depend on the type of functional group employed. The carrier may be biologically inert (e.g., PEG) or may have targeting properties (e.g., an antibody). Cleavage of the carrier moiety of a carrier-linked prodrug results in the bioactive entity of interest, and the nature of the deprotected functional group of the bioactive entity often contributes to its bioactivity.

The patent and scientific literature describe many macromolecular prodrugs where the temporary linkage is a labile ester bond. In these cases, the functional group of the bioactive entity is either a hydroxyl group or a carboxylic acid (see, e.g. Cheng et al. (2003) Bioconjugate Chem 14:1007-17). In addition, it is often advantageous for biomacromolecules and certain small molecule drugs to link the carrier to an amino group(s) of the bioactive entity (e.g., the N-terminus or lysine amino groups of proteins). During preparation of the prodrug, the amino groups may be more chemoselectively addressed due to their greater nucleophilicity compared to hydroxylic or phenolic groups. This is especially relevant for proteins and peptides containing a great variety of different reactive functionalities, where non-selective conjugation reactions lead to undesired product mixtures requiring extensive characterization or purification, thus decreasing reaction yield and therapeutic efficiency of the active moiety.

In general, amide bonds are more stable against hydrolysis than ester bonds, and the rate of cleavage of the amide bond may be too slow for therapeutic utility in a carrier-linked prodrug. As a result, it may be advantageous to add structural chemical components in order to effect control over the cleavability of the prodrug amide bond. These additional cleavage-controlling chemical components that are provided neither by the carrier entity nor by the drug are generally referred to as "linkers". Prodrug linkers can have a major effect on the rate of hydrolysis of temporary bond, and variation of the chemical nature of the linkers often results in particular properties. Prodrug activation of amine-containing biologically active moieties by specific enzymes for targeted release requires that the structure of the linker display a structural motif recognized as a substrate by a corresponding endogenous enzyme. In these cases, the cleavage of the temporary bond occurs in a one-step process which is catalyzed by the enzyme. For example, the enzymatic release of cytarabin is effected by the protease plasmin, which concentration is relatively high in various kinds of tumor mass.

Interpatient variability is a major drawback of predominant enzymatic cleavage. Enzyme levels may differ significantly between subjects resulting in biological variation of prodrug activation by the enzymatic cleavage. Enzyme levels may also vary depending on the site of administration (e.g., for subcutaneous injection, certain areas of the body yield more predictable therapeutic effects than others). In addition, it is difficult to establish an in vivo—in vitro correlation of the pharmacokinetic properties for enzyme-dependent carrier-linked prodrugs.

Other carrier prodrugs employing temporary linkages to amino groups in the drug moiety are based on a cascade mechanism. Cascade cleavage is enabled by linker compounds that are composed of a structural combination of a masking group and an activating group. The masking group is attached to the activating group by means of a first temporary linkage such as an ester or a carbamate. The activating group is attached to an amino group of the drug molecule through a second temporary linkage (e.g., a carbamate). The stability or susceptibility to hydrolysis of the second temporary linkage is dependent on the presence or absence of the masking group. In the presence of the masking group, the second temporary linkage is highly stable and unlikely to release the drug molecule with therapeutically useful kinetics, whereas in the absence of the masking group this linkage becomes highly labile, resulting in rapid cleavage and release of the drug moiety.

The cleavage of the first temporary linkage is the rate-limiting step in the cascade mechanism. The first step may induce a molecular rearrangement of the activating group (e.g., a 1,6-elimination as described in Greenwald et al. (1999) J Med Chem 42:3657-67), and the rearrangement renders the second temporary linkage much more labile such that its cleavage is induced. Ideally, the cleavage rate of the first temporary linkage is identical to the desired release rate for the drug molecule in a given therapeutic scenario. In addition, it is desirable that the cleavage of the second temporary linkage be substantially instantaneous after its lability has been induced by cleavage of the first temporary bond.

Another embodiment comprises polymeric amino-containing prodrugs based on trimethyl lock lactonization (see, e.g., Greenwald et al. (2000) J Med Chem 43(3):457-87). In this prodrug system, substituted o-hydroxyphenyl-dimethylpropionic acid is linked to PEG by an ester, carbonate, or carbamate group as a first temporary linkage and to an amino group of a drug molecule by means of an amide bond as a second temporary linkage. The rate-determining step in drug release is the enzymatic cleavage of the first linkage, which is followed by fast amide cleavage by lactonization, releasing an aromatic lactone side product. The primary disadvantage of the prodrug systems described by Greenwald et al. is the release of highly reactive and potentially toxic aromatic small molecule side products like quinone methides or aromatic lactones after cleavage of the temporary linkage. The potentially toxic entities are released in a 1:1 stoichiometry with the drug and can assume high in vivo concentrations.

In certain embodiments of cascade prodrugs comprising aromatic activating groups based on 1,6-elimination, the masking group is structurally separate from the carrier. This may be effected by employing a stable bond between the polymer carrier and the activating group, wherein the stable bond does not participate in the cascade cleavage mechanism. If the carrier is not serving as a masking group and the activating group is coupled to the carrier by means of a stable bond, release of potentially toxic side products (such as the activating group) is avoided. The stable attachment of the activating group and the polymer also suppresses the release of drug-linker intermediates with undefined pharmacology.

A first example of the approach described in the preceding paragraph comprises a polymeric prodrug system based on a mandelic acid activating group (see, e.g., Shabat et al. (2004) Chem Eur J 10:2626-34). In this approach the masking group is linked to the activating group by a carbamate bond. The activating group is conjugated permanently to a polyacrylamide polymer via an amide bond. After enzymatic activation of the masking group by a catalytic antibody, the masking group is cleaved by cyclization and the drug is released; the activating group is still connected to the polyacrylamide polymer after drug release. A similar prodrug system is based on a mandelic acid activating group and an enzymatically cleavable ester-linked masking group (see, e.g., Lee et al. (2004) Angew Chem 116:1707-10).

When the aforementioned linkers are used, the 1,6-elimination step still generates a highly reactive aromatic intermediate. Even if the aromatic moiety remains permanently attached to the polymeric carrier, side reactions with potentially toxic by-products or immunogenic effects may result. Thus, it is advantageous to generate linker technologies for forming polymeric prodrugs of amine-containing active agents using aliphatic prodrug linkers that are not enzyme-dependent and do not generate reactive aromatic intermediates during cleavage. One such example uses PEG5000-maleic anhydride for the reversible modification of amino groups in tissue-type plasminogen activator and urokinase (see, e.g. (1987) Garman et al. FEBS Lett 223(2):361-65). Regeneration of functional enzyme from PEG-uPA conjugate upon incubation at pH 7.4 buffer by cleavage of the maleamic acid linkage follows first order kinetics with a half-life of roughly 6 hours. A disadvantage of the maleamic acid linkage is the lack of stability of the conjugate at lower pH values.

A further approach comprises a PEG cascade prodrug system based on N,N-bis-(2-hydroxyethyl)glycine amide (bicine) linker (see e.g. (2004) J Med Chem 47:726-34). In this system, two PEG carrier molecules are linked via temporary bonds to a bicine molecule coupled to an amino group of the drug molecule. The first steps in prodrug activation involves the enzymatic cleavage of the first temporary linkages connecting both PEG carrier molecules with the hydroxy groups of the bicine activating group. Different linkages between PEG and bicine result in different prodrug activation kinetics. The second step in prodrug activation involves the cleavage of the second temporary linkage connecting the bicine activating group to the amino group of the drug molecule. A disadvantage of this system is the slow hydrolysis rate of this second temporary bicine amide linkage, which results in the release of a bicine-modified prodrug intermediate that may show different pharmacokinetic, immunogenic, toxicity and pharmacodynamic properties as compared to the native parent drug molecule.

In particular embodiments, dipeptides are utilized for prodrug development for targeting or targeted transport as they are substrates for enzymes or biotransport systems. The non-enzymatic route for dipeptide prodrug formation, that is, the ability to undergo intramolecular cyclization to form the corresponding diketopiperazine (DKP) and release the active drug, is not well defined.

In some embodiments, dipeptides are attached to a drug moiety via ester bonds, as was described for dipeptide esters of the drug paracetamol (Gomes et al. (2005) Bio & Med Chem Lett). In this case, the cyclization reaction consists of a nucleophilic attack of the N-terminal amine of the peptide on the ester carbon atom to form a tetrahedral intermediate, which is followed by a proton transfer from the amine to the leaving group oxyanion with simultaneous formation of a peptide bond to give the cyclic DKP product and free drug. This method is applicable to hydroxyl-containing drugs in vitro but has been found to compete with enzymatic hydrolysis of the ester bond in vivo, as corresponding dipeptide esters released paracetamol at a much faster rate than in buffer (Gomes et al. (Molecules 12 (2007) 2484-2506). Susceptibility of dipeptide-based prodrugs to peptidases may be addressed by incorporating at least one non-natural amino acid in the dipeptide motif. However, endogenous enzymes capable of cleaving ester bonds are not limited to peptidases, and the enzyme-dependence of such prodrug cleavage still gives rise to unpredictable in vivo performance.

In some embodiments, enzyme-dependence is intentionally engineered into DKP prodrugs, such as where dipeptide ester prodrugs are formylated at the amino terminus of the dipeptide, and enzymatic deformylation is used to initiate diketopiperazine formation and subsequent cleavage of the ester-dipeptide bond, followed by release of the drug molecule (see, e.g., U.S. Pat. No. 7,163,923). By way of further example, an octapeptide is attached by an ester linkage to the 4-hydroxyl group of vinblastine and undergoes ester bond cleavage by DKP formation after specific enzymatic removal of the N-terminal hexapeptide (see Brady et al. (2002) J Med Chem 45:4706-15).

The scope of the DKP formation reaction has also been extended to amide prodrugs. By way of example, U.S. Pat. No. 5,952,294 describes prodrug activation using diketopiperazine formation for dipeptidyl amide prodrugs of cytarabine. In this case, the temporary linkage is formed between the carbonyl of a dipeptide and the aromatic amino group of cytarabine. However, it is unlikely that a slow-release effect can be achieved for such conjugates as there is no carrier or other half-life extending moiety or functionality present.

Dipeptide prodrugs comprising bioactive peptides such as GLP-1 capable of releasing the peptide through diketopiperazine formation of the dipeptidic extension have also been described (see, e.g., WO 2009/099763). The bioactive peptide moiety may include an additional PEG chain on one of its amino acid side chain residues to achieve extended circulation of the bioactive peptide. However, this approach is associated with several significant disadvantages. First, the PEG chain has to be linked to the peptide without compromising its bioactivity, which can be difficult to achieve for many peptide-based bioactive agents. Second, as the pegylated peptide itself is bioactive, the dipeptidic promoiety has an effect on the peptide's bioactivity and may negatively affect its receptor binding properties.

Specific exemplary technologies that may be used with the compounds of the present invention include those developed by ProLynx (San Francisco, CA) and Ascendis Pharma (Palo Alto, CA). The ProLynx technology platform utilizes sets of novel linkers that are pre-programmed to cleave at different rates to allow the controlled, predictable and sustained release of small molecules and peptides from circulating semi-solid macromolecular conjugates. The technology allows for maintenance of desired steady-state serum levels of therapeutic agents for weeks to months.

The Ascendis technology platform combines the benefits of prodrug and sustained release technologies to enhance the properties of small molecules and peptides. While in circulation, proprietary prodrugs release the unmodified active parent therapeutic agent at predetermined rates governed by physiological pH and temperature conditions. Because the therapeutic agent is released in its unmodified form, it retains its original mechanism of action.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (*J. Am. Chem. Soc.,* 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Other known modifications include deuteration to improve pharmacokinetics, pharmacodyanics and toxicity profiles. Due to the greater atomic mass of deuterium, cleavage of the carbon-deuterium bond requires more energy than the carbon-hydrogen bond. Because these stronger bonds are more difficult to break, the rate of drug metabolism is slower as compared to non-deuterated forms, which allows for less frequent dosing and may further reduce toxicities. (Charles Schmidt, *Nature Biotechnology,* 2017, 35(6): 493-494; Harbeson, S. and Tung, R., *Medchem News,* 2014(2): 8-22).

Therapeutic and Prophylactic Uses

The present invention contemplates the use of the arginase inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

In some embodiments, the diseases, disorders and/or conditions described herein are mediated, at least in part, by arginase.

In some embodiments, the arginase inhibitors described herein are administered in an amount effective to reverse, stop or slow the activity of arginase-mediated immunosuppression.

Oncology-related Disorders. In accordance with the present invention, an arginase inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates inhibiting arginase in order to reverse the depletion of arginine which starves T cells and prevents their activation and proliferation (Rodriguez et al (2004), Arginase I production in the tumor microenvironment by mature myeloid cells inhibits T-cell receptor expression and antigen-specific T-cell responses. *Cancer Res.* 64(16), 5839-5849). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer may be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an arginase inhibitor and at least one additional therapeutic or diagnostic agent, examples of which are set forth elsewhere herein.

Immune-and Inflammatory-related Disorders. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the arginase inhibitors described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The arginase inhibitors of the present invention can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The arginase inhibitors can also be used to stimulate the immune system of patients suffering from iatrogenically-induced immune suppression, including those who have undergone bone marrow transplants, chemotherapy, or radiotherapy.

In particular embodiments of the present disclosure, the arginase inhibitors are used to increase or enhance an immune response to an antigen by providing adjuvant activity. In a particular embodiment, at least one antigen or vaccine is administered to a subject in combination with at least one arginase inhibitor of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one arginase inhibitor of the present invention.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of arginase function may also play a role in immunologic tolerance and prevention of fetal rejection in utero.

In some embodiments, an arginase inhibitor described herein can be combined with an immunosuppressive agent to reduce the number of immune effector cells.

Some of the aforementioned diseases, disorders and conditions for which an arginase inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

Microbial-related Disorders. The present invention contemplates the use of the arginase inhibitors described herein in the treatment and/or prevention of any viral, bacterial, fungal, parasitic or other infective disease, disorder or condition for which treatment with an arginase inhibitor may be beneficial.

Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Further examples of such diseases and disorders include staphylococcal and streptococcal infections (e.g., Staphylococcus aureus and streptococcus sanguinis, respectively), leishmania, toxoplasma, trichomonas, giardia, Candida albicans, Bacillus anthracis, and Pseudomonas aeruginosa. In some embodiments, diseases or disorders include Mycobacterium infection (e.g., Mycobacterium leprae or Mycobacterium tuberculosis) or an infection caused by Listeria monocytogenes or Toxplasma gondii. Compounds of the invention can be used to treat sepsis, decrease or inhibit bacterial growth, and reduce or inhibit inflammatory cytokines.

Further embodiments contemplate the treatment of a parasitic infection including, but not limited to, Leishmania donovani, Leishmania tropica, Leishmania major, Leishmania aethiopica, Leishmania mexicana, Plasmodium falciparum, Plasmodium vivax, Plasmodium ovale, or Plasmodium malariae. Frequently, anti-parasitic therapy is administered prophylactically (e.g., before a subject travels to an area with a high frequency of parasitic infection).

Other Disorders. Embodiments of the present invention contemplate the administration of the arginase inhibitors described herein to a subject for the treatment or prevention of any other disorder that may benefit from at least some level of arginase inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

Pharmaceutical Compositions

The arginase inhibitors of the present invention may be in the form of compositions suitable for administration to a subject. In general, such compositions are "pharmaceutical compositions" comprising an arginase inhibitor(s) and one or more pharmaceutically acceptable or physiologically acceptable diluents, carriers or excipients. In certain embodiments, the arginase inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of arginase function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an arginase inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an arginase inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the arginase inhibitors disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the arginase inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The arginase inhibitors contemplated by the present invention may be in the form of any other suitable pharmaceutical composition (e.g., sprays for nasal or inhalation use) currently known or developed in the future.

Routes of Administration

The present invention contemplates the administration of arginase inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the arginase inhibitors disclosed herein over a defined period of time.

Particular embodiments of the present invention contemplate oral administration.

Combination Therapy

The present invention contemplates the use of arginase inhibitors alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the arginase inhibitors are administered or applied sequentially, e.g., where one agent is administered prior to one or more other agents. In other embodiments, the arginase inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The arginase inhibitors of the present invention may be used in combination with at least one other (active) agent in any manner appropriate under the circumstances. In one embodiment, treatment with the at least one active agent and at least one arginase inhibitor of the present invention is maintained over a period of time. In another embodiment, treatment with the at least one active agent is reduced or discontinued (e.g., when the subject is stable), while treatment with an arginase inhibitor of the present invention is maintained at a constant dosing regimen. In a further embodiment, treatment with the at least one active agent is reduced or discontinued (e.g., when the subject is stable), while treatment with an arginase inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the arginase inhibitor of the present invention is increased (e.g., higher dose, more frequent dosing or longer treatment regimen). In yet another embodiment, treatment with the at least one active agent is maintained and treatment with the arginase inhibitor of the present invention is reduced or discontinued (e.g., lower dose, less frequent dosing or shorter treatment regimen). In yet another embodiment, treatment with the at least one active agent and treatment with the arginase inhibitor of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with an arginase inhibitor and at least one additional therapeutic or diagnostic agent. In some embodiments, the additional therapeutic or diagnostic agent is radiation, an immunomodulatory agent or chemotherapeutic agent, or diagnostic agent. Suitable immunomodulatory agents that may be used in the present invention include CD4OL, B7, and B7RP1; activating monoclonal antibodies (mAbs) to stimulatory receptors, such as, ant-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, ILL IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present invention provides methods for tumor suppression of tumor growth comprising administration of an arginase inhibitor described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with the arginase inhibitors described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin;

anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises a chemotherapy regimen that includes one or more chemotherapeutic agents. In certain embodiments, combination therapy comprises administration of a hormone or related hormonal agent.

Additional treatment modalities that may be used in combination with an arginase inhibitor include radiotherapy, a monoclonal antibody against a tumor antigen, a complex of a monoclonal antibody and toxin, a T-cell adjuvant, bone marrow transplant, or antigen presenting cells (e.g., dendritic cell therapy), including TLR agonists which are used to stimulate such antigen presenting cells.

In certain embodiments, the present invention contemplates the use of the compounds described herein in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present invention contemplates the use of the compounds described herein in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

In certain embodiments, the present invention contemplates the use of the compounds described herein in combination with agents that modulate the level of adenosine. Such therapeutic agents may act on the ectonucleotides that catalyze the conversion of ATP to adenosince, including ectonucleoside triphosphate diphosphohydrolase 1 (ENTPD1, also known as CD39 or Cluster of Differentiation 39), which hydrolyzes ATP to ADP and ADP to AMP, and 5'-nucleotidase, ecto (NT5E or 5NT, also known as CD73 or Cluster of Differentiation 73), which converts AMP to adenosine. The enzymatic activities of CD39 and CD73 play strategic roles in calibrating the duration, magnitude, and chemical nature of purinergic signals delivered to various cells (e.g., immune cells). Alteration of these enzymatic activities can change the course or dictate the outcome of several pathophysiological events, including cancer, autoimmune diseases, infections, atherosclerosis, and ischemia-reperfusion injury, suggesting that these ecto-enzymes represent novel therapeutic targets for managing a variety of disorders.

Alternatively, such therapeutic agents can be adenosine 2 receptor ($A_2R$) antagonists. Adenosine can bind to and active four different G-protein coupled receptors: $A_1R$, $A_{2a}R$, $A_{2b}R$, and $A_3R$. The binding of adenosine to the $A_{2a}R$ receptor, which is expressed on T cells, natural killer cells and myeloid cells such as dendritic cells, leads to increased intracellular levels of cyclic AMP and the impairment of maturation and/or activation of such cells. This process significantly impairs the activation of the immune system against cancer cells. In addition, $A_{2a}R$ has been implicated in selectively enhancing anti-inflammatory cytokines, promoting the upregulation of PD-1 and CTLA-4, promoting the generation of LAG-3 and Foxp3+regulatory T cells, and mediating the inhibition of regulatory T cells. PD-1, CTLA-4 and other immune checkpoints which are discussed further herein. Combining A2R antagonists in the combinations described herein may provide at least an additive effect in view of their differing mechanisms of actions.

In certain embodiments, the present invention contemplates the use of the compounds described herein in combination with inhibitors of phosphatidylinositol 3-kinases (PI3Ks), particularly the PI3Kγ isoform. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T-cell responses leading to decreased cancer development and spread.

In certain embodiments, the present invention contemplates the use of the compounds described herein in combination with inhibitors of hypoxia-inducible factor (HIF). HIF transcription factors are integral to signalling pathways used to sense and respond to low oxygen levels. The microenvironment of solid tumors is known to be hypoxic and requires induction of genes associated with metabolism, growth, proliferation, and angiogenesis for tumor cells to survive and metastasize. In particular, the HIF-2α isoform has been correlated with cancer, inflammatory and immunomodulatory conditions.

Immune Checkpoint Inhibitors. The present invention contemplates the use of the inhibitors of arginase function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor—ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the inhibitors of arginase function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

In one aspect of the present invention, the claimed arginase inhibitors are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD4OL, OX-40, OX-40L, CD70, CD27L, CD30, CD3OL, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of the disclosed arginase inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX4OL, GITR, GITRL, CD70, CD27, CD40, DR3 and CD2. Other agents that can be combined with the arginase inhibitors of the present invention for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, W011/107553, W011/131407, W013/87699, W013/119716, W013/132044) or FPA-008 (W011/140249; W013169264; W014/036357).

In another aspect, the disclosed arginase inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; W02012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgGl, called AMP-224.

In another aspect, the immuno-oncology agent is a PD-L1 antagonist, such as an antagonistic PD-L1 antibody. Suitable PD-L1 antibodies include, for example, MPDL3280A (RG7446; W02010/077634), durvalumab (MEDI4736), BMS-936559 (W02007/005874), and MSB0010718C (W02013/79174).

In another aspect, the immuno-oncology agent is a LAG-3 antagonist, such as an antagonistic LAG-3 antibody. Suitable LAG3 antibodies include, for example, BMS-986016 (W010/19570, W014/08218), or IMP-731 or IMP-321 (W008/132601, W009/44273).

In another aspect, the immuno-oncology agent is a CD137 (4-1BB) agonist, such as an agonistic CD137 antibody.

Suitable CD137 antibodies include, for example, urelumab and PF-05082566 (W012/32433).

In another aspect, the immuno-oncology agent is a GITR agonist, such as an agonistic GITR antibody. Suitable GITR antibodies include, for example, BMS-986153, BMS-986156, TRX-518 (W006/105021, W009/009116) and MK-4166 (W011/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX4OL antagonist, such as an antagonistic OX40 antibody. Suitable OX4OL antagonists include, for example, RG-7888 (W006/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (W011/109400).

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with an arginase inhibitor and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the arginase inhibitors described herein include various supplements and herbs (e.g., garlic, policosanol, and guggul).

The present invention encompasses pharmaceutically acceptable salts, acids or derivatives of any of the above.

Immune- and Inflammatory-related Disorders. The present invention provides methods for treating and/or preventing immune-related diseases, disorders and conditions; and diseases, disorders and conditions having an inflammatory component; with an arginase inhibitor and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxicam), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the arginase inhibitors described herein include interferon-131a (AVONEX); interferon-131b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Microbial Diseases. The present invention provides methods for treating and/or preventing viral, bacterial, fungal and parasitic diseases, disorders and conditions, as well as disorders associated therewith, with an arginase inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an arginase inhibitor include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, http://en.wikipedia.org/wiki/Fusion_inhibitor ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the inhibitors of arginase function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the arginase inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as Streptococcus), while "broad-spectrum" agents have activity against a broader range of bacteria. The skilled artisan is aware of types of antibacterial agents that are appropriate for use in specific bacterial infections.

Embodiments of the present invention contemplate the use of the arginase inhibitors described herein in combination with agents useful in the treatment or prevention of fungal disorders. Antifungal agents include polyenes (e.g., amphotericin, nystatin, and pimaricin);

azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The arginase inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the arginase inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the arginase inhibitors contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired arginase inhibitor is contained in a "unit dosage form". The phrase "unit dosage form" refers to physically discrete units, each unit containing a predetermined amount of the arginase inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound described herein, and pharmaceutical compositions thereof. The kits are generally in the form of a physical structure housing various components, as described below, and may be utilized, for example, in practicing the methods described above.

A kit can include one or more of the compounds disclosed herein (provided in, e.g., a sterile container), which may be in the form of a pharmaceutical composition suitable for administration to a subject. The compounds described herein can be provided in a form that is ready for use (e.g., a tablet or capsule) or in a form requiring, for example, reconstitution or dilution (e.g., a powder) prior to administration. When the compounds described herein are in a form that needs to be reconstituted or diluted by a user, the kit may also include diluents (e.g., sterile water), buffers, pharmaceutically acceptable excipients, and the like, packaged with or separately from the compounds described herein. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

Experimental

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, CA); and DeCypher™ (TimeLogic Corp., Crystal Bay, NV).

The literature is replete with assays and other experimental techniques that can serve as a basis for evaluation of the compounds described herein. By way of example, mass spectrometry-based ligand binding assays (see, e.g., Massink, A. et al. Purinergic Signaling (2015) 11:581. https://doi.org/10.1007/s11302-015-9477-0; Dionisotti S. et al. J Pharmacol Exp Ther. (1996) 298:726-732) may be utilized to ascertain various properties of the compounds of the present invention.

Functional assays may also be employed to assess the compounds of the present invention.

EXAMPLES

General Methods:

Those skilled in the art will recognize that there are a variety of methods available to prepare molecules represented in the claims.

A variety of the methods described above have been used to prepare compounds of the invention, some of which are exemplified in the examples. Deuterated forms of the below examples can be synthesized by using appropriate deuterated intermediates.

Example 1: rac-(1R,2S)-1-Amino-4-(aminomethyl)-2[3-(dihydroxyboranyl)propyl]-2,3-dihydro-1H-indene-1-carboxylic acid

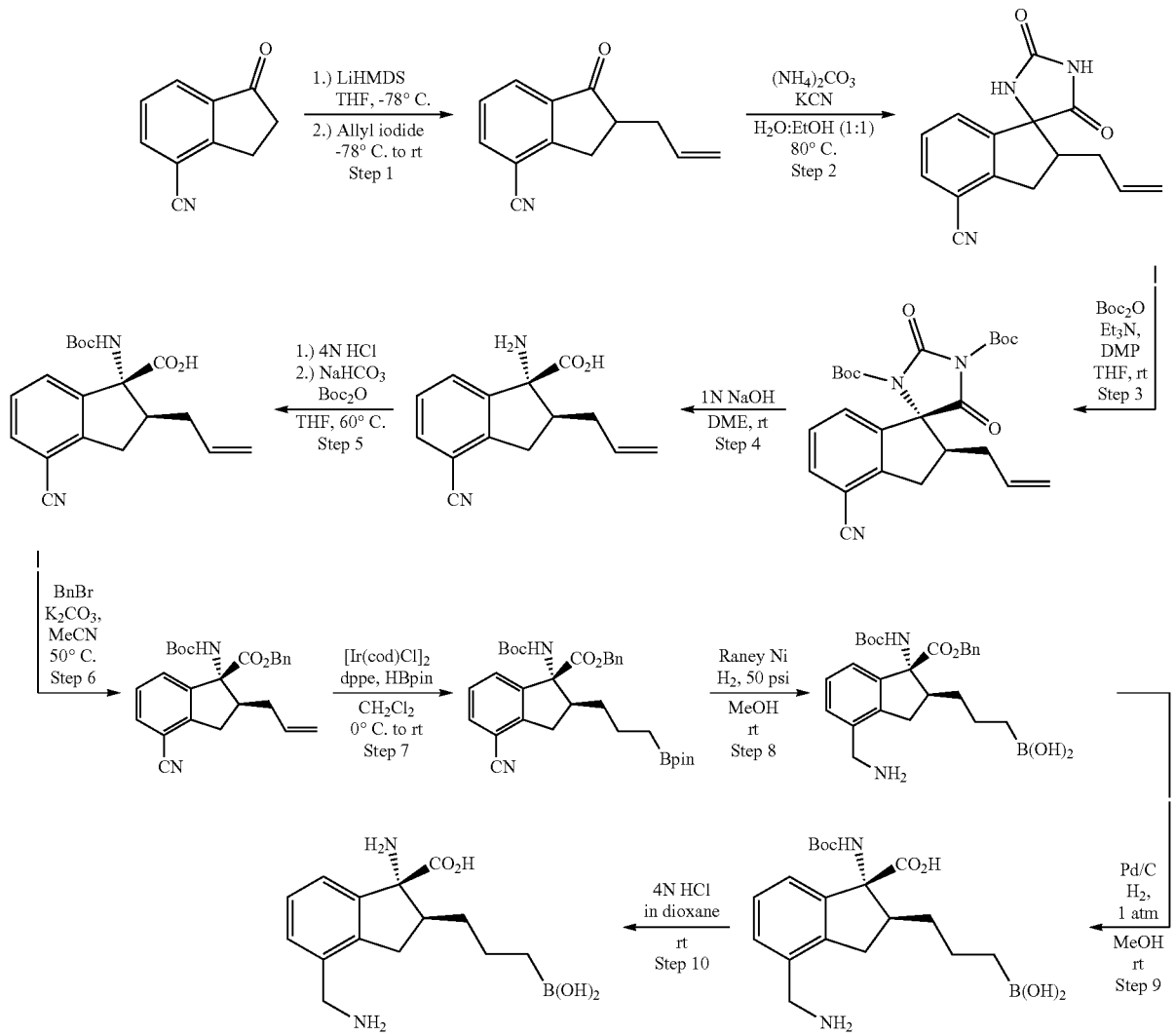

Step 1: To a suspension of 4-cyanoindanone (14.6 g, 93.3 mmol) in anhydrous THF (310 mL) at −78° C. was added LiHMDS (1M in THF, 93.3 mL) dropwise. The solution was stirred at −78° C. for 30 min. At this point, allyl iodide (17 mL, 186 mmol, 2 equiv.) was added slowly. The reaction was subsequently stirred at −78° C. for 3 h before gradually warmed up to room temperature overnight. Reaction was quenched by the addition of saturated NH$_4$Cl solution (70 mL) and H$_2$O (100 mL), followed by extraction into EtOAc (×2). The combined organic layer was washed with brine, dried over Na$_2$SO$_4$ and concentrated in vacuo to give a crude residue that was purified by column chromatography (silica gel, hex→10% EtOAc in hexanes) to afford the product as a yellow oil (5.75 g, 31%). ESI MS [M+H]$^+$ for C$_{13}$H$_{12}$NO, calcd 198.1, found 198.2.

Step 2: The product from Step 1 (5.75 g, 29 mmol) was dissolved in 50% aqueous ethanol (44 mL) and (NH$_4$)$_2$CO$_3$ (20 g, 115 mmol, 4 equiv.) followed by KCN (3.79 g, 58 mmol, 2 equiv.) were added. The reaction mixture was heated to 80° C. in a pressure tube for 36 h. After cooling to room temperature, 4N HCl was added slowly until pH 3 was reached. At this point, the crude reaction mixture was concentrated in vacuo and EtOAc (400 mL) was added. The organic layer was separated and the aqueous layer was re-extracted with EtOAc (300 mL). The combined organic layer was dried over Na$_2$SO$_4$ and concentrated in vacuo to give a crude residue that was purified by column chromatography (silica gel, hex→70% EtOAc in hexanes) to afford the desired product as a yellow oil (5.0 g, 1.5:1 dr, 64%). ESI MS [M+H]$^+$ for C$_{15}$H$_{14}$N$_3$O$_2$, calcd 268.1, found 268.0.

Step 3: To a solution of product from Step 2 (4.5 g, 1.5:1 dr, 16.8 mmol) in THF (125 mL) was added Et$_3$N (2.5 mL, 18.1 mmol, 1.1 equiv.) and Boc$_2$O (18.3 g, 83.9 mmol, 5 equiv.) followed by catalytic DMAP (0.41 g, 3.4 mmol, 20% mol.). The reaction mixture was stirred at room temperature for 16 h. At this point, the reaction mixture was concentrated in vacuo to give a crude residue that was purified by column chromatography (silica gel, hex→25% EtOAc in hexanes) to afford the desired diastereomer as a colorless oil (2.6 g, 33%). ESI MS [M−Boc+H]⁻ for $C_{20}H_{21}N_3O_4$, calcd 367.1, found 367.2.

Step 4: The product from Step 3 (2.6 g, 5.55 mmol) was dissolved in DME (50 mL) and 1N NaOH (50 mL). The reaction was stirred at room temperature for 1.5 h at which point the reaction was reduced in vacuo (to remove DME) and the resulting solution was washed with $CH_2Cl_2$ (15 mL). The aqueous layer was subsequently neutralized to pH 7 using 10N HCl and used in the next step without further purification. ESI MS [M+H]⁺ for $C_{14}H_{15}N_2O_2$, calcd 243.1, found 243.0.

Step 5: To the crude reaction mixture from Step 4 was added $NaHCO_3$ till pH 10, followed by THF (25 mL) and $Boc_2O$ (12.1 g, 55.5 mmol). The resulting mixture was heated to 60° C. for 16 h. The reaction mixture was cooled to room temperature, reduced in vacuo (to remove THF) and subsequently washed with $CH_2Cl_2$ (15 mL). The layers were separated and the aqueous layer was acidified to pH 3 prior to extraction into EtOAc (×3). The combined organic layer was washed with brine, dried over $Na_2SO_4$ and concentrated in vacuo to give a crude residue that was used in the next step without further purification. ESI MS [M−H]⁻ for $C_{19}H_{21}N_2O_4$, calcd 341.2, found 341.0.

Step 6: To a solution of the crude product from Step 5 in MeCN (6 mL) was added $Cs_2CO_3$ (1.53 g, 11.1 mmol) and BnBr (0.79 mL, 6.66 mmol). The reaction was heated to 50° C. for 1 h at which point solvent was concentrated in vacuo to give a crude residue that was purified by column chromatography (silica gel, hex→10% EtOAc in hexanes) to afford the desired product as a colorless oil (0.7 g, 30% over 2 steps). ESI MS [M−Boc+H₂]⁺ for $C_{21}H_{21}N_2O_2$, calcd 333.2, found 333.2.

Step 7: A solution of [Ir(cod)Cl]₂ (43.5 mg, 0.065 mmol, 4% mol.) and 1,2-bis(diphenylphosphino)ethane (51.8 mg, 0.13 mmol, 8% mol.) in degassed $CH_2Cl_2$ (3.2 mL) under a nitrogen atmosphere was stirred at room temperature for 30 min. At this point, the reaction was cooled to 0° C. and a solution of the product from Step 6 (700 mg, 1.62 mmol) in degassed $CH_2Cl_2$ (2.0 mL) was added, followed by dropwise addition of pinacolborane (0.35 mL, 2.4 mmol, 1.5 equiv.) and the reaction was immediately warmed up to room temperature and stirred for an additional 1.5 h. At this point, the reaction was quenched by dropwise addition of cold $H_2O$ (1 mL), followed by further addition of $H_2O$ (10 mL) and EtOAc (20 mL). The organic layer was separated, washed with brine, dried over $Na_2SO_4$ and concentrated in vacuo to give a crude residue that was purified by column chromatography (silica gel, hex→40% EtOAc in hexanes) to afford the desired product as a colorless oil (725 mg, 81%). ESI MS [M−Boc+H₂]⁺ for $C_{27}H_{34}BN_2O_4$, calcd 461.3, found 461.2.

Step 8: To a solution of product from Step 7 (210 mg, 0.38 mmol) in MeOH (3 mL) in a Parr shaker vessel was added Raney Ni (slurry in $H_2O$, 0.16 mL). The vessel was evacuated, refilled with $H_2$ (×3) and left on the Parr shaker ($H_2$ pressure: 50 psi) for 24 h. At this point, the reaction was carefully filtered over wet celite and the filter cake thoroughly washed with $CHCl_3$/EtOAc mixture. Solvent was concentrated in vacuo to give a crude residue that was purified by column chromatography (silica gel, $CH_2Cl_2$→15% MeOH in $CH_2Cl_2$, 1% vol $NH_4OH$ additive) to afford the desired product as a white foam (30 mg, 17%). ESI MS [M+H]⁺ for $C_{26}H_{36}BN_2O_6$, calcd 483.1, found 483.2.

Step 9: In a 40 mL scintillation vial fitted with a septum, the product from Step 8 (30 mg, 0.062 mmol) was dissolved in MeOH (3 mL) and the reaction was placed under an inert nitrogen atmosphere. Pd/C (10% wt, 16 mg) was added and the vial was evacuated and refilled with nitrogen (×3) prior to the introduction of $H_2$ (1 atm). The reaction was stirred at room temperature for 1 h. At this point, the reaction mixture was filtered by passing through a 0.45 μm syringe filter which was thoroughly washed with MeOH. Solvent was concentrated in vacuo to give the desired product as a white foam (24.3 mg, quant.). The product was used as is in the next step without further purification. ESI MS [M+H]⁺ for $C_{19}H_{30}BN_2O_6$, calcd 393.2, found 393.2.

Step 10: The product from Step 9 (24.3 mg, 0.062 mmol) was suspended in 4N HCl in dioxane (2 mL) and the reaction mixture was stirred at room temperature for 1 h. Solvent was removed in vacuo to give the title compound as a white solid (22.4 mg, quant.). ¹H NMR (400 MHz, D₂O) δ7.56-7.10 (m, 3H), 4.20 (s, 2H), 3.41-3.33 (m, 1H), 2.84-2.74 (m, 1H), 2.66-2.52 (m, 1H), 1.81-1.72 (m, 1H), 1.67-1.58 (m, 1H), 1.57-1.36 (m, 2H), 0.95-0.76 (m, 2H). ESI MS [M+H]⁺ for $C_{14}H_{22}BN_2O_4$, calcd 293.2, found 293.8.

Example 2: rac-(1R)-6-(Aminomethyl)-2-[3-(dihydroxyboranyl)propyl]-1-(methylamino)-2,3-dihydro-1H-indene-1-carboxylic acid

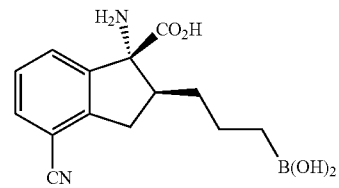 [SMILES: N#Cc1cccc2c1C[C@H](CCCB(O)O)[C@]2(N)C(=O)O]

The title compound was synthesized in similar fashion to Example 1. ¹H NMR (400 MHz, D₂O) δ7.68-7.65 (m, 2H), 7.43 (d, J=7.8 Hz, 1H), 3.29 (dd, J=16.8, 8.1 Hz, 1H), 2.81 (dd, J=16.7, 10.0 Hz, 1H), 2.69-2.56 (m, 1H), 1.69-1.57 (m, 1H), 1.54-1.41 (m, 1H), 1.34 (qd, J=12.9, 7.7 Hz, 2H), 0.70 (ddt, J=20.2, 15.4, 7.4 Hz, 2H). ESI MS [M+H]⁺ for $C_{14}H_{17}BN_2O_4$, calcd 289.1, found 289.0.

Example 3: rac-(1R,2S)-1-Amino-6-(aminomethyl)-2-[3-(dihydroxyboranyl)propyl]-2,3-dihydro-1H-indene-1-carboxylic acid

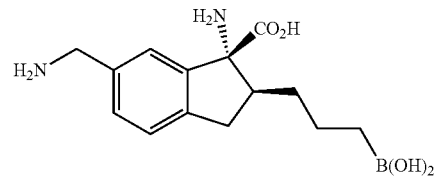 [SMILES: NCc1ccc2c(c1)[C@@](N)(C(=O)O)[C@@H](CCCB(O)O)C2]

The title compound was synthesized in similar fashion to Example 1. ¹H NMR (400 MHz, D₂O) δ7.42-7.40 (m, 2H), 7.36 (t, J=1.1 Hz, 1H), 4.16 (s, 2H), 3.31 (dd, J=16.0, 8.2 Hz, 1H), 2.79 (dd, J=16.0, 9.8 Hz, 1H), 2.65-2.52 (m, 1H), 1.79-1.67 (m, 1H), 1.60 (qt, J=12.0, 6.8 Hz, 1H), 1.54-1.37 (m, 2H), 0.91-0.75 (m, 2H). ESI MS [M+H]⁺ for $C_{14}H_{21}BN_2O_4$, calcd 293.2, found 293.2.

Example 4: rac-(1R,2S)-1-Amino-5-(aminomethyl)-2-[3-(dihydroxyboranyl)propyl]-2,3-dihydro-1H-indene-1-carboxylic acid

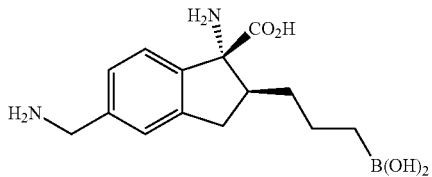 [SMILES: NCc1ccc2c(c1)C[C@H](CCCB(O)O)[C@]2(N)C(=O)O]

The title compound was synthesized in similar fashion to Example 1. $^1$H NMR (400 MHz, D$_2$O) δ7.29-7.23 (m, 2H), 7.22-7.12 (m, 1H), 4.03 (s, 2H), 3.17 (dd, J=16.0, 8.2 Hz, 1H), 2.68 (dd, J=16.0, 9.9 Hz, 1H), 2.58-2.35 (m, 1H), 1.69-1.53 (m, 1H), 1.53-1.40 (m, 1H), 1.39-1.21 (m, 2H), 0.71-0.65 (m, 2H). ESI MS [M+H]$^+$ for C$_{14}$H$_{22}$BN$_2$O$_4$, calcd 293.1, found 293.2.

Example 5: rac-(1R,2S)-1-Amino-2-[3-(dihydroxyboranyl)propyl]-6-methoxy-2,3-dihydro-1H-indene-1-carboxylic acid

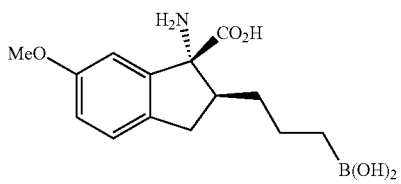 [SMILES: COc1ccc2c(c1)[C@@](N)(C(=O)O)[C@@H](CCCB(O)O)C2]

The title compound was synthesized in similar fashion to Example 1. $^1$H NMR (400 MHz, D$_2$O) δ7.29-7.25 (m, 1H), 6.99-6.93 (m, 2H), 3.80 (d, J=0.4 Hz, 3H), 3.21 (dd, J=15.3, 8.1 Hz, 1H), 2.70 (dd, J=15.2, 9.7 Hz, 1H), 2.59-2.49 (m, 1H), 1.72 (ddd, J=10.2, 8.0, 4.8 Hz, 1H), 1.64-1.50 (m, 1H), 1.50-1.35 (m, 2H), 0.83 (tq, J=15.1, 8.7, 7.5 Hz, 2H). ESI MS [M-(OH)$_2$]$^+$ for C$_{14}$H$_{20}$BNO$_5$, calcd 259.1, found 259.1.

Example 6: rac-(1R,2S)-1-Amino-6-chloro-2-[3-(dihydroxyboranyl)propyl]-2,3-dihydro-1H-indene-1-carboxylic acid

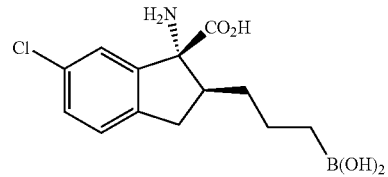

The title compound was synthesized in similar fashion to Example 1. $^1$H NMR (400 MHz, D$_2$O) δ6.93-6.91 (m, 1H), 6.90 (d, J=2.0 Hz, 1H), 6.84 (dd, J=8.0, 0.8 Hz, 1H), 2.80 (dd, J=14.9, 7.0 Hz, 1H), 2.33-2.16 (m, 2H), 1.29-1.16 (m, 1H), 1.13-1.00 (m, 1H), 1.00-0.84 (m, 2H), 0.40-0.20 (m, 2H). ESI MS [M+H]$^+$ for C$_{13}$H$_{17}$BClNO$_4$, calcd 298.1, found 298.0.

Example 7: (1R,2S)-1-Amino-2-[3-(dihydroxyboranyl)propyl]-2,3-dihydro-1H-indene-1-carboxylic acid

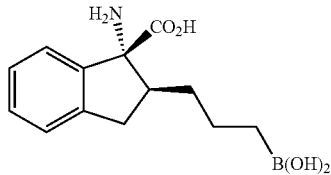 [SMILES: N[C@@]1(C(=O)O)c2ccccc2C[C@@H]1CCCB(O)O]

The title compound was synthesized in similar fashion to Example 1. $^1$H NMR (400 MHz, D$_2$O) δ7.39-7.25 (m, 4H), 3.27 (dd, J=15.8, 8.3 Hz, 1H), 2.77 (dd, J=15.8, 9.7 Hz, 1H), 2.58-2.46 (m, 1H), 1.78-1.66 (m, 1H), 1.66-1.53 (m, 1H), 1.53-1.37 (m, 2H), 0.91-0.72 (m, 2H). ESI MS [M+H]$^+$ for C$_{13}$H$_{18}$BNO$_4$, calcd 264.1, found 264.1.

Example 8: rac-(1R,2S)-4-(Aminomethyl)-2-[3-(dihydroxyboranyl)propyl]-1-(methylamino)-2,3-dihydro-1H-indene-1-carboxylic acid

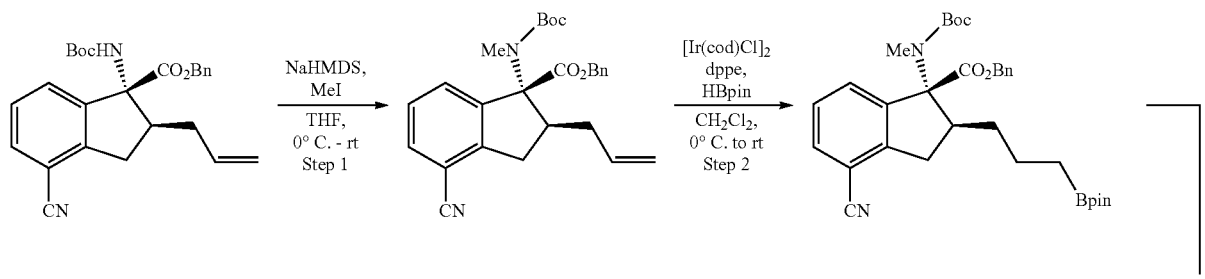

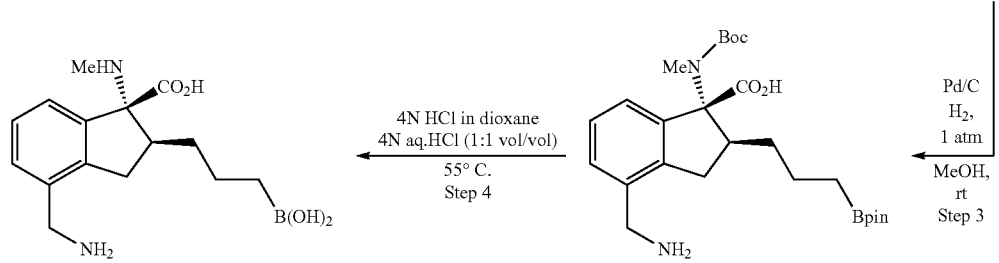

Step 1: To a suspension of benzyl ester (170 mg, 0.39 mmol) in anhydrous THF (1.7 mL) at 0° C. was added NaHMDS (1M in THF, 0.43 mL, 1.1 equiv.) dropwise. The solution was stirred at 0° C. for 15 min. At this point, iodomethane (50 μL, 0.79 mmol, 2 equiv.) was added slowly. The reaction was gradually warmed up to room temperature overnight. Reaction was quenched by the addition of saturated $NH_4Cl$ solution (10 mL), followed by extraction into EtOAc (2×20 mL). The combined organic layer was washed with brine, dried over $Na_2SO_4$ and concentrated in vacuo to give a crude residue that was purified by column chromatography (silica gel, hex→10% EtOAc in hexanes) to afford the desired product as a colorless oil (130 mg, 69%). ESI MS [M-Boc+H]$^+$ for $C_{22}H_{23}N_2O_2$, calcd 347.2, found 347.2.

Step 2: A solution of [Ir(cod)Cl]$_2$ (7.4 mg, 0.011 mmol, 4% mol.) and 1,2-bis(diphenylphosphino)ethane (8.7 mg, 0.022 mmol, 8% mol.) in degassed $CH_2Cl_2$ (0.8 mL) under a nitrogen atmosphere was stirred at room temperature for 30 min. At this point, the reaction was cooled to 0° C. and a solution of the product from Step 1 (130 mg, 0.27 mmol) in degassed $CH_2Cl_2$ (0.7 mL) was added, followed by dropwise addition of pinacolborane (80 μL, 0.55 mmol, 2 equiv.) and the reaction was immediately warmed up to room temperature and stirred for an additional 1.5 h. At this point, the reaction was quenched by dropwise addition of cold $H_2O$ (1 mL), followed by further addition of $H_2O$ (10 mL) and EtOAc (20 mL). The organic layer was separated, washed with brine, dried over $Na_2SO_4$ and concentrated in vacuo to give a crude residue that was purified by column chromatography (silica gel, hex→35% EtOAc in hexanes) to afford the desired product as a colorless oil (70 mg, 46%). ESI MS [M-Boc+H$_2$]$^+$ for $C_{28}H_{36}BN_2O_4$, calcd 475.3, found 475.3.

Step 3: In a 40 mL scintillation vial fitted with a septum, the product from Step 2 (70 mg, 0.013 mmol) was dissolved in MeOH (3 mL) and the reaction was placed under an inert nitrogen atmosphere. Pd/C (10% wt., 13 mg) was added and the vial was evacuated and refilled with nitrogen (×3) prior to the introduction of H$_2$ (1 atm). The reaction was stirred at room temperature for 16 h. At this point, the reaction mixture was filtered by passing through a 0.45 μm syringe filter which was thoroughly washed with MeOH. Solvent was concentrated in vacuo to give the desired product as a white foam (61 mg, quant.). The product was used as is in the next step without further purification. ESI MS [M-Boc+H]$^+$ for $C_{21}H_{34}BN_2O_4$, calcd 389.3, found 389.2.

Step 4: The product from Step 3 (61 mg, 0.013 mmol) was suspended in 4N HCl in dioxane (1.5 mL) and 4N aq. HCl. The reaction mixture was stirred at room temperature for 2.5 h. Solvent was removed in vacuo to a crude residue that was purified by RP-HPLC (0 to 10% gradient of acetonitrile and water) to give the desired product as a white solid (22 mg, 46%). $^1$H NMR (400 MHz, D$_2$O) δ7.53-7.22 (m, 3H), 4.20 (s, 2H), 3.49-3.40 (m, 1H), 2.97-2.67 (m, 2H), 2.51 (s, 3H), 1.75-1.55 (m, 2H), 1.56-1.37 (m, 2H), 0.90-0.74 (m, 2H). ESI MS [M-H]$^-$ for $C_{15}H_{22}BN_2O_4$, calcd 305.2, found 305.0.

Example 9: rac-(1R,2S)-5-(Aminomethyl)-2-[3-(dihydroxyboranyl)propyl]-1-(methylamino)-2,3-dihydro-1H-indene-1-carboxylic acid

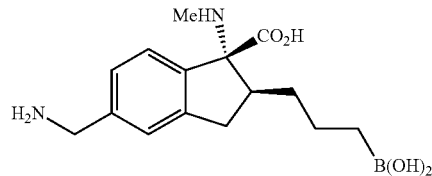 [SMILES: CN[C@@]1(C(=O)O)c2ccc(CN)cc2C[C@@H]1CCCB(O)O]

The title compound was synthesized in similar fashion to Example 8. $^1$H NMR (400 MHz, D$_2$O) δ7.27 (s, 1H), 7.21 (s, 2H), 4.03 (s, 2H), 3.27-3.17 (m, 1H), 2.67 (dd, J=15.8, 8.3 Hz, 1H), 2.62-2.53 (m, 1H), 2.36 (s, 3H), 1.58-1.39 (m, 2H), 1.38-1.23 (m, 2H), 0.77-0.58 (m, 2H). ESI MS [M+H]$^+$ for $C_{15}H_{24}BN_2O_4$, calcd 307.2, found 307.2.

Example 10: rac-(1R)-6-(Aminomethyl)-2-[3-(dihydroxyboranyl)propyl]-1-(methylamino)-2,3-dihydro-1H-indene-1-carboxylic acid

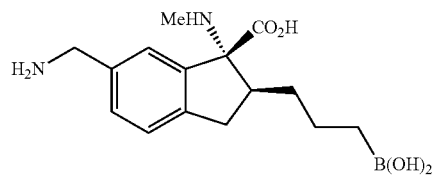 [SMILES: CN[C@@]1(C(=O)O)c2cc(CN)ccc2C[C@@H]1CCCB(O)O]

The title compound was synthesized in similar fashion to Example 8. $^1$H NMR (400 MHz, D$_2$O) δ7.44 (d, J=1.1 Hz, 2H), 7.33 (s, 1H), 4.17 (s, 2H), 3.37 (dd, J=16.2, 8.1 Hz, 1H), 2.81 (dd, J=16.1, 8.0 Hz, 1H), 2.75-2.66 (m, 1H), 2.51 (s, 3H), 1.70-1.52 (m, 2H), 1.53-1.35 (m, 2H), 0.82 (tt, J=15.8, 8.0 Hz, 2H). ESI MS [M+H]$^+$ for $C_{15}H_{24}BN_2O_4$, calcd 307.2, found 307.2.

Example 11: rac-(1R,2S)-2-[3-(Dihydroxyboranyl)
propyl]-1-(methylamino)-4-[(methylamino)methyl]-
2,3-dihydro-1H-indene-1-carboxylic acid

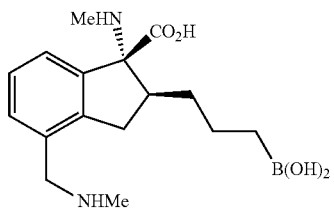 [SMILES: CNCc1cccc2c1C[C@H](CCCB(O)O)[C@]2(NC)C(=O)O]

The title compound was synthesized in similar fashion to Example 8. $^1$H NMR (400 MHz, CD$_3$OD) δ7.70-7.15 (m, 3H), 3.48-3.29 (m, 1H), 3.22-3.04 (m, 1H), 3.04-2.36 (m, 2H), 2.80-2.47 (m, 7H), 2.04-1.42 (m, 4H), 1.05-0.77 (m, 2H). ESI MS [M–H]$^-$ for C$_{16}$H$_{24}$BN$_2$O$_4$, calcd 319.1, found 319.2.

Example 12: rac-(1R,2S)-5-(Aminomethyl)-2-[3-(dihydroxyboranyl)propyl]-6-methoxy-1-(methyl-amino)-2,3-dihydro-1H-indene-1-carboxylic acid

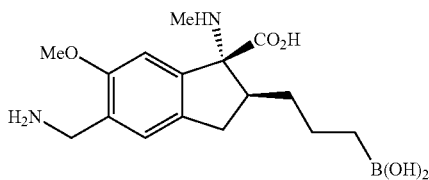 [SMILES: CN[C@@]1(C(=O)O)c2cc(OC)c(CN)cc2C[C@@H]1CCCB(O)O]

The title compound was synthesized in similar fashion to Example 8. $^1$H NMR (400 MHz, D$_2$O) δ7.14 (s, 1H), 6.81 (s, 1H), 4.09-3.89 (m, 2H), 3.70 (s, 3H), 3.25-3.00 (m, 1H), 2.68-2.41 (m, 2H), 2.35 (s, 3H), 1.49-1.36 (m, 2H), 1.38-1.17 (m, 2H), 0.81-0.53 (m, 2H). ESI MS [M+H]$^+$ for C$_{16}$H$_{26}$BN$_2$O$_5$, calcd 337.2, found 337.2.

Example 13: rac-(1R,2S)-5-(Aminomethyl)-6-
chloro-2-[3-(dihydroxyboranyl)propyl]-1-(methyl-
amino)-2,3-dihydro-1H-indene-1-carboxylic acid

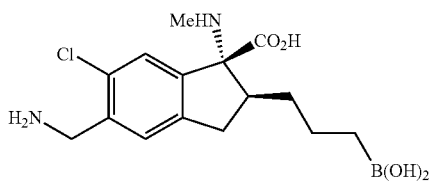 [SMILES: CN[C@@]1(C(=O)O)c2cc(Cl)c(CN)cc2C[C@@H]1CCCB(O)O]

The title compound was synthesized in similar fashion to Example 8. $^1$H NMR (400 MHz, D$_2$O) δ7.47 (s, 1H), 7.45 (s, 1H), 4.48-4.15 (m, 2H), 3.42-3.23 (m, 1H), 2.87-2.68 (m, 2H), 2.52 (s, 3H), 1.74-1.33 (m, 4H), 0.90-0.67 (m, 2H). ESI MS [M+H]$^+$ for C$_{15}$H$_{23}$BClN$_2$O$_4$, calcd 341.1, found 341.0.

Example 14: rac-(1R,2S)-1-Amino-6-(2-amino-
ethyl)-2-[3-(dihydroxyboranyl)propyl]-2,3-dihydro-
1H-indene-1-carboxylic acid

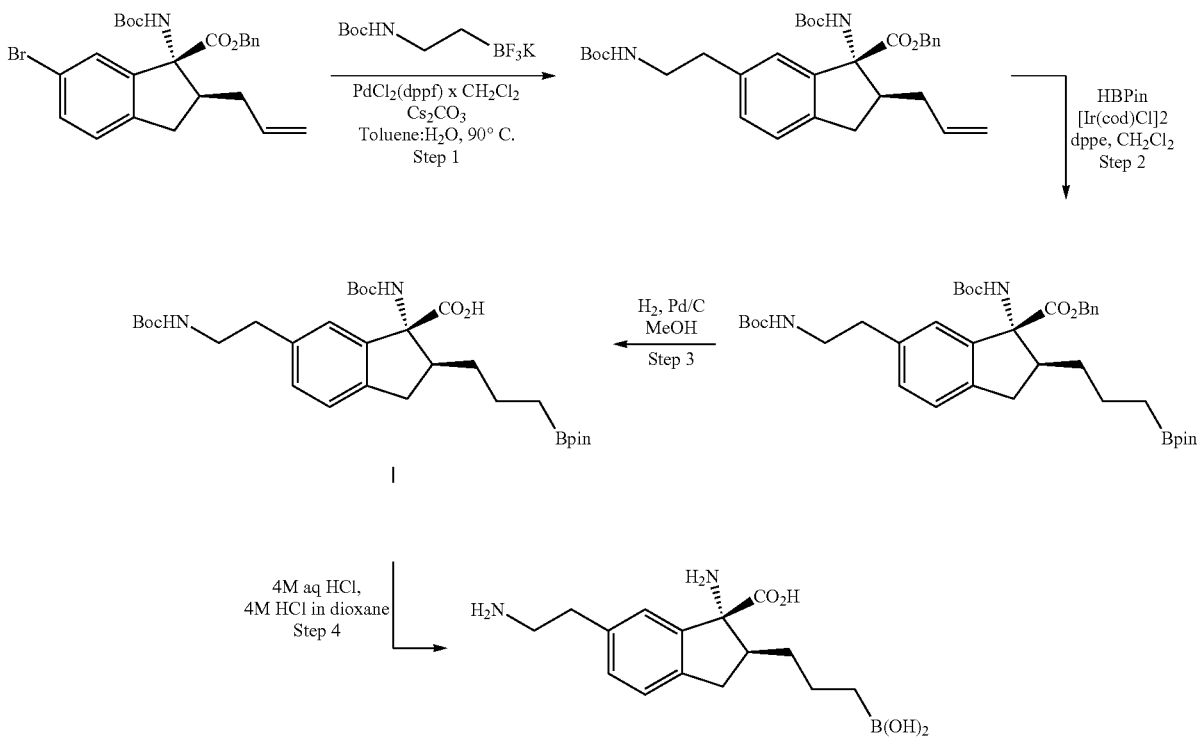

Step 1: A flame dried vial containing benzyl ester (365 mg, 0.75 mmol, 1.0 equiv.), trifluoroborate potassium salt (207 mg, 0.8 mmol, 1.1 equiv.), Pd(dppf)Cl$_2$×CH$_2$Cl$_2$ (31 mg, 0.04 mmol, 5% mol.) and Cs$_2$CO$_3$ (735 mg, 2.3 mmol, 3.0 equiv.) was purged with N$_2$ and diluted with degassed toluene (3.5 mL) and H$_2$O (1.2 mL). The resulted mixture was degassed with N$_2$ for 5 min and resulting reaction mixture was heated at 90° C. for 20 h. After cooling to room temperature, EtOAc (10 mL) and saturated, aqueous NH$_4$Cl (2 mL) were added. The organic layer was washed with brine (2 mL), dried over Na$_2$SO$_4$ and concentrated. The residue was purified by column chromatography (silica gel, 0→40% EtOAc in hexane) to afford the title compound as a white foam (263 mg, 64%).

Steps 2, 3 and 4 were carried out in a similar manner as for Example 8. $^1$H NMR (400 MHz, D$_2$O) δ7.34 (d, J=7.9 Hz, 1H), 7.27 (dd, J=7.8, 1.7 Hz, 1H), 7.22 (d, J=1.5 Hz, 1H), 3.32-3.19 (m, 3H), 2.97 (td, J=7.0, 3.8 Hz, 2H), 2.80-2.70 (m, 1H), 2.60-2.50 (m, 1H), 1.78-1.65 (m, 1H), 1.65-1.52 (m, 1H), 1.52-1.36 (m, 2H), 0.89-0.74 (m, 2H). ESI MS [M-OH]$^+$ for C$_{15}$H$_{23}$BN$_2$O$_4$, calcd 289.2, found 289.2.

Example 15: rac-(1R,2S)-1-Amino-5-(2-amino-ethyl)-2-[3-(dihydroxyboranyl)propyl]-2,3-dihydro-1H-indene-1-carboxylic acid

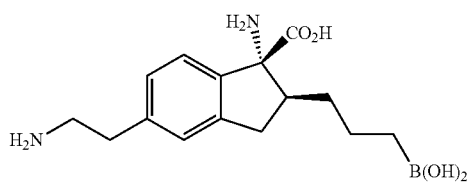 [SMILES: NCCc1ccc2c(c1)C[C@H](CCCB(O)O)[C@]2(N)C(=O)O]

The title compound was synthesized in similar fashion to Example 14. $^1$H NMR (400 MHz, D$_2$O) δ7.44-7.05 (m, 3H), 3.32-3.13 (m, 3H), 2.99 (t, J=7.2 Hz, 2H), 2.85-2.72 (m, 1H), 2.68-2.52 (m, 1H), 1.80-1.66 (m, 1H), 1.70-1.53 (m, 1H), 1.50-1.36 (m, 2H), 0.97-0.64 (m, 2H). ESI MS [M–H$_2$O+H]$^+$ for C$_{15}$H$_{22}$BN$_2$O$_3$, calcd 289.2, found 289.2.

Example 16: rac-(1R,2S)-1-Amino-6-(2-amino-ethyl)-5-chloro-2-[3-(dihydroxyboranyl)propyl]-2,3-dihydro-1H-indene-1-carboxylic acid

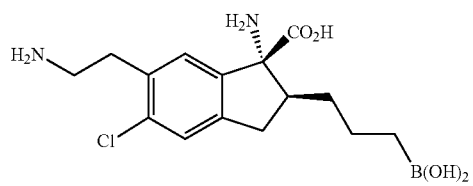 [SMILES: NCCc1cc2c(cc1Cl)C[C@H](CCCB(O)O)[C@]2(N)C(=O)O]

The title compound was synthesized in similar fashion to Example 14. $^1$H NMR (400 MHz, D$_2$O) δ7.47 (s, 1H), 7.30 (s, 1H), 3.34-3.14 (m, 4H), 3.10-3.00 (m, 1H), 2.85-2.74 (m, 1H), 2.61 (q, J=10.7, 9.4 Hz, 1H), 1.80-1.66 (m, 1H), 1.65-1.51 (m, 1H), 1.51-1.38 (m, 2H), 0.90-0.74 (m, 2H). ESI MS [M-(OH)]$^+$ for C$_{15}$H$_{22}$BClN$_2$O$_4$, calcd 323.1, found 323.0.

Example 17: (1R,2S)-6-(Aminomethyl)-5-chloro-2-[3-(dihydroxyboranyl)propyl]-1-(methylamino)-2,3-dihydro-1H-indene-1-carboxylic acid

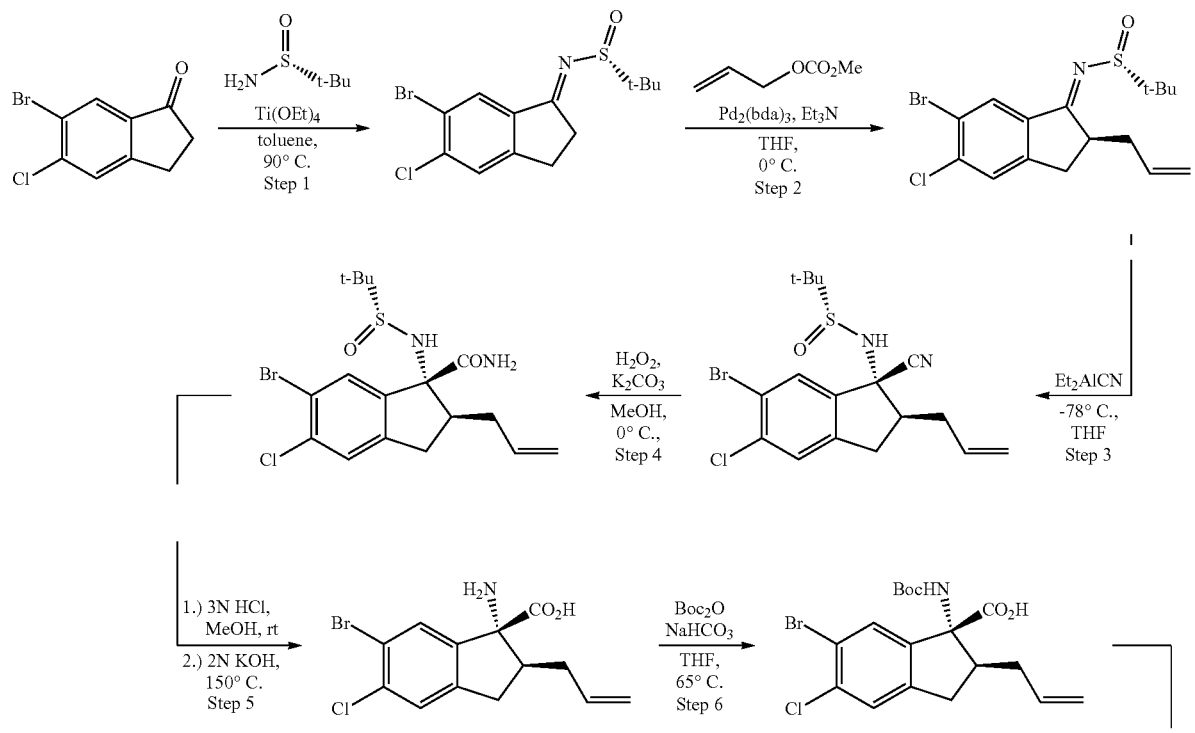

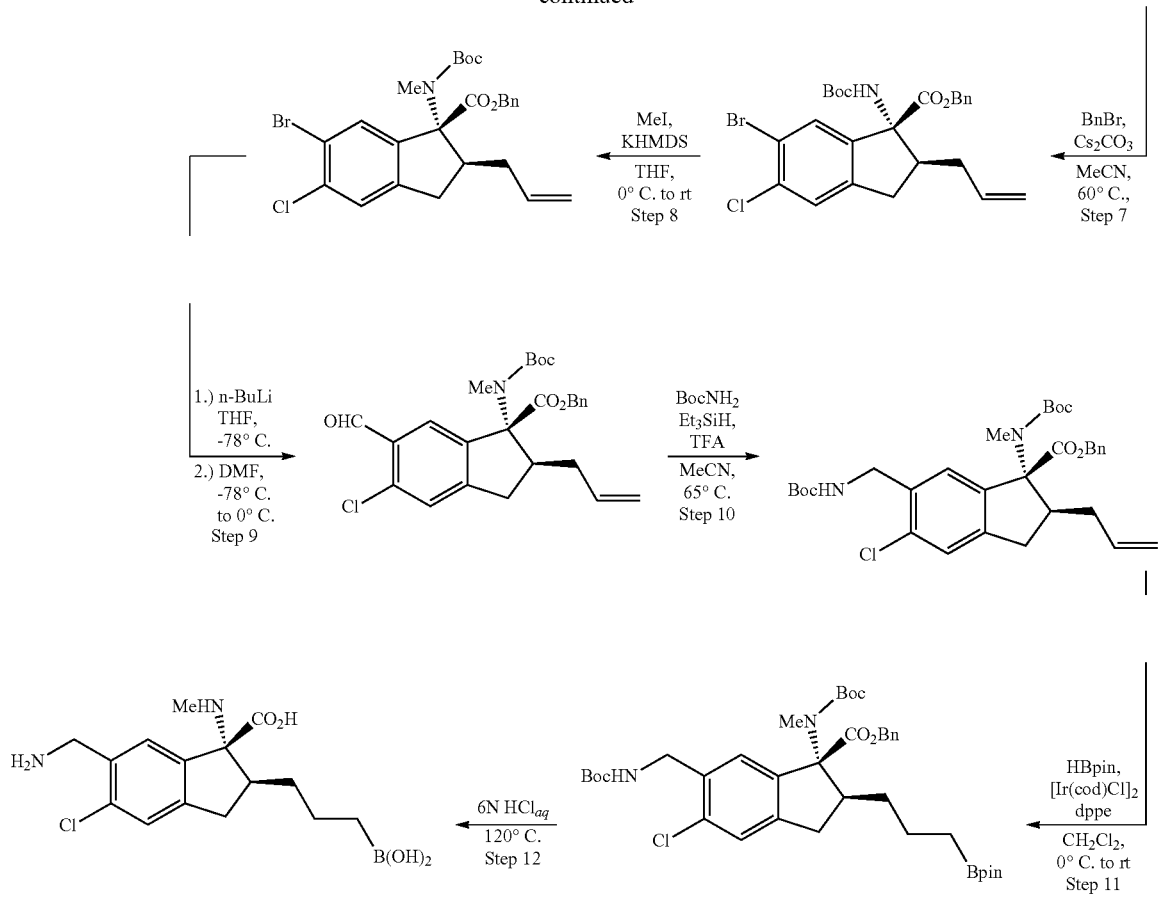

Step 1: (R)-(+)-2-Methyl-2-propanesulfinamide (32.0 g, 264.9 mmol, 3 equiv.) was suspended in anhydrous toluene (300 mL) and heated up to 90° C., then Ti(OEt)$_4$ (18.3 mL, 88.3 mmol, 1 equiv.) was added in one portion. Solid 6-bromo-5-chloro-1-indanone (21.5 g, 88.3 mmol, 1 equiv.) was added in portions (within 1 h). After addition reaction mixture was stirred for 1.5 h at 90° C., then cooled down to room temperature. Na$_2$SO$_4$×10 H$_2$O (28.4 g, 88.3 mmol, 1 equiv.) and celite (20 g) were added and the mixture was vigorously stirred for 30 min. Dark green suspension was filtered through celite and solids were washed with EtOAc (3×100 mL). Combined organics were evaporated and the crude material was purified by column chromatography (silica gel, hex→6:4 hex:EtOAc) to give green solid (25.9 g, 85%).

Step 2: Pd$_2$(dba)$_3$ (662 mg, 0.722 mmol, 2.5% mol.) was dissolved in anhydrous, degassed THF (100 mL) and tributylphosphine (0.723 mL, 2.9 mmol, 10% mol.) was added in one portion. The mixture was stirred at room temperature for 10 min. and then cooled to 4° C. Allyl methyl carbonate (6.7 mL, 57.8 mmol, 2 equiv.) was added followed by TEA (8.0 mL, 57.8 mmol, 2 equiv.). Finally solid imine from Step 1 (10 g, 28.9 mmol) was added and the reaction mixture was stirred at ~1° C. for 6 h then quenched with saturated, aqueous NH$_4$Cl (50 mL). Organic layer was separated, dried over MgSO$_4$, filtered and evaporated. The residue was washed with small amount of EtOAc to give product as pale solid (5 g, 45%).

Step 3: In a 1 L round bottom flask, anhydrous THF (240 mL) was cooled to −78° C. Diethylaluminum cyanide 1M solution in toluene (155 mL, 155 mmol, 1.5 equiv.) was then added and stirred at −78° C. for 5 min. Anhydrous isopropanol (10.5 mL, 103 mmol, 1.0 equiv.) was then added dropwise; the mixture was then immediately removed from the cooling bath and allowed to stir at room temperature for 1 h. In a separate 2 L round bottom flask; the product from Step 2 (40 g, 103 mmol) was dissolved in anhydrous THF (560 mL). This mixture was cooled to −78° C. and the aluminum cyanide mixture was added dropwise over 1 h. Upon complete addition the mixture was removed from the cooling bath and stirred at room temperature overnight. The mixture was once again cooled to −78° C. and quenched using saturated NaHCO$_3$ (300 mL). This was warmed to room temperature and allowed to stir for 1 h. The mixture was filtered over sand and washed with EtOAc (2 L). The mixture was then washed with brine, and the organics were dried over MgSO$_4$, filtered and concentrated. The residue was purified by column chromatography (silica gel, hex→1:1 hex:EtOAc) to give the desired product (33.2 g, 77%).

Step 4: To a solution of the nitrile from Step 3 (15 g, 36 mmol, 1.0 equiv.) in MeOH (360 mL) at −78° C. was added 30% (w/w) H$_2$O$_{2(aq)}$ (9.3 mL, 90 mmol, 2.5 equiv.), dropwise. This followed by the addition of K$_2$CO$_3$ (12.5 g, 90 mmol, 2.5 equiv.). The mixture was allowed to warm to 0° C. and stirred for 12 h and monitored by TLC. After completion of the reaction, the mixture was poured into ice-cold water (1 L) and stirred for 1 h. The resulting precipitate was collected by filtration and washed with water (3×200 mL) to afford the crude amide (12 g) as a white solid, which was used without purification in the next step.

Step 5: Solution of the amide from Step 4 (11 g, 25 mmol) in MeOH (50 mL) was cooled to 0° C. and 3M HCl in MeOH (50 mL) was added dropwise (within 10 min). The cooling bath was removed and the reaction mixture was stirred at room-temperature for 1 h. Solvent was removed in-vacuo and the residue was azeotroped with toluene (2×100 mL) to give the amide as pale brownish solid. The crude material was placed in a heavy wall pressure vessel, diluted with 2M KOH (253 mL) and heated at 150° C. for 60 h. The reaction mixture was cooled down and filtered to remove KOH. The filtrate was cooled to 0° C. and pH was carefully adjusted to 7 using concentrated HCl (~20 mL). The resulted solution was used directly in the next step.

Step 6: To the pH=7 aqueous solution from Step 5, THF was added (253 mL), followed by solid $NaHCO_3$ (16 g, 190.5 mmol) and $(Boc)_2O$ (30 g, 138 mmol) at room temperature. The resulted mixture was stirred at 70° C. for 20 h. After cooling to room temperature, EtOAc (300 mL) and saturated, aqueous $NH_4Cl$ (150 mL) were added. The organic layer was washed with brine (100 mL), dried over $Na_2SO_4$, filtered and evaporated to give crude product that was used in the next step without further purification.

Step 7: To the solution of crude material from Step 6 in MeCN (51 mL) $Cs_2CO_3$ (18.2 g, 55.8 mmol, 2.2 equiv.) and benzyl bromide (6.0 mL, 50.7 mmol, 2.0 equiv.) were added. The resulted mixture was heated to 70° C. for 12 h. After cooling to room temperature, EtOAc (400 mL) and saturated, aqueous $NH_4Cl$ (150 mL) were added. The organic layer was washed with brine (100 mL), dried over $Na_2SO_4$, filtered and evaporated. The residue was purified by column chromatography (silica gel, hex→8:2 hex:EtOAc) to give the benzyl ester (5 g, 38% over 4 steps).

Step 8: The solution of benzyl ester from Step 7 (5.0 g, 9.6 mmol, 1.0 equiv.) in THF (96 mL) was cooled to 0° C. and 1M KHMDS in MTBE (25 mL, 25 mmol, 2.6 equiv.) was added dropwise. The reaction mixture was stirred at 0° C. for 20 min then MeI (3 mL, 48 mmol, 5.0 equiv.) was added dropwise. After additional 15 min, the reaction mixture was warmed up to room temperature and stirred for 3 h, then quenched with EtOAc (200 mL) and saturated, aqueous $NH_4Cl$ (50 mL). The organic layer was washed with brine (20 mL), dried over $Na_2SO_4$, filtered and evaporated. The residue was purified by column chromatography (silica gel, hex→9:1 hex:EtOAc) to afford the title compound as white foam (3.0 g, 59%). ESI MS $[M+H]^+$ for $C_{26}H_{29}BrClNO_4$, calcd 534.1, found 534.0.

Step 9: The product from Step 8 (0.50 g, 0.93 mmol, 1.0 equiv.) was azeotroped with toluene three times before being dissolved in anhydrous THF (19 mL). The solution was cooled to −78° C. and a 2.5 M solution of n-butyllithium in hexanes (0.41 mL, 1.0 mmol, 1.1 equiv.) was added dropwise. After stirring for 30 min, DMF (1.0 mL) was added quickly and the resulting reaction mixture was stirred for an additional 30 min at −78° C. The dry ice-acetone bath was replaced with an ice bath and the stirring was continued for an additional 20 min at 0° C. The reaction mixture was quenched with a saturated aqueous $NH_4Cl$ solution (100 mL) and the aqueous phase was extracted with EtOAc (3×50 mL). The combined organic layers were washed with brine, dried over $Na_2SO_4$, filtered and concentrated by rotary evaporation. The crude product was purified by column chromatography (silica gel, hex→7:3 hex:EtOAc) to give the desired product as a colorless oil (0.33 g, 72%).

Step 10: The product from Step 9 (0.53 g, 1.1 mmol, 1.0 equiv.) was azeotroped with toluene three times before being dissolved in anhydrous MeCN (11 mL). t-Butylcarbamate (0.51 g, 4.4 mmol, 4.0 equiv.), triethylsilane (0.70 mL, 4.4 mmol, 4.0 equiv.) and trifluoroacetic acid (0.16 mL, 2.2 mmol, 2.0 equiv.) were sequentially added under a nitrogen atmosphere and heated to 65° C. After 12 h, the mixture was treated with a saturated aqueous $NaHCO_3$ solution (100 mL). The aqueous layer was extracted with EtOAc (3×50 mL). The combined organic layers were washed with brine, dried over $Na_2SO_4$, filtered and concentrated. The crude product was purified by column chromatography (silica gel, hex→35% EtOAc in hexanes) to give the desired product as a white solid (0.41 g, 64%).

Step 11: The product from Step 10 (0.41 g, 0.70 mmol, 1.0 equiv.) was dissolved in dichloromethane (7 mL) and the stirred solution was evacuated and refilled with nitrogen three times. To this solution bis(1,5-cyclooctadiene)diiridium(I) dichloride (24 mg, 0.035 mmol, 5% mol.) was added, followed by 1,2-bis(diphenylphosphino)ethane (28 mg, 0.070 mmol, 10% mol.), after which the resulting mixture was evacuated and refilled with nitrogen three times. After stirring for 30 min at room temperature, the reaction mixture was cooled to 0° C. and a solution of pinacolborane (0.30 mL, 1.0 mmol, 1.4 equiv.) in dichloromethane (2 mL) was added dropwise with a syringe pump over 1.5 h. After addition, the ice bath was removed and the reaction was stirred for an additional hour at room temperature. The reaction mixture was quenched with a saturated aqueous $NH_4Cl$ solution (50 mL) and the aqueous phase was extracted with dichloromethane (3×20 mL). The combined organic layers were washed with brine, dried over $Na_2SO_4$, filtered and concentrated. The crude product was purified by column chromatography (silica gel, hex→35% EtOAc in hexanes) to afford the desired product as a white solid (0.43 g, 86%).

Step 12: To the product from Step 11 (0.43 g, 0.60 mmol, 1.0 equiv.) was added 6 N HCl (5 mL) and the mixture was heated to 120° C. After 15 h, the reaction mixture was cooled to room temperature and concentrated. The crude product was dissolved with water and concentrated. This process was repeated to remove any residual hydrochloric acid. The crude product was dissolved in water (5 mL) and loaded onto DOWEX® 550-OH resin (7 g) which had been rinsed with MeOH (3×100 mL) and water (3×100 mL) before use. The mixture was stirred for 25 min, and the resin was collected by filtration and washed sequentially with water (3×20 mL), methanol (3×20 mL), dichloromethane (3×20 mL) and water (3×20 mL). The resin was treated with 2N HCl (5 mL), stirred for 15 min and filtered. After repeating this process, the combined aqueous filtrate was frozen and lyophilized to afford the final product as a white solid (156 mg, 66%). $^1$H NMR (400 MHz, $D_2O$) δ7.54 (s, 1H), 7.39 (s, 1H), 4.30 (m, 2H), 3.36 (dd, J=15.8, 8.1 Hz, 1H), 2.81 (dd, J=17.7, 8.0 Hz, 1H), 2.76-2.67 (m, 1H), 2.50 (s, 3H), 1.67-1.36 (m, 4H), 0.87-0.72 (m, 2H). ESI MS $[M-H_2O+H]^+$ for $C_{15}H_{21}BClN_2O_3$, calcd 323.1, found 323.0.

Example 18: rac-(1R,2S)-5-Chloro-2-[3-(dihydroxyboranyl)propyl]-1-(methylamino)-6-[(methylamino)methyl]-2,3-dihydro-1H-indene-1-carboxylic acid

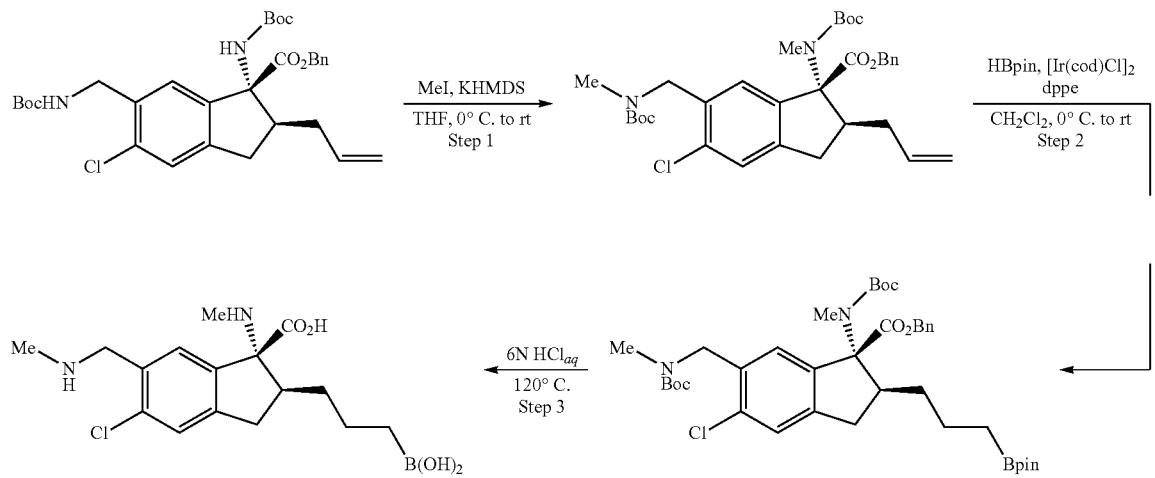

Step 1: The intermediate from Example 17, Step 10 (0.14 g, 0.23 mmol, 1.0 equiv.) was azeotroped with toluene three times before being dissolved in anhydrous THF (2.3 mL). The stirred solution was cooled to 0° C. and a 1.0 M solution of KHMDS in MTBE (0.60 mL, 0.57 mmol, 2.5 equiv.) was added dropwise. After stirring for 20 min, iodomethane (70 µL, 1.2 mmol, 5.0 equiv.) was added dropwise and the resulting reaction mixture was stirred for an additional 20 min at 0° C. The ice bath was removed and stirring was continued for an additional 30 min at room temperature. The reaction mixture was quenched with saturated aqueous NH$_4$Cl (20 mL) and the aqueous phase was extracted with EtOAc (3×20 mL). The combined organic layers were washed with brine, dried over Na$_2$SO$_4$, filtered and concentrated. The crude product was purified by column chromatography (silica gel, 0→20% EtOAc in hexanes) to afford the desired product as a white solid (0.15 g, >100%), which was used without purification in the next step.

Step 2: As for Example 17, Step 11. The desired product was obtained as a white solid (0.13 g, 75% over 2 steps).

Step 3: The title compound was synthesized in a similar fashion to Example 17, Step 12. $^1$H NMR (400 MHz, D$_2$O) δ 7.56 (s, 1H), 7.42 (s, 1H), 4.36 (m, 2H), 3.37 (dd, J=16.5, 8.2 Hz, 1H), 2.82 (dd, J=16.3, 8.1 Hz, 1H), 2.73 (s, 3H), 2.54-2.49 (m, 1H) 2.51 (s, 3H), 1.67-1.53 (m, 2H), 1.50-1.38 (m, 2H), 0.87-0.73 (m, 2H). ESI MS [M−H$_2$O+H]$^+$ for C$_{16}$H$_{23}$BClN$_2$O$_3$, calcd 337.2, found 337.0.

Example 19: (1R,2S)-6-(Aminomethyl)-2-[3-(dihydroxyboranyl)propyl]-5-fluoro-1-(methylamino)-2,3-dihydro-1H-indene-1-carboxylic acid

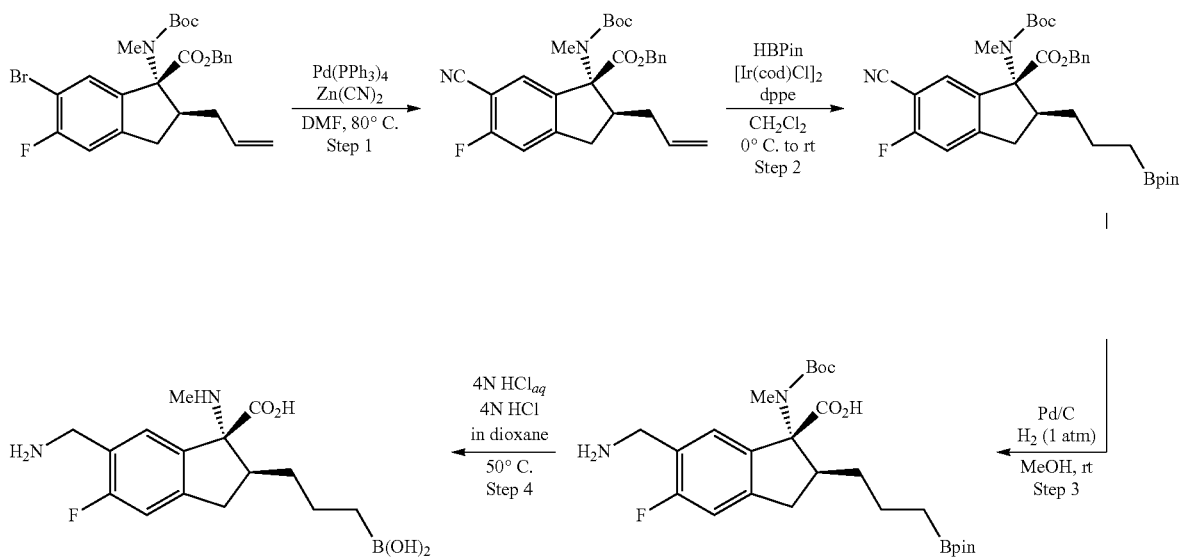

Step 1: A solution of 6-bromo-5-fluoro-1-indanone intermediate (324 mg, 0.625 mmol; prepared in a similar manner to intermediate from Example 17, Step 7) in anhydrous DMF (3.1 mL) was degassed with $N_2$ for 15 min, then $Zn(CN)_2$ (73 mg, 0.625 mmol) and $Pd(PPh_3)_4$ (36 mg, 0.031 mmol, 5% mol.) were added. The vial was sealed with a PTFE-lined septum cap and to 80° C. for 3 h. Additional amounts of $Pd(PPh_3)_4$ (36 mg, 0.031 mmol, 5% mol.) and $Zn(CN)_2$ (73 mg, 0.625 mmol) were added and the reaction was stirred at 80° C. for 2 h. The reaction was cooled to room temperature and diluted with $H_2O$ (10 mL) and MTBE (10 mL). The organic layer was washed with $H_2O$ (2×5 mL), then the combined aqueous layers extracted with MTBE (3×10 mL). The combined organic layers were washed with brine, dried over $MgSO_4$, concentrated. The residue was purified by column chromatography (silica gel, hexanes→20% EtOAc in hexanes) to afford the desired product as a yellow oil (195 mg, 67%).

Steps 2, 3 and 4 were done similar as for Example 8. $^1$H NMR (400 MHz, $D_2O$) δ7.36 (d, J=6.7 Hz, 1H), 7.22 (d, J=9.9 Hz, 1H), 4.25 (d, J=13.8 Hz, 1H), 4.18 (d, J=13.8 Hz, 1H), 3.37 (dd, J=16.3, 7.9 Hz, 1H), 2.89-2.67 (m, 2H), 2.51 (s, 3H), 1.69-1.50 (m, 2H), 1.50-1.31 (m, 2H), 0.90-0.67 (m, 2H). ESI MS [M+H]$^+$ for $C_{15}H_{22}BFN_2O_4$, calcd 325.2, found 325.2.

Example 20: (1R,2S)-6-[(1R)-1-Aminoethyl]-2-[3-(dihydroxyboranyl)propyl]-5-fluoro-1-(methylamino)-2,3-dihydro-1H-indene-1-carboxylic acid brine (100 mL), dried over $MgSO_4$, and filtered. The mixture was concentrated and purified by column chromatography (silica gel, 0→70% EtOAc in hexanes) to afford the desired product as a colorless foam (240 mg; 42%).

Step 2 was done similar as for Example 8.

Step 3 was done similar as for Example 17. $^1$H NMR (400 MHz, $D_2O$) δ7.38 (d, J=6.6 Hz, 1H), 7.19 (d, J=10.4 Hz, 1H), 3.35 (dd, J=16.5, 8.2 Hz, 1H), 2.79 (dd, J=16.5, 7.9 Hz, 1H), 2.72-2.63 (m, 1H), 2.47 (s, 3H), 1.62 (d, J=7.0 Hz, 3H), 1.63-1.51 (m, 2H), 0.88-0.72 (m, 2H). Note: The benzylic proton resonance is obscured by residual $H_2O$ (ca. 4.77 ppm). This resonance is observed in methanol-d4 (δ4.65 (q, J=7.0 Hz, 1H)). ESI MS [M+H]$^+$ for $C_{16}H_{25}BFN_2O_4$, calcd 339.2, found 339.2.

Example 21: (1R,2S)-6-[(1S)-1-Aminoethyl]-2-[3-(dihydroxyboranyl)propyl]-5-fluoro-1-(methylamino)-2,3-dihydro-1H-indene-1-carboxylic acid

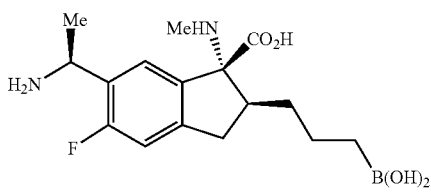 [SMILES: CN[C@@]1(C(=O)O)c2cc([C@H](C)N)c(F)cc2C[C@@H]1CCCB(O)O]

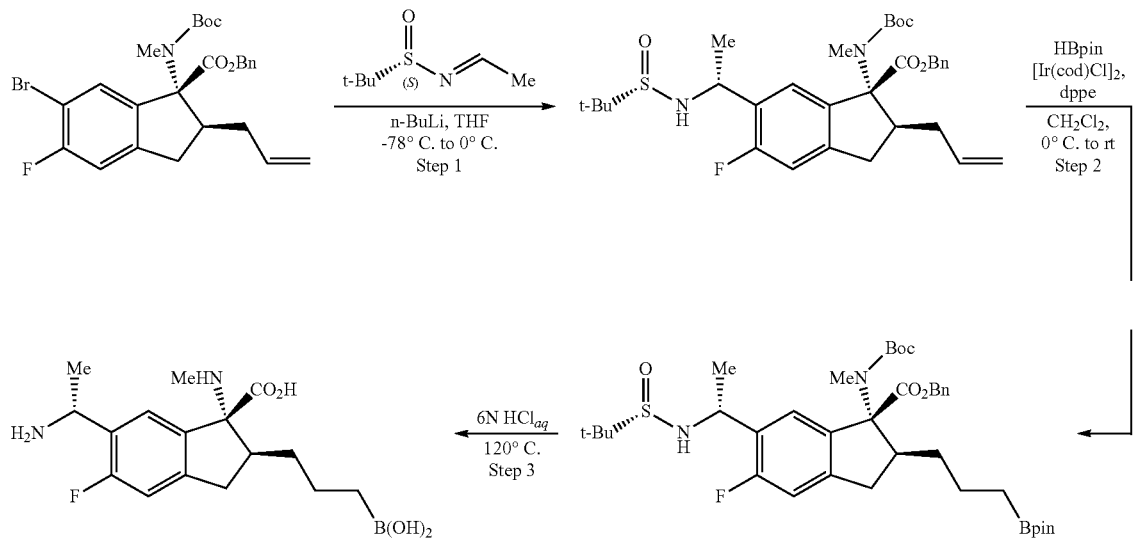

Step 1: A solution of 6-bromo-5-fluoro-1-indanone intermediate (500 mg, 0.964 mmol, prepared in a similar manner to intermediate from Example 17, Step 7) in anhydrous THF (9.6 mL) under $N_2$ was cooled to −78° C. and a 2.5 M solution of n-BuLi in hexanes (1.2 mL, 1.2 mmol, 1.2 equiv.) was added dropwise. After complete addition, the reaction was stirred for 30 min at −78° C., then [N(E),S(S)]-N-Ethylidene-2-methyl-2-propanesulfinamide (336 mg, 1.93 mmol, 2 equiv.) in anhydrous THF (1.2 mL) was added dropwise. The −78° C. bath was replaced with a 0° C. bath and the resulting mixture was stirred for 45 min. The reaction was quenched with saturated aqueous $NH_4Cl$ (100 mL) and poured into EtOAc (150 mL). The layers were separated and the aqueous layer extracted with EtOAc (2×100 mL). The combined organics were washed with The title compound was synthesized in similar fashion to Example 20 using the [N(E),S(R)]-N-Ethylidene-2-methyl-2-propanesulfinamide. $^1$H NMR (400 MHz, $D_2O$) δ7.39 (d, J=6.7 Hz, 1H), 7.20 (d, J=10.4 Hz, 1H), 3.36 (dd, J=16.5, 8.2 Hz, 1H), 2.80 (dd, J=16.2, 8.1 Hz, 1H), 2.75-2.65 (m, 1H), 2.48 (s, 3H), 1.64 (d, J=6.9 Hz, 3H), 1.62-1.51 (m, 2H), 1.52-1.35 (m, 2H), 0.87-0.72 (m, 2H). Note: The benzylic proton resonance is obscured by residual $H_2O$ (ca. 4.77 ppm). This resonance is observed in methanol-$d_4$ (δ4.65 (q, J=7.0 Hz, 1H)). ESI MS [M-OH]$^+$ for $C_{16}H_{23}BFN_2O_3$, calcd 321.2, found 321.2.

Example 22: (1R,2S)-6-{[(1R,2R)-2-Aminocyclopentyl]oxy}-2-[3-(dihydroxyboranyl)propyl]-5-fluoro-1-(methylamino)-2,3-dihydro-1H-indene-1-carboxylic acid

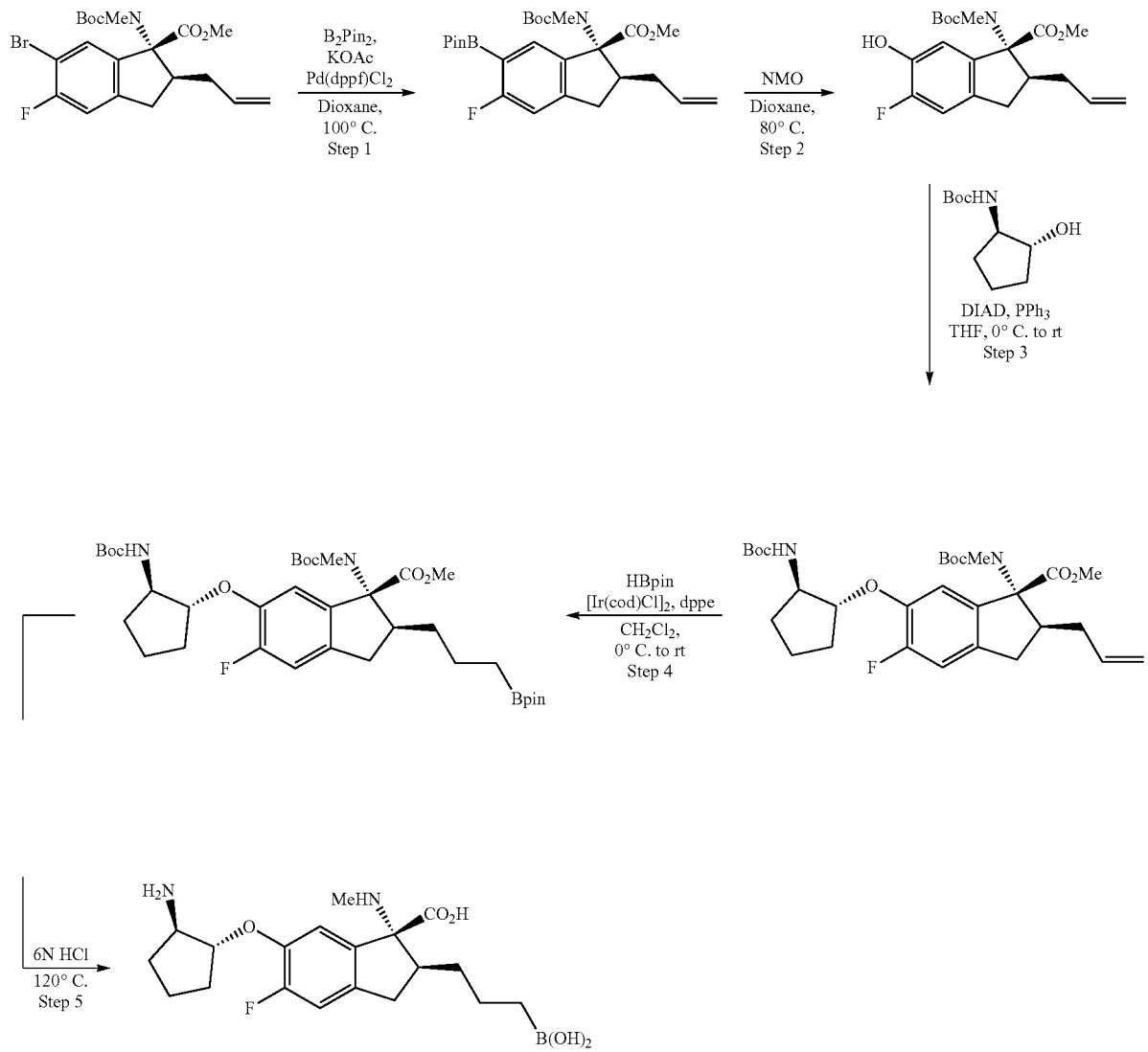

Step 1: A mixture of 6-bromo-5-fluoro-1-indanone intermediate (3.0 g, 6.8 mmol), KOAc (2.0 g, 20.4 mmol, 3 equiv.) and $B_2Pin_2$ (2.6 g, 10.2 mmol, 1.5 equiv.) in anhydrous dioxane (136 mL) was sparged with nitrogen for 10 min and then Pd(dppf)Cl$_2$ (498 mg, 0.68 mmol, 10% mol.) was added. Sparging was continued for 5 min and then the mixture was stirred at 100° C. for overnight. The mixture was cooled to rt, diluted with EtOAc and filtered through a pad of celite. The filtrate was concentrated in vacuo and purified using column chromatography (silica gel, hex→20% EtOAc in hexanes) to give the desired product (1.8 g, 49%).

Step 2: A solution of intermediate from Step 1 (1.6 g, 3.3 mmol) and NMO (0.43 g, 3.6 mmol, 1.1 equiv.) in dioxane (14 mL) was stirred at 80° C. for 3 h. The mixture was concentrated in vacuo and purified using column chromatography (silica gel, hex→40% EtOAc in hexanes) to give the desired product (0.78 g, 62%).

Step 3: The mixture of intermediate from Step 2 (800 mg, 2.1 mmol), Boc-protected amino alcohol (750 mg, 3.2 mmol, 1.5 equiv.) and PPh$_3$ (840 mg, 3.2 mmol, 1.5 equiv.) in anhydrous THF (21 mL) was cooled to 0° C. DIAD (646 mg, 3.2 mmol, 1.5 equiv.) was added dropwise and reaction mixture was stirred at rt for overnight. After quenching with H$_2$O, the mixture was extracted with CH$_2$Cl$_2$ and combined organic layers were dried over MgSO$_4$, filtered and evaporated. The residue was purified using column chromatography (silica gel, hex→40% EtOAc in hexanes) to give the desired product (1.0 g, 83% yield).

Step 4: As for Example 17, Step 11. The desired product was obtained as white solid (900 mg, 73%).

Step 5: As for Example 17, Step 12. $^1$H NMR (400 MHz, D$_2$O) δ7.05 (d, J=11.0 Hz, 1H), 6.94 (d, J=7.6 Hz, 1H), 4.60-4.53 (m, 1H), 3.67 (q, J=7.7 Hz, 1H), 3.23-3.09 (m, 1H), 2.67-2.53 (m, 2H), 2.38 (s, 3H), 2.19-2.06 (m, 1H), 2.06-1.94 (m, 1H), 1.77-1.20 (m, 8H), 0.76-0.55 (m, 2H). ESI-MS [M+H]$^+$ for C$_{19}$H$_{28}$BFN$_2$O$_5$, calcd 394.2, found 394.3.

Example 23: (1R,2S)-6-[1-Aminocyclopropyl]-2-[3-(dihydroxyboranyl)propyl]-5-fluoro-1-(methylamino)-2,3-dihydro-1H-indene-1-carboxylic acid

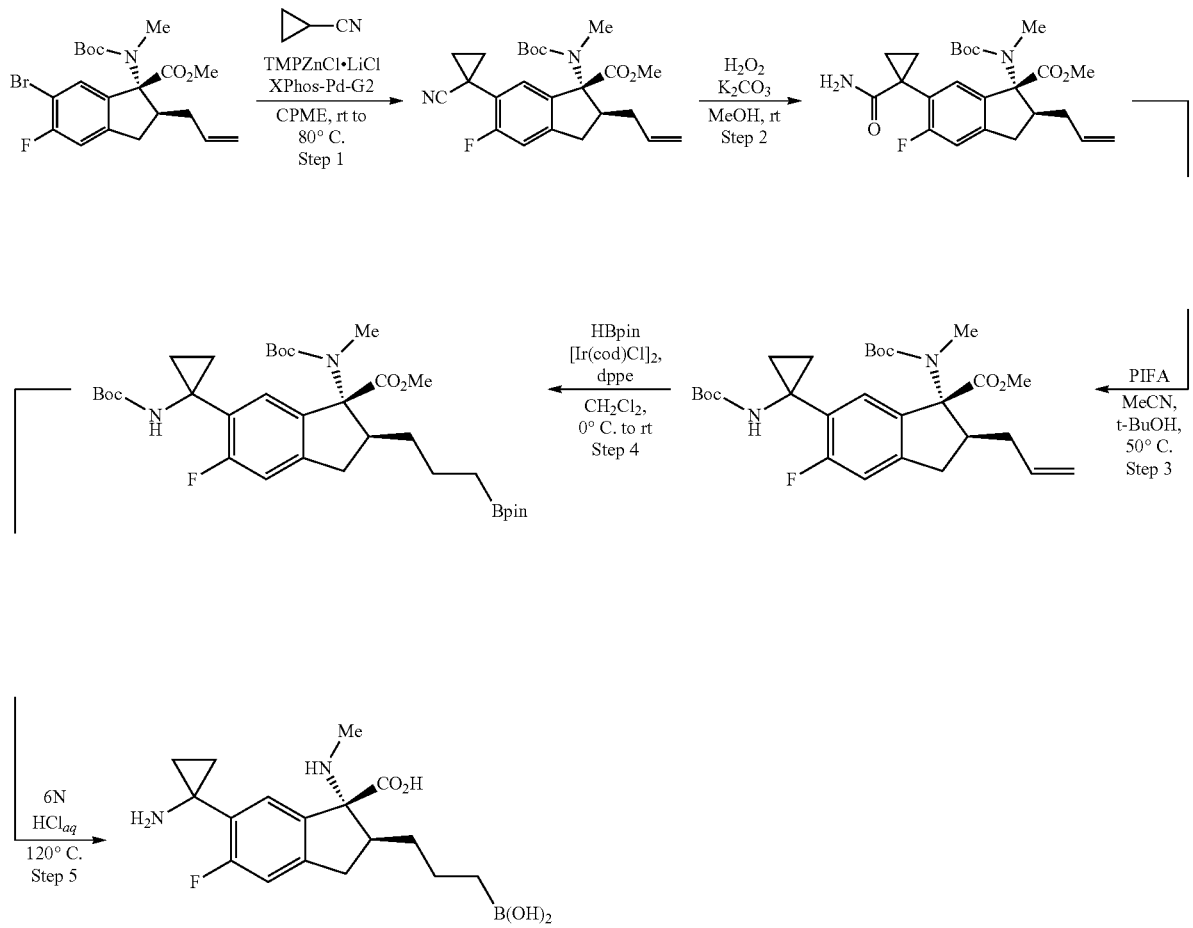

Step 1: To a degassed solution of 6-bromo-5-fluoro-1-indanone intermediate (1.8 g, 4.07 mmol,) in anhydrous cyclopentylmethyl ether (13.5 mL) was added XPhos-Pd-G2 (160 mg, 0.20 mmol). Cyclopropanecarbonitrile (0.36 mL, 4.88 mmol) was added dropwise and the stirred mixture was evacuated and refilled with nitrogen three times. After stirring the reaction mixture for 10 min at rt, tetramethylpiperidinylzinc chloride lithium chloride (TMPZnCl·LiCl) (1.0 M in THF, 4.88 mL, 4.88 mmol) was added dropwise over 15 min while maintaining temperature below 30° C. After stirring the reaction mixture for 30 min at rt, it was heated to 80° C. for 1 h. The reaction mixture was cooled to rt and treated with methanol, filtered through a pad of celite and concentrated in vacuo. The residue was purified using column chromatography (silica gel, hex→30% EtOAc in hexanes) to give the desired product (1.26 g, 72% yield).

Step 2: To a solution of the nitrile from Step 1 (0.59 g, 1.38 mmol) in MeOH (14 mL) at 0° C. was added 30% (w/w) $H_2O_{2(aq)}$ 0.47 mL, 4.14 mmol) dropwise, followed by the addition of $K_2CO_3$ (0.38 g, 2.76 mmol). The mixture was allowed to warm to rt and monitored by TLC.

After reaction completion, the mixture was poured into water and extracted with dichloromethane. The combined organics were washed with an aqueous solution of sodium thiosulfate, then brine, dried over $Na_2SO_4$, and filtered. The mixture was concentrated and purified using column chromatography (silica gel, $CH_2Cl_2$→10% MeOH in $CH_2Cl_2$) to give the desired product (0.52 g, 85% yield).

Step 3: To a solution of the amide from Step 2 (0.2 g, 0.45 mmol,) in acetonitrile (13.5 mL) and tert-butanol (1.1 mL) was added [bis(trifluoroacetoxy)iodo]benzene (PIFA) (0.22 g, 0.50 mmol) in one portion. The reaction mixture was heated to 50° C. for 2 h. After cooling to room temperature, EtOAc and saturated, $NaHCO_{3(aq)}$ were added. The organic layer was washed with brine, dried over $Na_2SO_4$, filtered and evaporated. The residue was purified using column chromatography (silica gel, hex→30% EtOAc in hexanes) to give the desired product (140 mg, 62% yield).

Step 4: As for Example 17, Step 11. The desired product was obtained as a white solid (145 mg, 83% yield).

Step 5: As for Example 17, Step 12. The desired product was obtained as a white solid (74 mg, 84%). $^1$H NMR (400 MHz, $D_2O$) δ7.44 (d, J=6.6 Hz, 1H), 7.22 (d, J=10.2 Hz, 1H), 3.37 (dd, J=16.3, 7.8 Hz, 1H), 2.90-2.70 (m, 2H), 2.50 (s, 3H), 1.67-1.53 (m, 2H), 1.53-1.36 (m, 4H), 1.31-1.19 (m, 2H), 0.88-0.71 (m, 2H). ESI-MS [M–$H_2O$+H]$^+$ for $C_{17}H_{24}BFN_2O_3$, calcd 333.2, found 333.0.

Example 24: (1R,2S)-2-[3-(Dihydroxyboranyl)propyl]-5-fluoro-1-(methylamino)-6-[(2R)-pyrrolidin-2-yl]-2,3-dihydro-1H-indene-1-carboxylic acid

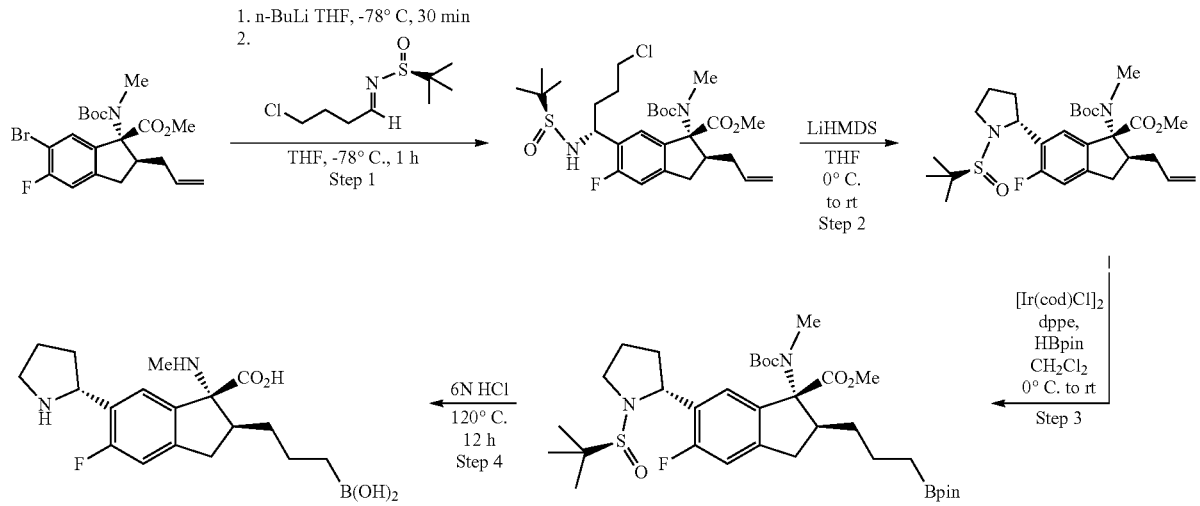

Step 1: To a solution of 6-bromo-5-fluoro-1-indanone intermediate (1.02 g, 2.31 mmol) in THF (33 mL) at −78° C. was added n-BuLi (2.5 M in hexanes, 0.88 mL, 0.95 equiv.) dropwise. The reaction mixture was stirred at −78° C. for 30 min. At this point, a solution of ($S^2S$)—N-[(1E)-4-chlorobutylidene]-2-methylpropane-2-sulfinamide (0.97 g, 4.62 mmol, 2.0 equiv.) in THF (10.6 mL) was added slowly over a period of 15 min to the above reaction mixture. The reaction mixture was stirred at −78° C. for an additional 1 h. The reaction was subsequently warmed to 0° C. and quenched with saturated $NH_4Cl$ solution (10 mL) and $H_2O$ (10 mL), followed by extraction into EtOAc (×2). The combined organic layer was washed with brine, dried over $Na_2SO_4$ and concentrated in vacuo to give a crude residue that was purified by column chromatography (silica gel, hex→80% EtOAc in hexanes) to afford the product as a yellow oil (297 mg, 22%). ESI MS [M+H]$^+$ for $C_{28}H_{43}ClFN_2O_5S$, calcd 573.2, found 573.2.

Step 2: The product from Step 1 (297 mg, 0.519 mmol) was dissolved in THF (2.2 mL). The reaction mixture was cooled to 0° C. prior to the dropwise addition of LiHMDS (1M in THF, 0.78 mL, 1.5 equiv.). The reaction mixture was immediately warmed to rt and stirred for an additional 1 h. At this point, reaction was quenched with saturated $NH_4Cl$ solution (10 mL) and $H_2O$ (10 mL), followed by extraction into EtOAc (×2). The combined organic layer was washed with brine, dried over $Na_2SO_4$ and concentrated in vacuo to give a crude residue that was purified by column chromatography (silica gel, hex→80% EtOAc in hexanes) to afford the product as a colorless oil (278 mg, quant.). ESI MS [M+H]$^+$ for $C_{28}H_{42}FN_2O_5S$, calcd 537.3, found 537.1.

Step 3: As for Example 17, Step 11. The desired product was obtained as a colorless oil (240 mg, 70%). ESI MS [M+H]$^+$ for $C_{34}H_{54}BFN_2O_7$, calcd 687.2, found 687.4.

Step 4: The product from Step 3 (240 mg, 0.36 mmol) was suspended in 6 N HCl and the reaction mixture was heated to 120° C. for 16 h. Reaction mixture was cooled to rt, solvent was removed in vacuo to give a crude residue that was purified by RP-HPLC ($CH_3CN/H_2O$) to provide (1R, 2S)-2-[3-(dihydroxyboranyl)propyl]-5-fluoro-1-(methylamino)-6-[(2R)-pyrrolidin-2-yl]-2,3-dihydro-1H-indene-1-carboxylic acid as a white solid (92 mg, 76%). $^1$H NMR (400 MHz, $D_2O$) δ7.31 (d, J=6.7 Hz, 1H), 7.17-7.13 (m, 1H), 3.42-3.21 (m, 3H), 2.79-2.62 (m, 2H), 2.43 (s, 3H), 2.41-2.29 (m, 1H), 2.22-2.10 (m, 3H), 2.08-2.00 (m, 1H), 1.58-1.45 (m, 2H), 1.40-1.29 (m, 2H), 0.82-0.60 (m, 2H). $^{19}$F NMR (376 MHz, $D_2O$) δ-113.7. ESI MS [M+H]$^+$ for $C_{18}H_{27}BFN_2O_4$, calcd 365.2, found 365.2.

Analytical Methods

LC: Agilent 1100 series; Mass spectrometer: Agilent G6120BA, single quad

LC-MS method: LCMS column Waters XSelect® HSS C18 3.5 um (2.1×75 mm), 35° C., 0.9 mL/min flow rate, a 2.5 min gradient of 0 to 100% B with 0.5 min wash at 100% B; A=0.1% of formic acid/5% acetonitrile/94.9% water; B=0.1% of formic acid/5% water/94.9% acetonitrile Flash column: ISCO Rf+

Reverse phase HPLC: ISCO-EZ; Column: Kinetex 5 μm EVO C18 100 A; 250×21.2 mm (Phenomenex)

Measurement of Compound Potency by Arginase Coupled Enzymatic Assay Using Recombinant Human ARG1 and ARG2

Purified recombinant human ARG1 and ARG2 were prepared in 50 mM Bicine, pH 8.5, 100 μM $MnCl_2$, 20% glycerol and 1mM DTT at a final stock concentration of 14.4 μM and 7.56 μM respectively. 2.5 nM of either ARG1 or ARG2 were incubated with varying concentrations of compounds in 10 mM sodium phosphate, pH 7.4, 0.1 mM $MnCl_2$ and 2.5% DMSO in a total volume of 40 μl in a 384-well microplate (Corning™ #3640) at 37° C. for 1 h. The arginase enzymatic reaction was initiated by addition of 10 μl of 4 mM L-Arginine pre-incubated in 10 mM sodium phosphate, pH 7.4, and 0.1 mM $MnCl_2$ at 37° C. into the enzyme and compound mixture, giving the final reaction conditions: 2 nM of ARG1 or ARG2 and 0.8 mM of L-Arginine in 10 mM sodium phosphate, pH 7.4, 0.1 mM $MnCl_2$ and 2% DMSO with varying concentrations of compounds. Following 2 h incubation at 37° C., the arginase enzymatic reaction was stopped by transfer of 10 μl of reaction into 10 μl of detection mix (204 μM Amino-2-Borono-6-Hexanoic Acid, 0.25 μl Arginase Enzyme mix, 0.25 μl Arginase Developer, 0.25 μl Arginase Converter Enzyme in Arginase Assay Buffer from Arginase Activity Colorimetric Assay Kit, BioVision Inc. #K755-100) in a transparent 384-well microplate (Greiner #781801). The plate was immediately put into a plate reader (Synergy™ Neo2 Multi-Mode Microplate Reader) to monitor absorption at 570 nm at 37° C. Absorption values at 12~20 min were used to calculate compound potency. The value of the DMSO blank (MIN inhibition=100% activity) was used as a negative control. The positive control was established by adding 8 µl of enzyme and DMSO mix into 10 µl of detection mix followed by addition of 2 µl of L-Arginine (MAX inhibition=0% activity). To calculate the percent activity, Equation 1 was used. $Abs_{570nm}$ is the value at a given compound concentration:

$$\% \text{ Activity} = \frac{Abs_{570\,nM} - \text{MAX}}{\text{MIN} - \text{MAX}} \times 100 \quad \text{Equation 1}$$

The concentration of compound that resulted in 50% loss of the enzyme activity ($IC_{50}$) was calculated by GraphPad Prism using Equation 2 where N is the Hill coefficient:

$$\% \text{ Activity} = \text{Bottom} + \frac{\text{Top} - \text{Bottom}}{1 + \left(\frac{[I]}{IC_{50}}\right)^N} \quad \text{Equation 2}$$

A counter-screen was performed to identify any inhibition of the coupling enzymes by the test compounds. 10 µl of 0.26 mM of urea with varying concentrations of compounds in 10 mM sodium phosphate, pH 7.4, 0.1 mM $MnCl_2$ and 2% DMSO were added into 10 µl of detection mix in place of the arginase enzymatic reaction mix. Absorption was monitored at 570 nm as described above. The values of a no substrate blank (without urea; MAX inhibition=0% activity) and a DMSO blank (MIN inhibition=100% activity) were used as positive and negative controls respectively. A flat dose response curve was expected for compounds that did not inhibit any coupling enzymes. Inactivity in the counter-screen was used to confirm that results accurately reflected $IC_{50}$ values for ARG1 and ARG2.

Additional compounds were prepared and evaluated with structures and activity as shown in Table 1, below. Preparative methods used synthetic methodology similar to the Examples above.

TABLE 1

| Specific Examples | |
|---|---|
| Example | hARG1 |
| [pyridine-fused cyclopentane with H₂N, CO₂H and propyl-B(OH)₂ substituents] | + |
| [4-Br indane with H₂N, CO₂H and propyl-B(OH)₂ substituents] | + |
| [4-CN indane with H₂N, CO₂H and propyl-B(OH)₂ substituents] | + |
| [4-(CH₂NH₂) indane with H₂N, CO₂H and propyl-B(OH)₂ substituents] | ++ |
| [4-(CH₂OH) indane with H₂N, CO₂H and propyl-B(OH)₂ substituents] | + |
| [4-(1H-pyrazol-4-yl) indane with H₂N, CO₂H and propyl-B(OH)₂ substituents] | + |
| [6-Me indane with H₂N, CO₂H and propyl-B(OH)₂ substituents] | + |
| [2-Me indane with H₂N, CO₂H and propyl-B(OH)₂ substituents] | + |
| [6-MeO indane with H₂N, CO₂H and propyl-B(OH)₂ substituents] | ++ |

TABLE 1-continued
Specific Examples
| Example | hARG1 |
|---|---|
| 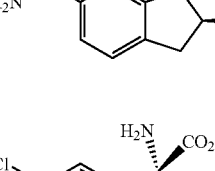 | ++ |
| 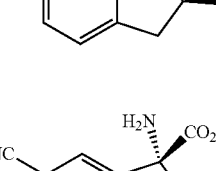 | +++ |
| 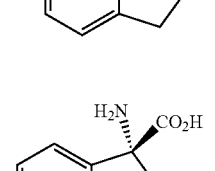 | ++ |
| 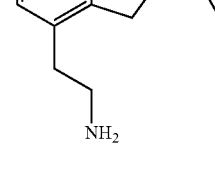 | + |
| 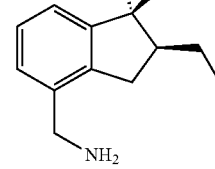 | ++ |
| 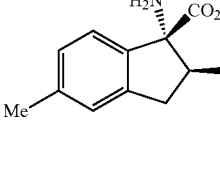 | +++ |
| 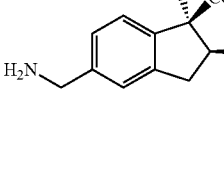 | + |
|  | +++ |
| 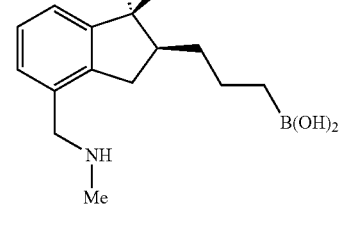 | ++ |
| 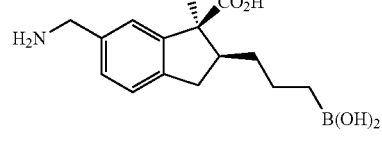 | +++ |
| 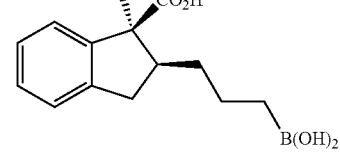 | ++ |
| 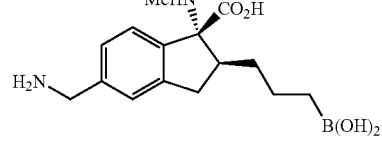 | ++ |
| 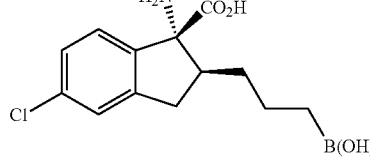 | ++ |
| 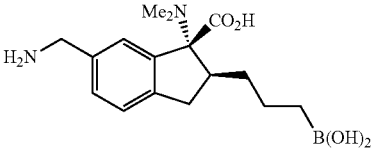 [SMILES: CN(C)[C@@]1(C(=O)O)c2cc(CN)ccc2C[C@@H]1CCCB(O)O] | +++ |

TABLE 1-continued

Specific Examples

| Example | hARG1 |
|---|---|
| (indane with H2N, CO2H, 5-CH2CH2NH2, 2-CH2CH2CH2B(OH)2) | ++ |
| (indane with MeHN, CO2H, 6-OMe, 5-CH2NH2, 2-propyl-B(OH)2) | +++ |
| (indane with MeHN, CO2H, 6-Cl, 5-CH2NH2, 2-propyl-B(OH)2) | +++ |
| (indane with H2N, CO2H, 6-CH(Me)NH2, 2-propyl-B(OH)2) | +++ |
| (indane with H2N, CO2H, 6-CH2CH2NH2, 5-Cl, 2-propyl-B(OH)2) | +++ |
| (indane with EtHN, CO2H, 6-OMe, 5-CH2NH2, 2-propyl-B(OH)2) | ++ |
| (indane with HN(Me), CO2H, 7-F, 5-CH2NH2, 2-propyl-B(OH)2) | ++ |
| (indane with H2N, CO2H, 5-(3-aminoazetidin-1-yl), 2-propyl-B(OH)2) | + |
| (indane with MeHN, CO2H, 6-CH2NH2, 5-Cl, 2-propyl-B(OH)2) | +++ |
| (indane with MeHN, CO2H, 6-CH2NH2, 5-F, 2-propyl-B(OH)2) | +++ |
| (indane with MeHN, CO2H, 6-CH(Me)NH2, 5-F, 2-propyl-B(OH)2) | +++ |
| (indane with MeHN, CO2H, 6-CH(Me)NH2, 5-F, 2-propyl-B(OH)2) | +++ |
| (indane with MeHN, CO2H, 6-CH2NHMe, 5-Cl, 2-propyl-B(OH)2) | +++ |
| (indane with MeHN, CO2H, 6-CH(Me)NH2, 5-Cl, 2-propyl-B(OH)2) | +++ |
| (indane with MeHN, CO2H, 6-C(Me)2NH2, 5-F, 2-propyl-B(OH)2) | +++ |
| (indane with MeHN, CO2H, 6-CH(Me)NH2, 5-Cl, 2-propyl-B(OH)2) | +++ |
| (indane with MeHN, CO2Me, 6-CH2NH2, 5-Cl, 2-propyl-B(OH)2) | ++ |
| (indane with MeHN, CO2H, 6-CH(Me)NH2, 2-propyl-B(OH)2) | +++ |

TABLE 1-continued

Specific Examples

| Example | hARG1 |
|---|---|
| (structure: 6-amino-5-chloro-indane with MeHN, CO2H, propyl-B(OH)2) | ++ |
| (structure: 6-(2-amino-propan-2-yl)-5-chloro-indane) | +++ |
| (structure: 6-(hydroxymethyl)-5-chloro-indane) | ++ |
| (structure: 6-(1-amino-2,2,2-trifluoroethyl)-indane) | ++ |
| (structure: 6-(pyridin-2-yl)-5-fluoro-indane) | ++ |
| (structure: 6-((3,3-difluoroazetidin-1-yl)methyl)-5-chloro-indane) | ++ |
| (structure: 6-(3-methylpyridin-2-yl)-5-fluoro-indane) | ++ |
| (structure: 6-((3-hydroxypyrrolidin-1-yl))-5-fluoro-indane) | ++ |
| (structure: 6-((methylamino)methyl)-5-fluoro-indane) | +++ |

TABLE 1-continued

Specific Examples

| Example | hARG1 |
|---|---|
| (structure: 6-(pyrrolidin-1-ylmethyl)-5-fluoro-indane) | +++ |
| (structure: 6-((dimethylamino)methyl)-5-chloro-indane) | +++ |
| (structure: 6-(pyridin-3-yl)-5-fluoro-indane) | ++ |
| (structure: 6-(4-(aminomethyl)phenyl)-5-chloro-indane) | +++ |
| (structure: 6-(pyridin-2-ylamino)-5-fluoro-indane) | ++ |
| (structure: 6-(1-amino-2,2,2-trifluoroethyl)-indane) | ++ |
| (structure: 6-((2-aminoimidazol-1-yl)methyl)-5-chloro-indane) | +++ |
| (structure: 6-(aminomethyl)-indane) | +++ |
| (structure: 6-(acetamidomethyl)-indane) | ++ |

TABLE 1-continued

Specific Examples

| Example | hARG1 |
|---|---|
| (structure) | +++ |
| (structure) | +++ |
| (structure) | +++ |
| (structure) | ++ |
| (structure) | +++ |
| (structure) | +++ |
| (structure) | ++ |
| (structure) | +++ |
| (structure) | +++ |

TABLE 1-continued

Specific Examples

| Example | hARG1 |
|---|---|
| (structure) | +++ |
| (structure) | +++ |
| (structure) | ++ |
| (structure) | ++ |
| (structure) | +++ |
| (structure) | +++ |
| (structure) | +++ |
| (structure) | +++ |

TABLE 1-continued
Specific Examples
| Example | hARG1 |
|---|---|
| 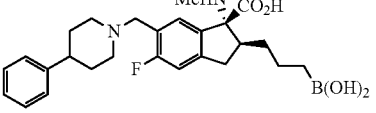 | +++ |
| 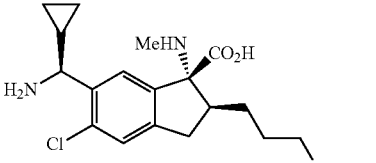 | +++ |
| 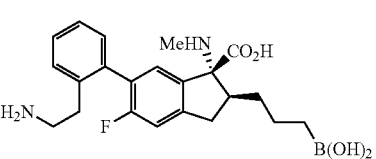 | +++ |
| 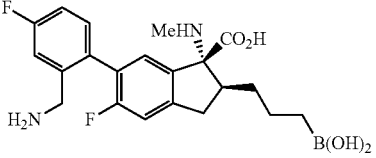 | +++ |
| 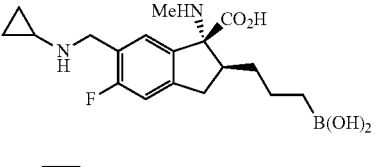 | +++ |
| 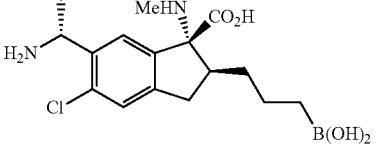 [SMILES: CN[C@@]1(C(=O)O)c2cc(CN)c(Cl)cc2C[C@@H]1CCCB(O)O] | +++ |
| 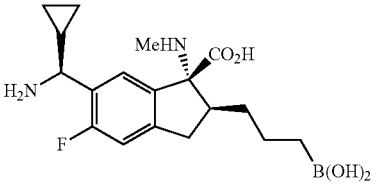 [SMILES: CN[C@@]1(C(=O)O)c2cc([C@@H](N)C3CC3)c(Cl)cc2C[C@@H]1CCCB(O)O] | +++ |
| 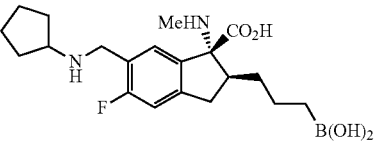 [SMILES: CN[C@@]1(C(=O)O)c2cc(CNC3CCCC3)c(F)cc2C[C@@H]1CCCB(O)O] | +++ |
| 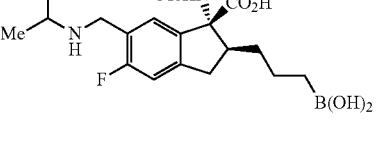 | +++ |
| 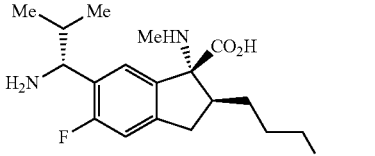 | +++ |
| 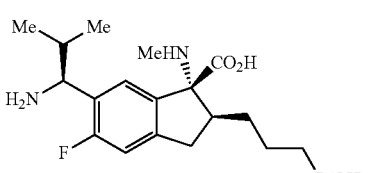 | +++ |
| 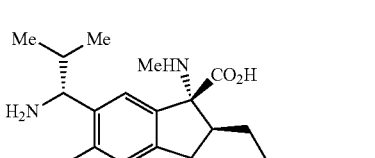 | +++ |
| 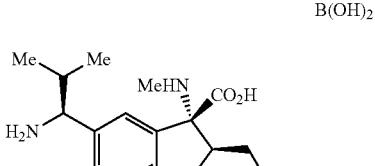 | +++ |
| 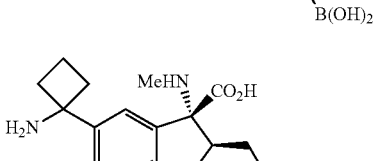 | +++ |
| 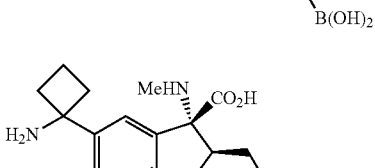 | +++ |
| 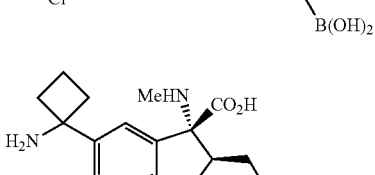 | +++ |
| 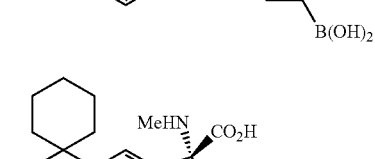 | +++ |
| 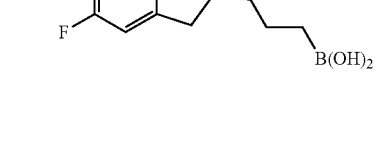 | +++ |

TABLE 1-continued
Specific Examples
| Example | hARG1 |
|---|---|
| 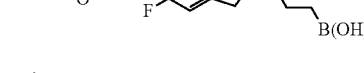 | +++ |
| 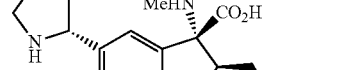 | +++ |
| 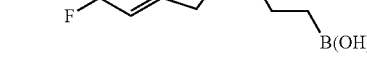 | +++ |
| 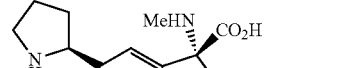 | +++ |
| 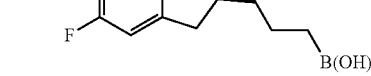 | +++ |
|  | +++ |
| 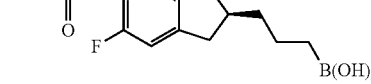 | +++ |
| 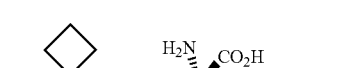 | +++ |
| 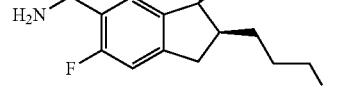 | +++ |
|  | +++ |
| 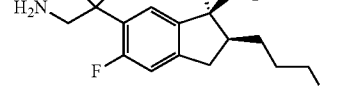 | +++ |
|  | ++ |
| 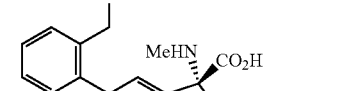 | +++ |

TABLE 1-continued

Specific Examples

| Example | hARG1 |
|---|---|
| (structure: cyclopentyl with H2N, fused to F-indane with MeHN, CO2H, propyl-B(OH)2) | +++ |
| (structure: C(Me)2 with H2N, F-indane core with MeHN, CO2H, propyl-B(OH)2) | +++ |
| (structure: cyclobutyl with gem-diMe and H2N, F-indane core, MeHN, CO2H, propyl-B(OH)2) | +++ |
| (structure: CH(Me)NH2, F3CCH2O substituent, indane with MeHN, CO2H, propyl-B(OH)2) | +++ |
| (structure: C(Me)2NH2 ethyl, F-indane, MeHN, CO2H, propyl-B(OH)2) | +++ |
| (structure: CH(Me)NH2, Me-indane, MeHN, CO2H, propyl-B(OH)2) | +++ |
| (structure: C(Et)(Me)NH2, F-indane, MeHN, CO2H, propyl-B(OH)2) | +++ |
| (structure: CH(Me)NH2, MeO-indane, MeHN, CO2H, propyl-B(OH)2) | +++ |

TABLE 1-continued

Specific Examples

| Example | hARG1 |
|---|---|
| (structure: piperidine-4-yl, F-indane, MeHN, CO2H, propyl-B(OH)2) | +++ |
| (structure: 2,2-dimethylpiperidine-N-CH2, F-indane, MeHN, CO2H, propyl-B(OH)2) | +++ |
| (structure: proline-N-CH2 (HO2C-pyrrolidine), F-indane, MeHN, CO2H, propyl-B(OH)2) | ++ |
| (structure: CH(Me)NHMe, F-indane, MeHN, CO2H, propyl-B(OH)2) | +++ |
| (structure: CH(Et)NHMe, F-indane, MeHN, CO2H, propyl-B(OH)2) | +++ |
| (structure: 4-(H2NCH2)-phenyl, indane, MeHN, CO2H, propyl-B(OH)2) | +++ |

(Potency: hARG1: + means >1 μM, ++ means 100 nM to 1 μM, +++ means <100 nM)

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound having the Formula (I) or a pharmaceutically acceptable salt, hydrate, or solvate thereof, wherein,

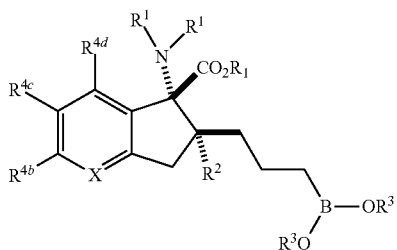
(I)

X is N or $CR^{4a}$, each $R^1$ is independently H or $C_{1-8}$ alkyl, $R^2$ is H or $CH_3$;

each $R^3$ is independently H or $C_{1-8}$ alkyl; or two $R^3$ groups are joined together to form a 5 or 6-membered ring which is unsubstituted or substituted with from 1 to 4 $R^a$;

each $R^{4a}$, $R^{4b}$, $R^{4c}$, and $R^{4d}$ is independently selected from the group consisting of H, halogen, CN, $C_{1-8}$ alkyl, $C_{1-8}$ alkoxy, $C_{1-8}$ hydroxyalkyl, $C_{1-8}$ haloalkyl, $C_{1-8}$ haloalkoxy, -$X^1$-Y,-$X^1$—$SO^2R^{5a}$, and -$X^1$—$NR^{5b}R^{5c}$, each $R^{5a}$, $R^{5b}$, and $R^{5c}$ is independently selected from the group consisting of H, $C_{1-8}$ alkyl, $C_{1-8}$ haloalkyl, $C_{1-8}$ alkylC (O)-, $C_{3-7}$ cycloalkyl, 3- to 7-membered heterocycloalkyl, aryl, heteroaryl, and an amino acid, or $R^{5b}$ and $R^{5c}$ are joined together to form a 4- to 6-membered ring; and wherein each of the 4- to 6-membered ring, $C_{3-7}$ cycloalkyl, or 3- to 7-membered heterocycloalkyl, aryl, and heteroaryl, are unsubstituted or substituted with from 1 to 4 $R^b$;

each $X^1$ is a bond, —O—, $C_{1-6}$ alkylene, or —O—$C_{1-6}$ alkylene, wherein the alkylene portions are unsubstituted or substituted with 1 to 4 $R^c$ and 0 or 1 oxo;

each $R^a$, $R^b$, and $R^c$ is independently halogen, CN, OH, $NH_2$, $CO_2H$, $C_{1-4}$ alkyl, $C_{1-4}$ haloalkyl, $C_{3-6}$ cycloalkyl, or phenyl, or two Re are combined to form a $C_{3-6}$ cycloalkyl which is unsubstituted or substituted with 1 to 3 $R^d$;

each Y is independently phenyl, a 5- or 6-membered heteroaryl, 3- to 7-membered heterocycloalkyl, or $C_{3-6}$ cycloalkyl, each of which is unsubstituted or substituted with from 1 to 3 $R^d$, and each Rd is independently halogen, $C_{1-4}$ alkyl, amino, amino$C_{1-4}$ alkyl, $C_{1-4}$ haloalkyl, OH, or $C_{1-4}$ hydroxyalkyl.

2. The compound of claim 1, or a pharmaceutically acceptable salt, hydrate, or solvate thereof, wherein:

X is N or $CR^{4a}$;

each $R^1$ is independently H or $C_{1-8}$ alkyl, $R^2$ is H or $CH_3$;

each $R^3$ is independently H or $C_{1-8}$ alkyl; or two $R^3$ groups are joined together to form a 5 or 6-membered ring which is unsubstituted or substituted with from 1 to 4 $R^a$;

each $R^{4a}$, $R^{4b}$, $R^{4c}$, and $R^{4d}$ is independently selected from the group consisting of H, halogen, CN, $C_{1-8}$ alkyl, $C_{1-8}$ alkoxy, $C_{1-8}$ hydroxyalkyl, $C_{1-8}$ haloalkyl, -$X^1$-Y,-$X^1$ $SO^2R^{5a}$, and -$X^1$-$NR^{5b}R^{5c}$, each $R^{5a}$, $R^{5b}$, and $R^{5c}$ is independently selected from the group consisting of H, $C_{1-8}$ alkyl, $C_{1-8}$ haloalkyl, $C_{1-8}$ alkylC (O)-, $C_{3-7}$ cycloalkyl, 3- to 7-membered heterocycloalkyl, aryl, heteroaryl, and an amino acid, or $R^{5b}$ and $R^{5c}$ are joined together to form a 4- to 6-membered ring; and wherein each of the 4- to 6-membered ring, $C_{3-7}$ cycloalkyl, or 3- to 7-membered heterocycloalkyl, aryl, and heteroaryl, are unsubstituted or substituted with from 1 to 4 $R^b$;

each $X^1$ is a bond or $C_{1-6}$ alkylene which is unsubstituted or substituted with 1 to 4 $R^c$;

each $R^a$, $R^b$, and $R^c$ is independently halogen, CN, OH, $NH_2$, $C_{1-4}$ alkyl, $C_{1-4}$ haloalkyl, $C_{3-6}$ cycloalkyl, or phenyl, or two $R^c$ are combined to form a $C_{3-6}$ cycloalkyl;

each Y is independently phenyl or a 5- or 6-membered heteroaryl, each of which is unsubstituted or substituted with from 1 to 3 $R^d$; and each $R^d$ is independently halogen, $C_{1-4}$ alkyl, amino, amino$C_{1-4}$ alkyl, $C_{1-4}$ haloalkyl, OH, or $C_{1-4}$ hydroxyalkyl.

3. The compound of claim 1, or a pharmaceutically acceptable salt, hydrate, or solvate thereof, having a formula selected from the group consisting of:

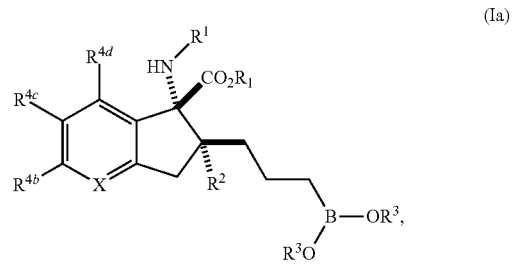
(Ia)

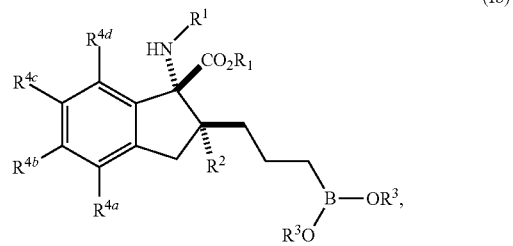
(Ib)

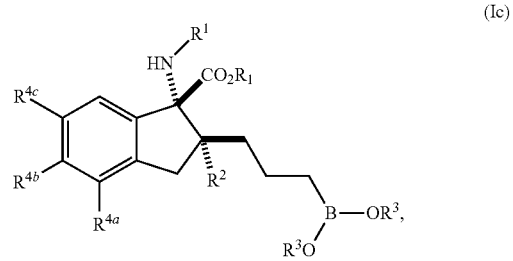
(Ic)

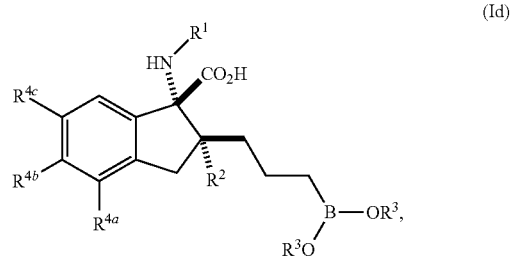
(Id)

-continued

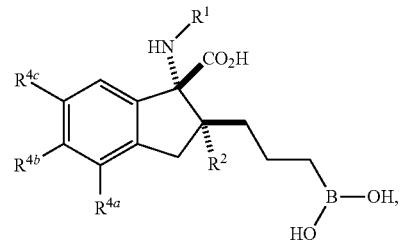
(Ie)

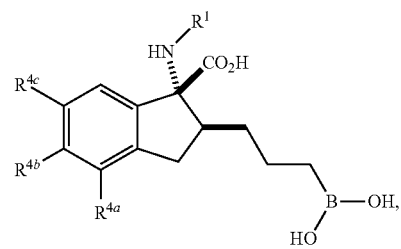
(If)

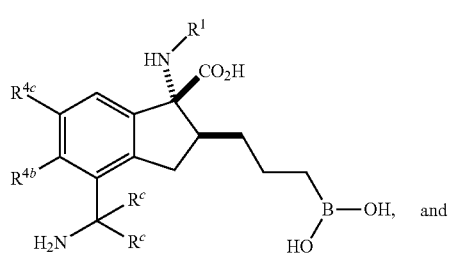
(Ig)

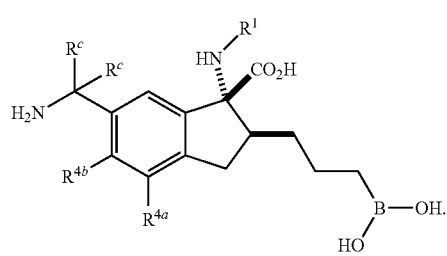
(Ih)

4. The compound of claim 3, or a pharmaceutically acceptable salt, hydrate, or solvate thereof, wherein the compound of formula (Ih) has the formula:

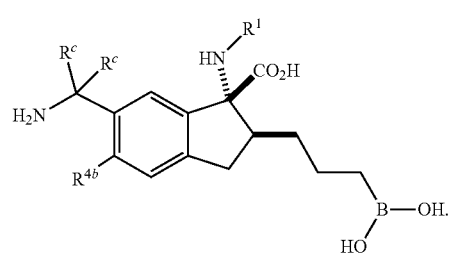
(Ii)

5. The compound of claim 4, or a pharmaceutically acceptable salt, hydrate, or solvate thereof, wherein $R^{4b}$ is selected from the group consisting of H, $CH_3$, CN, $CF_3$, F, and Cl.

6. The compound of claim 4, or a pharmaceutically acceptable salt, hydrate, or solvate thereof, having the formula:

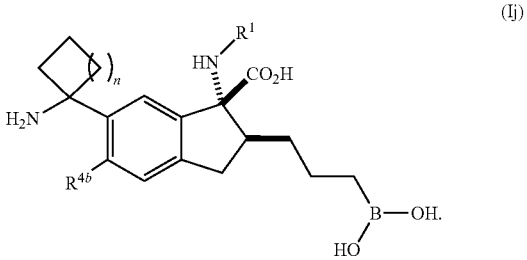
(Ij)

wherein n is 1, 2, or 3; or

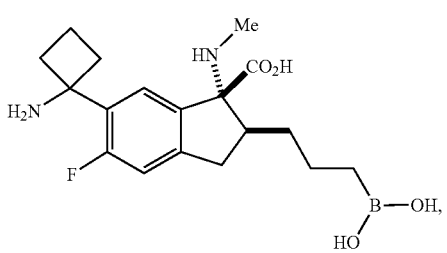
(Ik)

7. The compound of claim 6, or a pharmaceutically acceptable salt, hydrate, or solvate thereof, having a formula selected from the group consisting of:

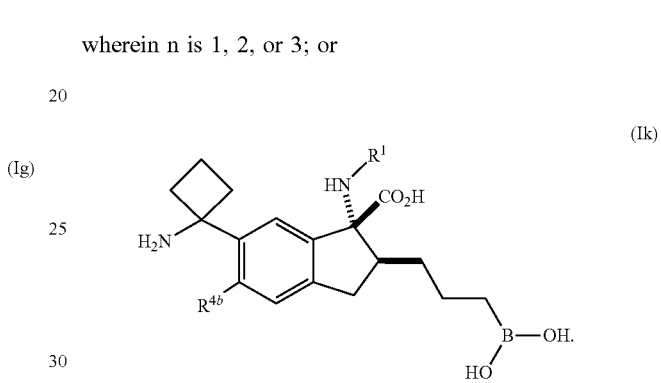

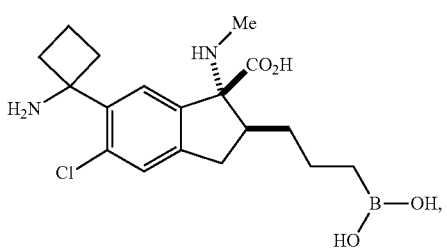

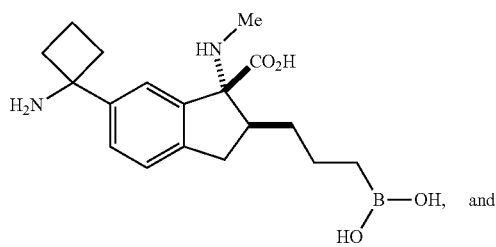
and

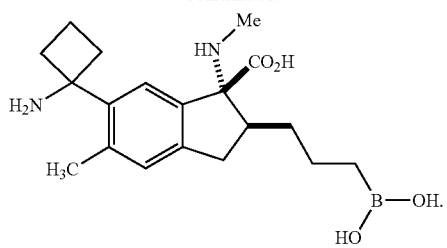
8. The compound of claim 1, selected from the group consisting of
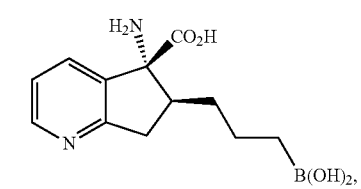
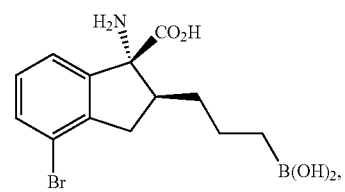
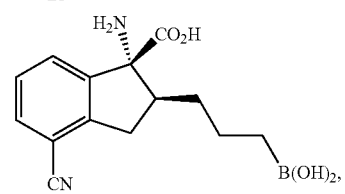
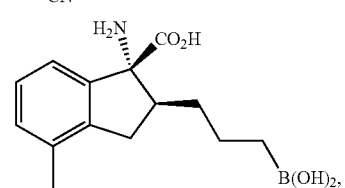
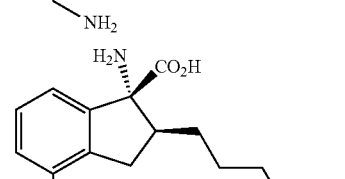
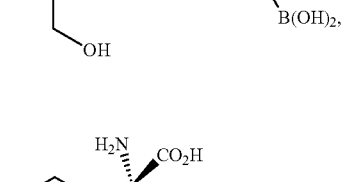
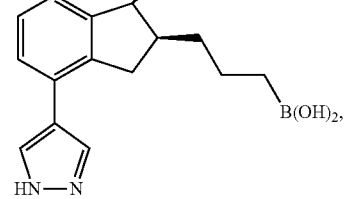
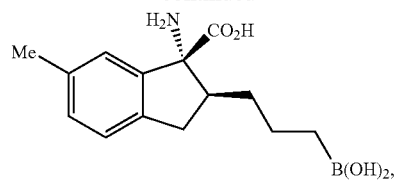
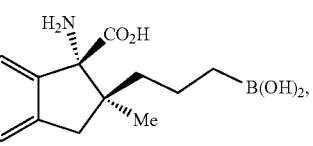
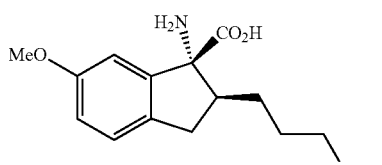
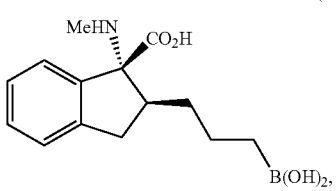
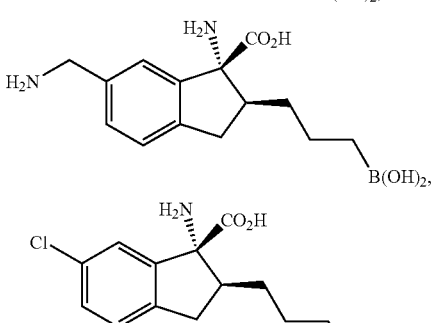
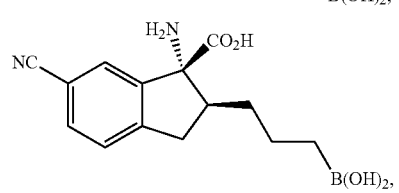
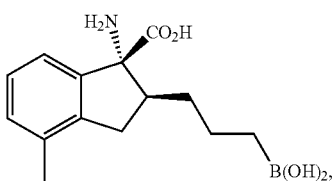
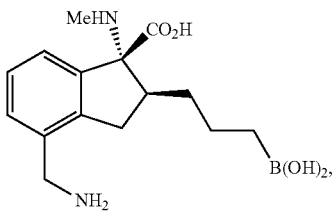

-continued
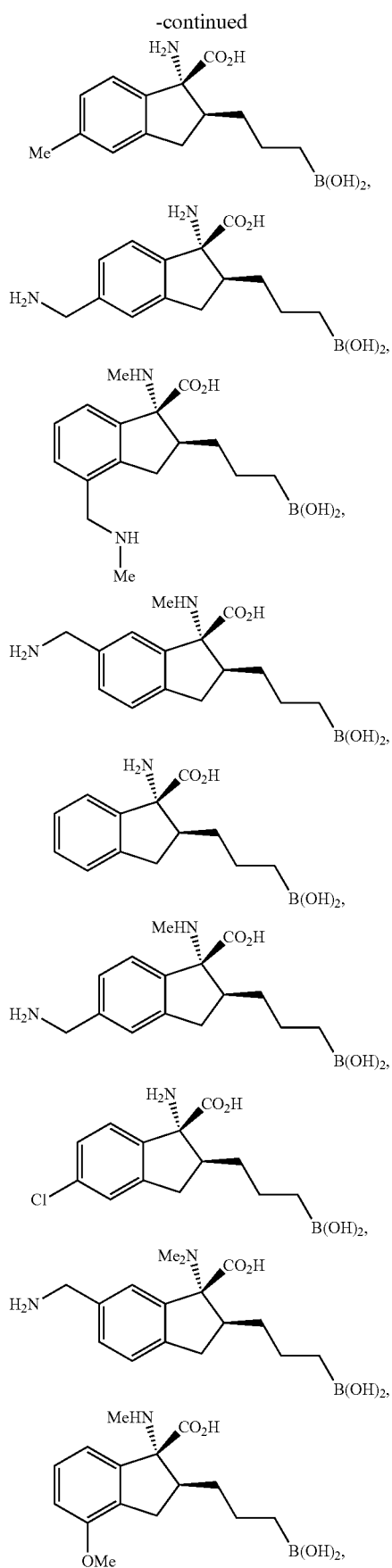
-continued
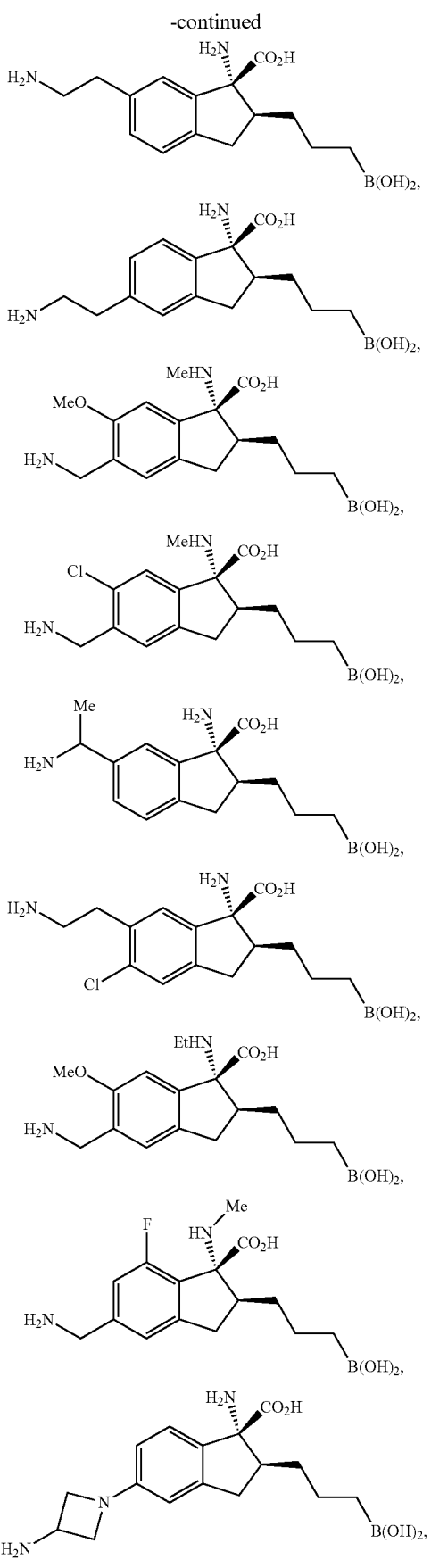

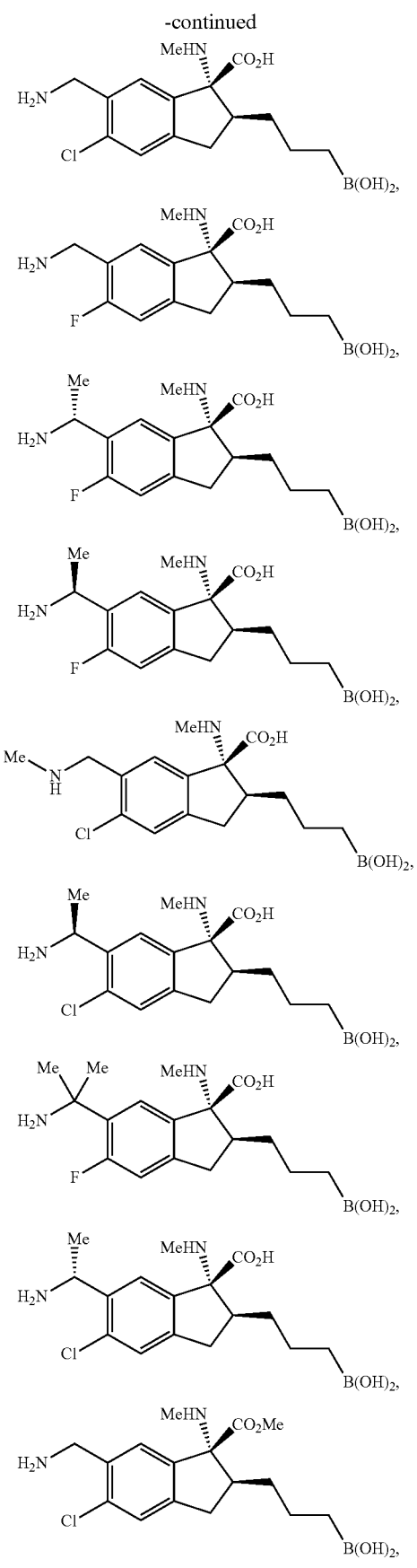
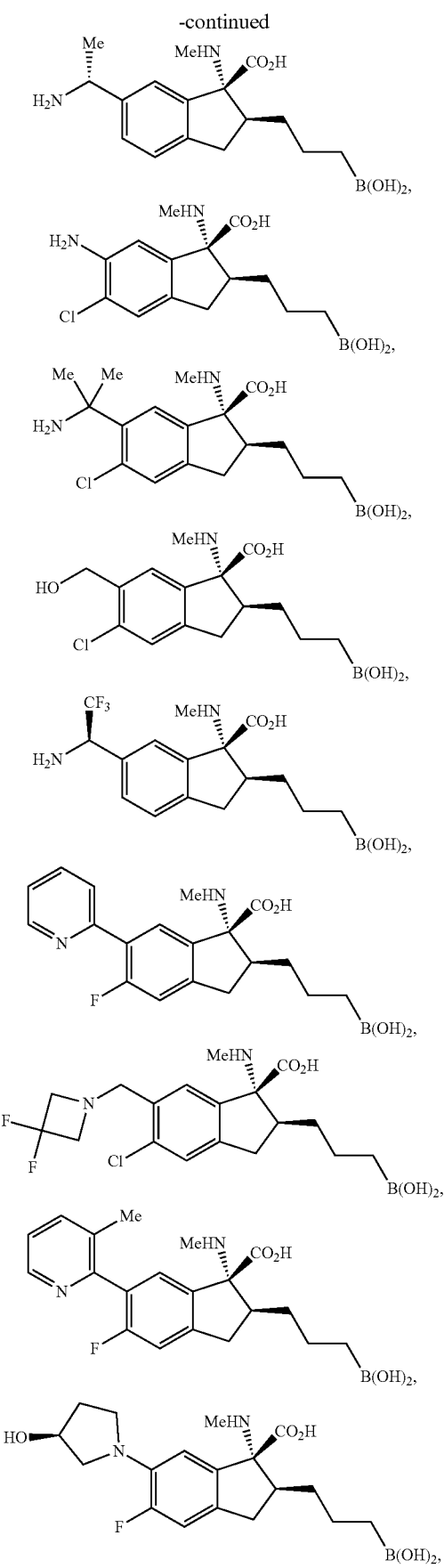

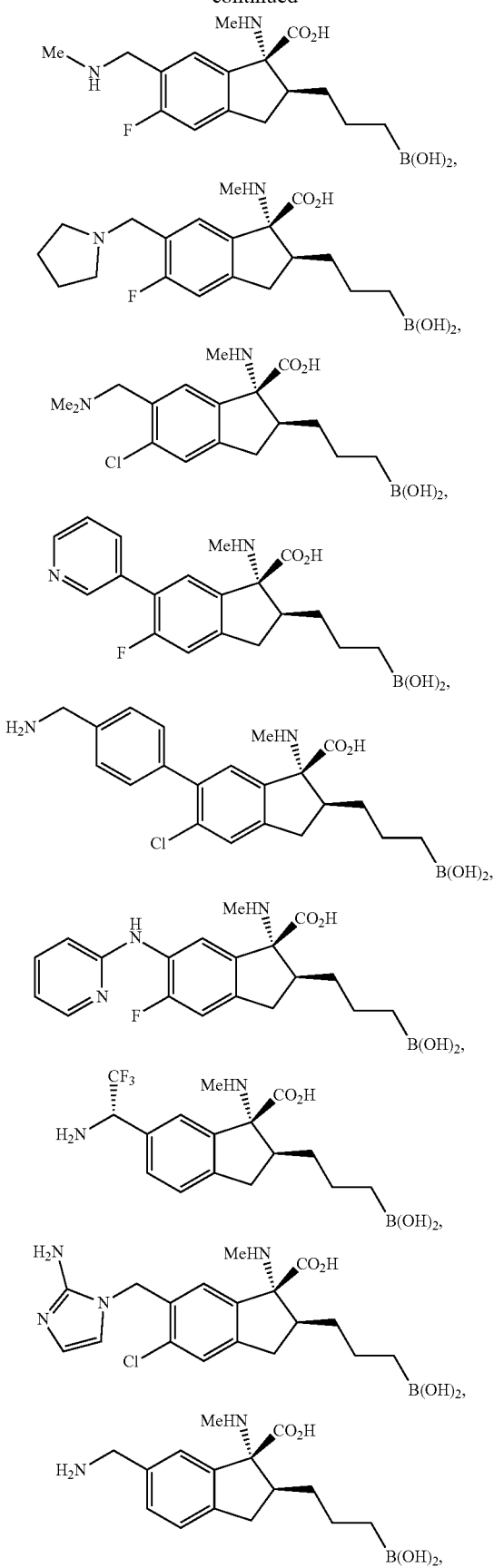
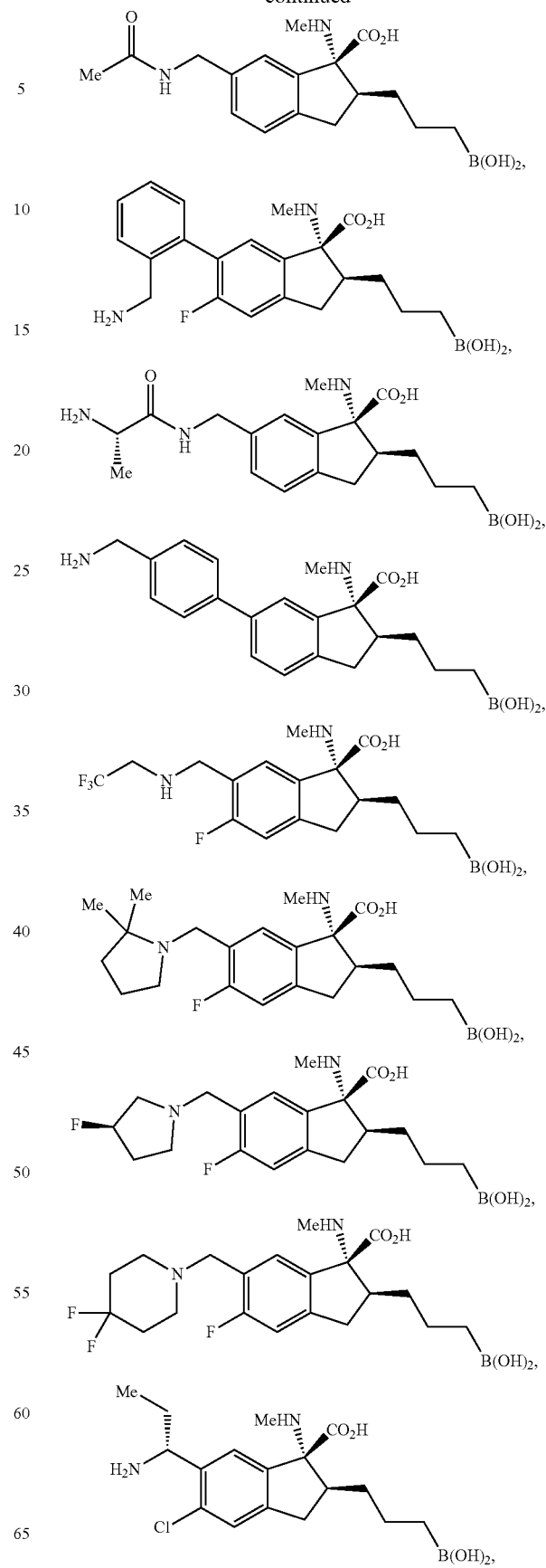

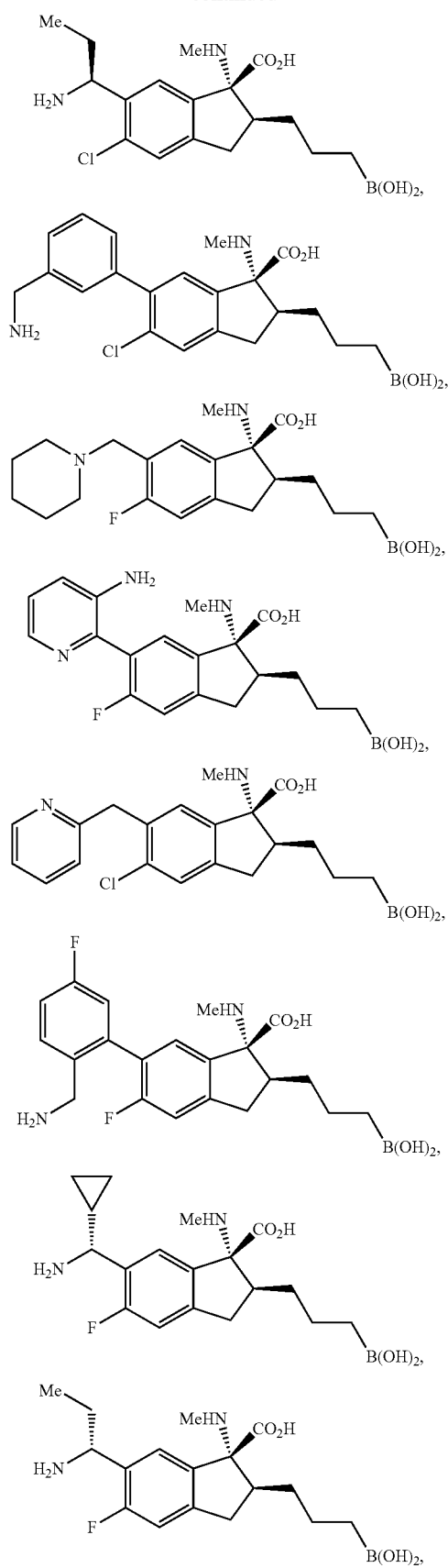
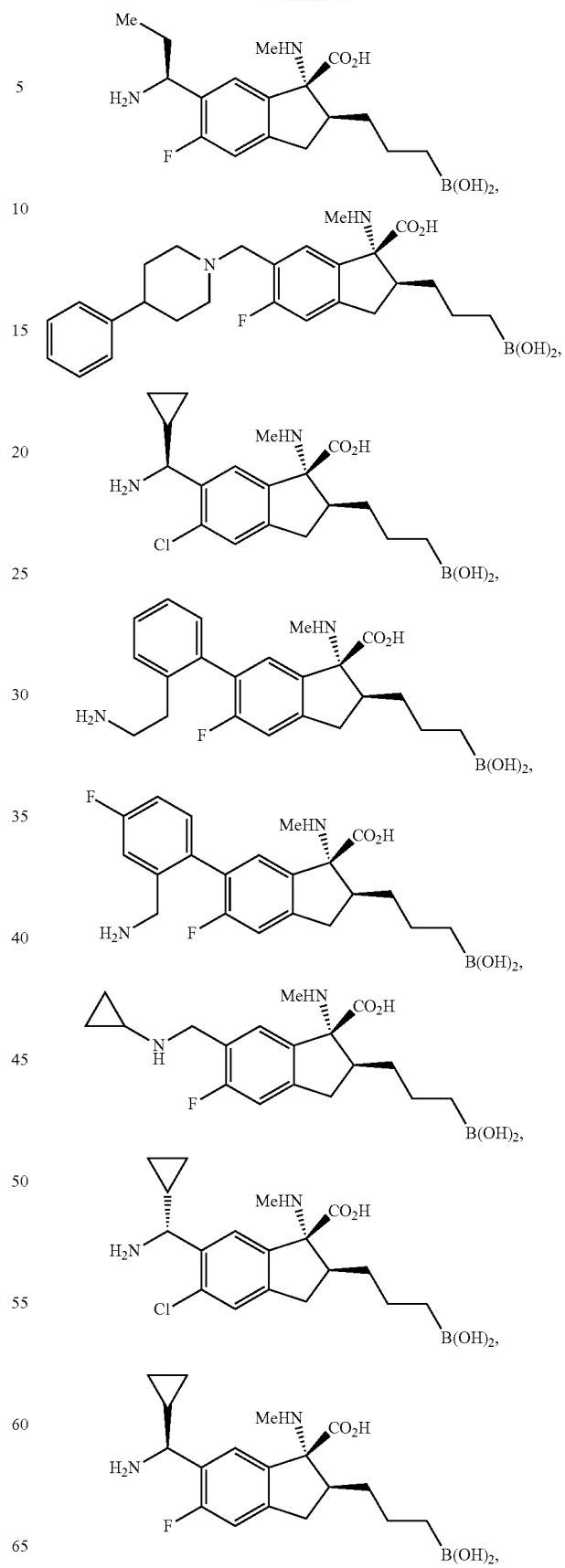

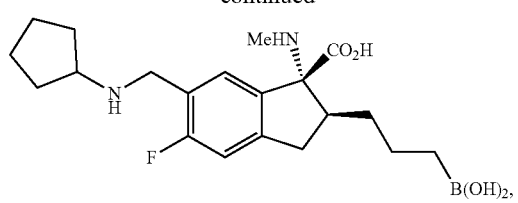
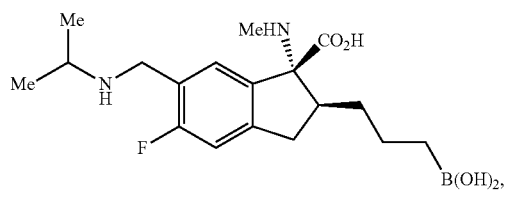
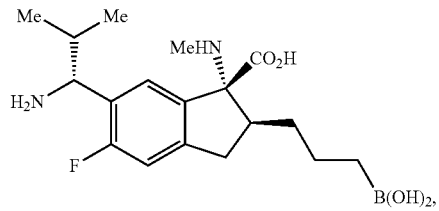
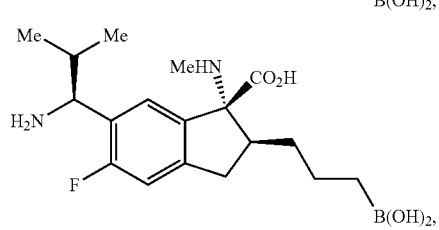
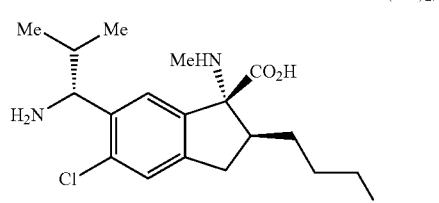
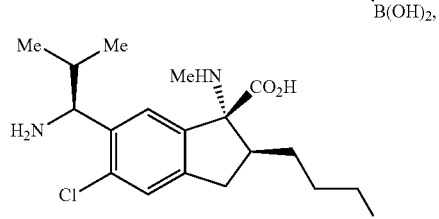
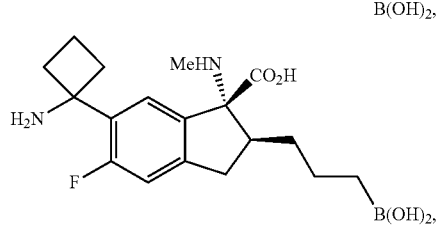
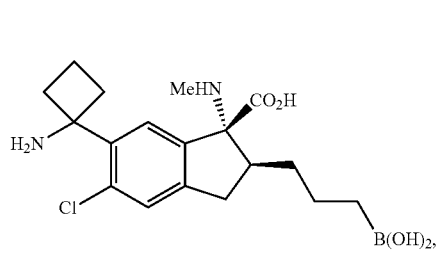
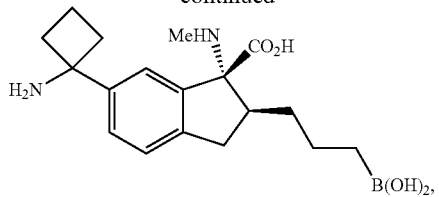
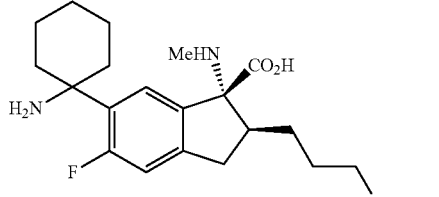
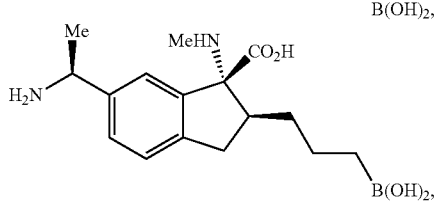
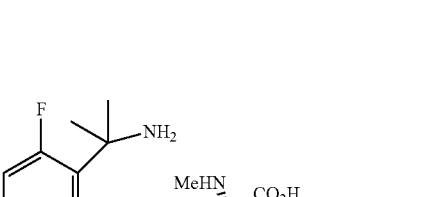
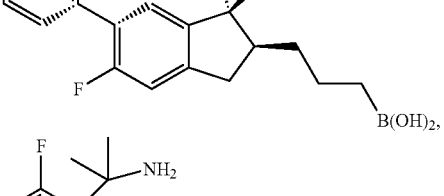
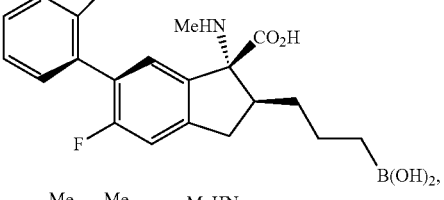
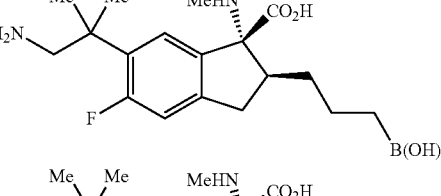
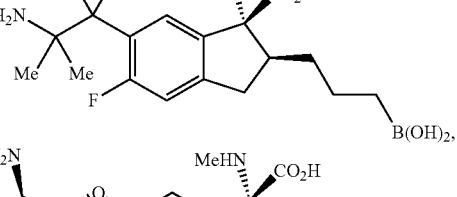
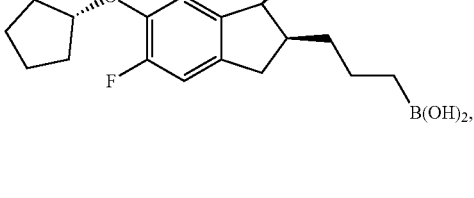

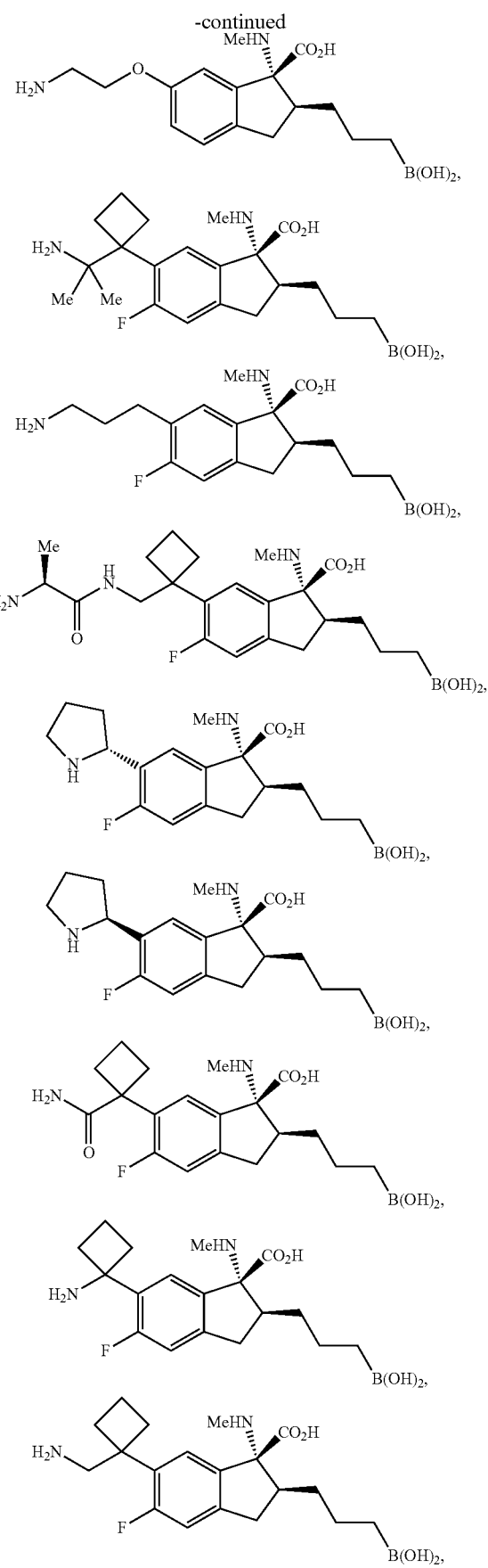
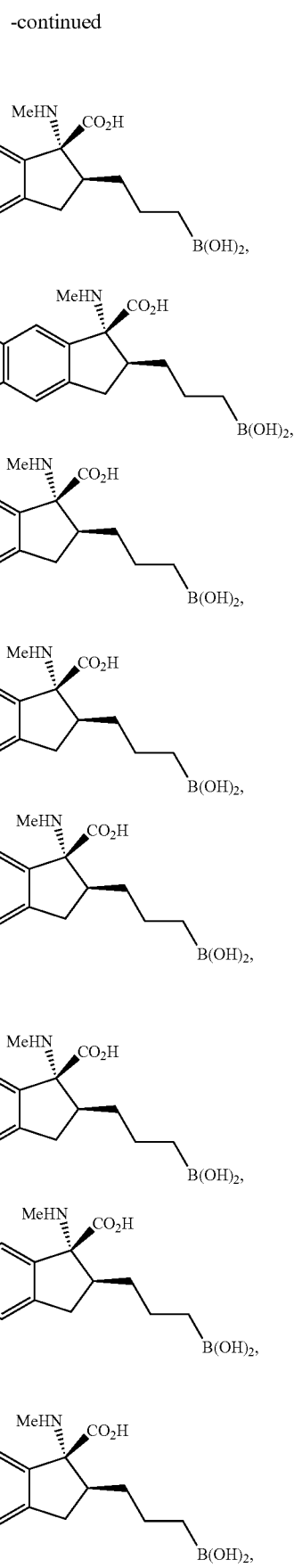

107

-continued

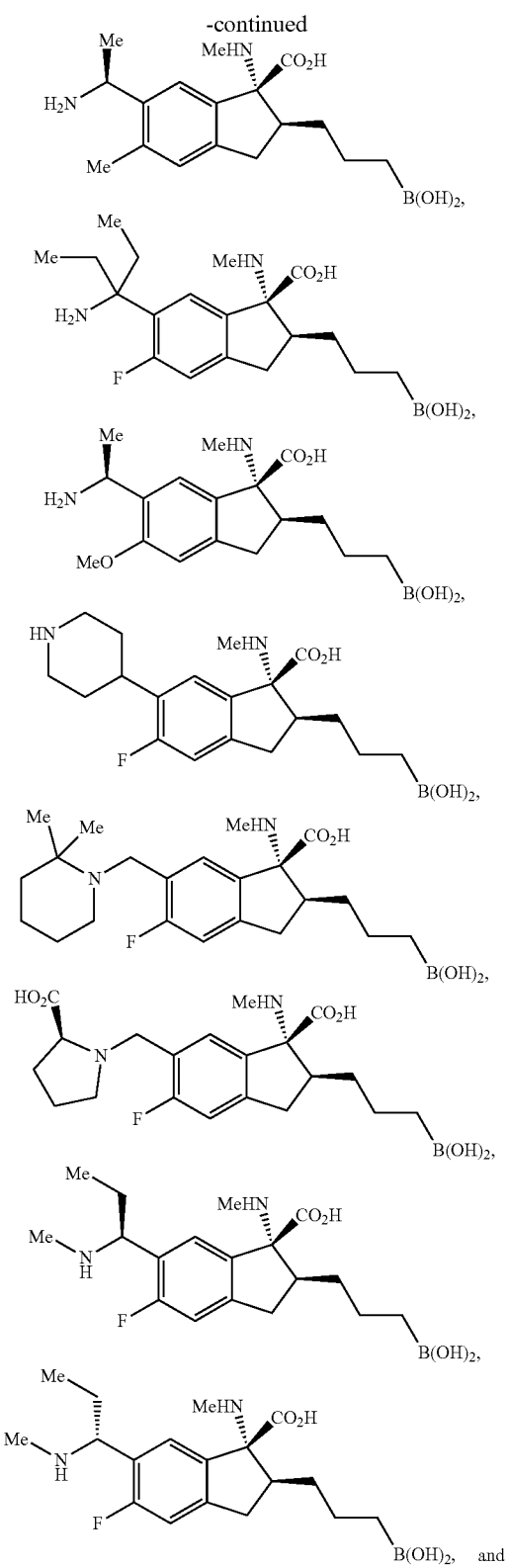

108

-continued

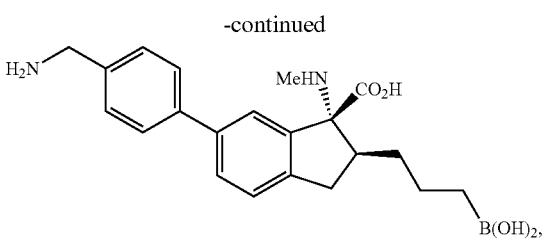

or a pharmaceutically acceptable salt thereof.

9. The compound of claim 8, selected from the group consisting of:

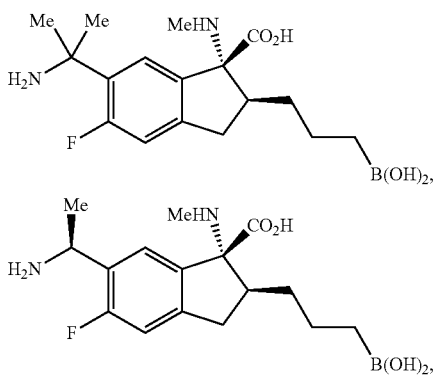

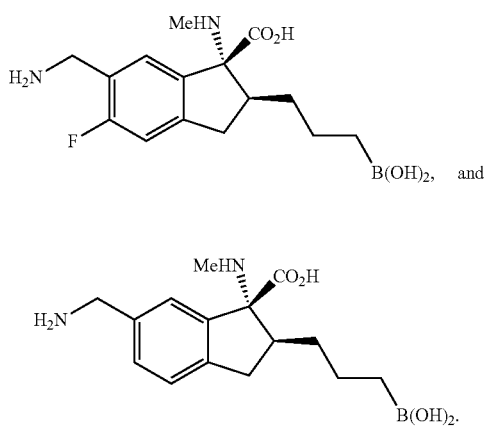

or a pharmaceutically acceptable salt thereof.

10. A combination comprising a compound of claim 1, or a pharmaceutically acceptable salt, hydrate, or solvate thereof, and at least one additional therapeutic agent.

11. A pharmaceutical composition, comprising a compound of claim 1, or a pharmaceutically acceptable salt, hydrate, or solvate thereof, and a pharmaceutically acceptable excipient.

* * * * *